United States Patent [19]

Hjort

[11] Patent Number: 5,879,664
[45] Date of Patent: Mar. 9, 1999

[54] FUNGAL PROTEIN DISULFIDE ISOMERASE

[75] Inventor: Carsten Mailand Hjort, Værløse, Denmark

[73] Assignee: Novo Nordisk A/S, Bagsvaerd, Denmark

[21] Appl. No.: 557,122

[22] PCT Filed: Jun. 28, 1994

[86] PCT No.: PCT/DK94/00266

§ 371 Date: Dec. 11, 1995

§ 102(e) Date: Dec. 11, 1995

[87] PCT Pub. No.: WO95/00636

PCT Pub. Date: Jan. 5, 1995

[30] Foreign Application Priority Data

Jun. 28, 1993 [DK] Denmark .................................. 0768/93

[51] Int. Cl.⁶ ............................. A61K 7/09; A61K 38/51; C12N 9/90; A45D 7/00
[52] U.S. Cl. ...................... 424/70.2; 424/94.1; 424/94.2; 424/94.5; 435/233; 132/210
[58] Field of Search ..................... 435/233, 189, 435/187, 188; 132/210; 424/70.2, 94.1, 94.2, 94.5

[56] References Cited

U.S. PATENT DOCUMENTS

| | | | |
|---|---|---|---|
| 4,894,340 | 1/1990 | Hammer et al. | 435/189 |
| 5,496,719 | 3/1996 | Yamada et al. | 435/233 |

FOREIGN PATENT DOCUMENTS

| | | |
|---|---|---|
| 0 293 793 A2 | 5/1988 | European Pat. Off. . |
| 0272781 | 6/1988 | European Pat. Off. . |
| 0276547 | 8/1988 | European Pat. Off. . |
| 0277563 | 8/1988 | European Pat. Off. . |
| WO 93/25676 | 12/1993 | WIPO . |

OTHER PUBLICATIONS

Mizunaga et al. (1990) Purification and characterization of yeast protein disulfide isomerase. J. Biochm. 108: 846–851, Jan. 1990.

Lundstrom et al. (1992) A Pro to His mutation in active site of thioredoxin increases its disulfide–isomerase activity 10–fold. J. Biol. Chem. 267 (13): 9047–9052, May 1992.

Rudinger (1976) Characteristics of the amino acids as components of a peptide hormone sequence. In: Peptide Hormones. Ed. J. A. Parsons, University Park Press, Baltimore, MD, pp. 1–7, Jun. 1976.

Schreiber (1973) Hair–shaping composition. STN Online, Chemical Abstracts, Columbus, OH, Caplus No. 1973:140360, Mar. 1973.

Miyamoto (1988) Skin cosmetics containing sulfhydryl oxidase and water–soluble polyhydric alcohols. STN Online, Chemical Abstracts, Columbus, OH. Caplus No. 1990:597686, Dec. 1988.

Miyamoto (1989) Hair cosmetic compositions containing sulfhydryl oxidase and water–soluble polyalcohols. STN Online< Chemical Abstracts, Columbus, OH. Caplus No. 1990:637563, Feb. 1989.

Kise et al. (1992) Hair wave–setting oxidizing agents containing enzyme. STN Online, Chemical Abstracts, Columbus, OH. Caplus No. 1992:241716, Apr. 1990.

Sugiyama et al., Biosci. Biotech. Biochem. vol. 57, No. 10, pp. 1704–1707, 1993.

*Primary Examiner*—Robert A. Wax
*Assistant Examiner*—Einar Stole
*Attorney, Agent, or Firm*—Steve T. Zelson, Esq.; Valeta Gregg, Esq.

[57] ABSTRACT

A fungal protein disulfide isomerase obtainable from fungal species belonging to Aspergillus, especially *A. oryzae*, or *A. niger*, is disclosed. Furthermore sequences for recombinant production of the protein disulfide isomerase are disclosed.

28 Claims, 1 Drawing Sheet

FUNGAL PROTEIN DISULFIDE ISOMERASE

FIELD OF THE INVENTION

The present invention relates to an active recombinant fungal protein disulfide isomerase, compositions comprising said fungal protein disulfide isomerase, and methods for their use; a DNA construct comprising a DNA sequence encoding said fungal protein disulfide isomerase, and a vector and cell harbouring the DNA construct. Furthermore, the present invention relates to a method of preparing the fungal protein disulfide isomerase by use of both traditional and recombinant DNA techniques.

BACKGROUND OF THE INVENTION

The use of protein disulfide redox agents such as protein disulfide isomerases (PDI), and thioredoxins (TRX) for various purposes has been known for some time.

Protein disulfide redox agents catalyse the general reaction:

$$R_1\text{—SH} + R_2\text{—SH} + Enz_{ox} \leftrightarrows R_1\text{—S—S—}R_2 + Enz_{red} \quad \text{(reaction I)}$$

where $R_1$ and $R_2$ represent protein entities which are the same or different, either within the same polypeptide or in two polypeptides, $Enz_{ox}$ is a protein disulfide redox agent in the oxidised state, and $Enz_{red}$ is a protein disulfide redox agent in the reduced state. EC 5.3.4.1 refers to an enzyme capable of capable of catalysing the rearrangement of —S—S— bonds in proteins and EC 1.6.4.4 and EC 1.8.4.2 is an example of enzymes catalysing the reaction with NAD(P)H and glutathione as a mediator, respectively.

This type of activity has been designated as protein disulfide isomerase, sulfhydryl oxidase, protein disulfide reductase, disulfide isomerase, protein disulfide transhydrogenase, and sulfhydryl oxidase.

Disulfide linkages in proteins are formed between cysteine residues and have the general function of stabilising the three dimensional structure of the proteins. They can be formed between cysteine residues of the same or different polypeptides.

Disulfide linkages are present in many types of proteins such as enzymes, structural proteins, etc. Enzymes are catalytic proteins such as proteases, amylases, etc., while structural proteins can be scleroproteins such as keratin, etc. Protein material in hair, wool, skin, leather, hides, food, fodder, stains, and human tissue contains disulfide linkages. Treatment of some of these materials with PDI and TRX, and a redox partner have been described previously.

The use of TRX for waving, straightening, removing and softening of human and animal hair was described by Pigiet et al. (EP 183506 and WO 8906122). Pigiet (U.S. Pat. No. 4,771,036) also describes the use of TRX for prevention and reversal of cataracts. Schreiber (DE 2141763 and DE 2141764) describes the use of protein disulfide transhydrogenase for changing the form of human hair. Pigiet (EP 225156) describes the use of TRX for refolding denatured proteins. Use of TRX to prevent metal catalysed oxidative damage in biological reactions is described by Pigiet et al. (EP 237189).

Toyoshima et al. (EP 277563 and EP 293793) describes the use of PDI to catalyse renaturation of proteins having reduced disulfide linkages or unnatural oxidised disulfide linkages, in particular in connection with renaturation of recombinantly produced proteins. Brockway (EP 272781), and King and Brockway (EP 276547) describe the use of PDI for reconfiguration of human hair, and for treatment of wool, respectively. Sulfhydryl oxidase for the treatment of Ultra-high temperature sterilized milk is described in U.S. Pat. No. 4,894,340, U.S. Pat. No. 4,632,905, U.S. Pat. No. 4,081,328 and U.S. Pat. No. 4,053,644. Schreiber (DE 2141763 and DE 2141764) describes the use of protein disulfide transhydrogenase for changing the form of human hair.

The uses of such enzymes have all been connected with reduction of protein disulfide linkages to free protein sulhydryl groups and/or the oxidation of protein sylfhydryl groups to protein disulfide linkages, and/or the rearrangement of disulfide linkages in the same or between different polypeptides, and sometimes to the use of these processes in sequence.

Protein disulfide redox agents can be divided into two main groups of enzymes, thioredoxin type (TRX), and protein disulfide isomerase type (PDI).

Both these can be modified to obtain protein engineered derivatives, chemical modifications and hybrids of TRX and/or PDI (ENG).

TRX is a 12-kDa protein having a redox-active disulfide/dithiol and catalysing thiol-disulfide exchange reactions (Edman et al., Nature 317:267–270, 1985; Holmgren, Ann. Rev. Biochem. 54:237–271, 1985; Holmgren, J. Biol. Chem. 264:13963–13966, 1989). PDI consists of two subunits, each consisting of two domains which are homologous to TRX.

TRX and PDI can be obtained from a number of sources: PDI: protein disulfide isomerases have mainly been identified from mammalian sources, such as Bovine (Yamauchi et al., Biochem. Biophys. Res. Commun. 146:1485–1492, 1987), Chicken (Parkkonen et al., Biochem. J. 256:1005–1011, 1988), Human (Rapilajaniemi et al. EMBO J. 6:643–649, 1987), Mouse (Gong, et al., Nucleic Acids Res. 16:1203, 1988), Rabbit (Fliegel et al., J. Biol. Chem. 265:15496–15502, 1990), and Rat (Edman et al., Nature 317:267–270, 1985). PDI has furthermore been isolated from yeast (Tachikawa et al., J. Biochem. 110:306–313).

TRX: Thioredoxin has been identified from bacteriophages, bacteria such as *Escherichia coli* (Wallace and Kusher, Gene 32:399–408, 1984) and *Bacillus subtilis* (Chen et al. J. Biol Chem. 262:8787–8798, 1987) and eukaryotes.

It would be desirable to facilitate the production of protein disulfide isomerase (PDI), to be able of producing both larger amounts of the enzyme and to produce it in a more economical manner than what is possible by the prior art methods.

Engineered variants (ENG) with improved properties for particular applications are also highly desirable and can be prepared by a variety of methods based on standard recombinant DNA technology:

1) by using site-directed or random mutagenesis to modify the genes encoding TRX or PDI in order to obtain ENG with one or few amino acid changes,
2) by inhibiting or otherwise avoiding dimerisation of the subunits of PDI, thus giving rise to PDI monomers,
3) by producing partial monomers of PDI or TRX, in which regions of the NH2— or COOH termini of PDI or TRX are lacking,
4) by creating hybrids of PDI, TRX and/or ENG,
5) by chemically or enzymatically modifying the products of 1)-4),
6) by a combination of any of 1)-5).

ENG produced according to 1) were described by Lundström et al. (J. Biol. Chem. 267:9047–9052, 1992) and by a combination of 3) and 5) by Pigiet (WO 8906122).

PDI, and TRX can, apart from their natural sources, be obtained by expression of recombinant DNA encoding plant, animal, human or microbial PDI, or TRX, in various hosts, such as microorganisms followed by purification of PDI, or TRX from extracts or supernatants of said host organisms. This goes also for ENG. Preparation of Trx from natural sources is described by Luthman and Holmgren (Biochem. 121:6628–6633, 1982), Wada and Buchanan (in "Thioredoxins, structure and function" (Gadal, Ed.) Editions du Centre National de la Recherche Scientifique), Porque et al. (J. Biol. Chem. 245:2362–2379, 1970) and by Laurent et al. (J. Biol. Chem. 239:3436–3445), whereas recombinant production of TRX is described by Krause et al. (J. Biol. Chem. 266:9494–9500). PDI or sulfhydryl oxidase has been prepared from natural sources by Lambert and Freedman (Biochem J. 213:225–234, 1983), Starnes et al. (U.S. Pat. No. 4,632,905) and Hammer et al. (U.S. Pat. No. 4,894,340), and by recombinant technology by among others Yamauchi et al. (Biochem. Biophys. Res. Commun. 146:1485–1492, 1987). Finally, recombinant production of an ENG is described by Lundström et al. (J. Biol. Chem. 267:9047–9052, 1992).

SUMMARY OF THE INVENTION

The present inventors have succeeded in cloning a DNA sequence encoding a fungal protein disulfide isomerase from filamentous fungi and in obtaining expression of an active protein disulfide isomerase from said DNA sequence, both in the same species and in other organisms, especially microorganisms, and preferably in fungi.

Accordingly, in a first aspect the present invention relates to an active protein disulfide isomerase obtainable from filamentous fungi, specifically fungi belonging to the genus Aspergillus, and especially a protein disulfide isomerase obtainable from *A. oryzae*, or *A. niger*, which enzyme is immunologically reactive with an antibody raised against a purified protein disulfide isomerase derived from *Aspergillus oryzae*, IFO 4177, or *Aspergillus niger*, A524.

From the sequence of the isolated enzyme it can be seen that the protein disulfide isomerase has two -Cys-X-Y-Cys-subunits in positions 58–61 and 393–396. The invention consequently also comprises active truncated forms of the enzymes of the invention, wherein at least one subunit is retained. Examples hereof could be an enzyme having an amino acid sequence corresponding to the residues 20 to 100, residues 330 to 450, or residues 360 to 430 of the appended SEQ ID No. 3, or the corresponding sequence of the enzyme of the invention in question.

Under this aspect, the invention specifically relates to enzymes exhibiting protein disulfide isomerase activity comprising the amino acid residues 1–131, 1–141, 1–143, 1–163, 1–174, or 1–281, of the amino acid sequence shown in the appended SEQ ID No. 3, or variants thereof exhibiting a protein disulfide isomerase activity. Further specific enzymes are enzymes exhibiting protein disulfide isomerase activity comprising the amino acid residues 1–115, of the amino acid sequence shown in the appended SEQ ID No. 3 extended with the following sequence:

Leu-Ile-Arg-Glu-Leu-Leu-Gln-Glu-Leu-Val-Asn-Lys-His-Leu (SEQ ID NO.11); and an enzyme comprising the amino acid residues 1–511, of the amino acid sequence shown in the appended SEQ ID No. 3, and wherein the amino acid residue in position 511 is changed from Glu to Ala.

In the present context, the term "derived from" is intended not only to indicate a protein disulfide isomerase produced by strains IFO 4177 or A524, but also a protein disulfide isomerase encoded by a DNA sequence isolated from these strains such as indicated in SEQ ID No. 1 and SEQ ID No. 2, or a sequence homologous thereto encoding a polypeptide with protein disulfide isomerase activity and produced in a host organism transformed with said DNA sequence.

Accordingly, the present invention thus relates to an enzyme exhibiting protein disulfide isomerase activity, which enzyme is immunologically reactive with an antibody raised against a purified protein disulfide isomerase derived from *Aspergillus oryzae*, IFO 4177.

In the present context, the term "homologue" is intended to indicate a polypeptide encoded by DNA which hybridizes to the same probe as the DNA coding for the protein disulfide isomerase enzyme under certain specified conditions (such as presoaking in 5×SSC and prehybridizing for 1 h at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~40° C. followed by washing three times in 2×SSC, 0.2% SDS at 40° C. for 30 minutes). More specifically, the term is intended to refer to a DNA sequence which is at least 70% homologous to the sequences indicated above encoding the protein disulfide isomerase of the invention. The term is intended to include modifications of the DNA sequences indicated above, such as nucleotide substitutions which do not give rise to another amino acid sequence of the protein disulfide isomerase but which correspond to the codon usage of the host organism into which the DNA construct is introduced or nucleotide substitutions which do give rise to a different amino acid sequence and therefore, possibly, a different protein structure which might give rise to a protein disulfide isomerase mutant with different properties than the native enzyme. Other examples of possible modifications are insertion of one or more nucleotides into the sequence, addition of one or more nucleotides at either end of the sequence, or deletion of one or more nucleotides at either end or within the sequence.

In the present context the term active protein disulfide isomerase is intended to indicate an enzyme having an activity similar to that of protein disulfide isomerase, i.e. an enzyme capable of catalysing reaction I. The activity may be determined in an assay based on oxidative refolding of reduced Bowman-Birk soya bean inhibitor, e.g. as described in the Materials and Methods section below.

The term "recombinant" as used about the protein disulfide isomerase of the invention is intended to indicate that it is produced by a cell transformed with a DNA sequence encoding the protein disulfide isomerase. Thus, the recombinant protein disulfide isomerase may be produced by either its parent organism or another organism.

In a further aspect the present invention relates to a DNA construct comprising a DNA sequence encoding an active recombinant protein disulfide isomerase of the invention as defined above. Such a DNA construct may comprise introns (an example thereof is shown in the appended SEQ ID No. 1) and/or regulatory elements native to the parts coding for the mature protein disulfide isomerase of the invention, or be a cDNA construct comprising only that part coding for the mature protein disulfide isomerase (an example being the appended SEQ ID No.2).

In still further aspects the present invention relates to a recombinant expression vector harbouring the DNA construct of the invention, to a cell which either harbours the DNA construct or the expression vector of the invention, and to a process for the production of a protein disulfide isomerase of the invention, wherein a cell of the invention as described above is cultured under conditions conducive to the production of the protein disulfide isomerase, and the protein disulfide isomerase is subsequently recovered from the culture.

Finally, the present invention relates to compositions comprising the active protein disulfide isomerase of the invention and methods for their use in various applications.

BRIEF DESCRIPTION OF THE TABLES AND DRAWING

The invention is further illustrated in the accompanying tables and drawing, in which Table 1 shows an alignment of published eukaryotic PDI amino acid sequences: Bovine (*Bos taurus*) (Yamauchi et al., Biochem. Biophys. Res. Commun. 146:1485–1492, 1987), chicken (*Gallus gallus*) (Parkkonen et al., Biochem. J. 256:1005–1011, 1988), human (*Homo sapiens*) (Rapilajaniemi et al. EMBO J. 6:643–649, 1987), mouse (*Mus musculus*) (Gong, et al., Nucleic Acids Res. 16:1203, 1988), rabbit (*Oryctolagus cuniculus*) (Fliegel et al., J. Biol. Chem. 265:15496–15502, 1990), rat (*Rattus norvegicus*) (Edman et al., Nature 317:267–270, 1985), and yeast (*Saccharomyces cerevisiae*) (Tachikawa et al., J. Biochem. 110:306–313) (SEQ ID NOS:26–32, respectively).

Table 2 shows an alignment of PDI amino acid sequences: Alfalfa (*Medicago sativa*) (Shorrosh and Dixon, Plant. Mol. Bio. 19:319–321, 1992), *A. oryzae* (this invention), yeast (*Saccharomyces cerevisiae*) (Tachikawa et al., J. Biochem. 110:306–313), bovine (*Bos taurus*) (Yamauchi et al., Biochem. Biophys. Res. Commun. 146:1485–1492, 1987), rat (*Rattus norvegicus*) (Edman et al., Nature 317:267–270, 1985), and mouse (*Mus musculus*) (Gong, et al., Nucleic Acids Res. 16:1203, 1988) (SEQ ID NOS:33–38, respectively), and FIG. 1 illustrates the construction of the expression plasmids pCaHj431, pCaHj432, pCaHj433, and pCaHj434 further described in Example 1.

DETAILED DESCRIPTION OF THE INVENTION

Figure 1:
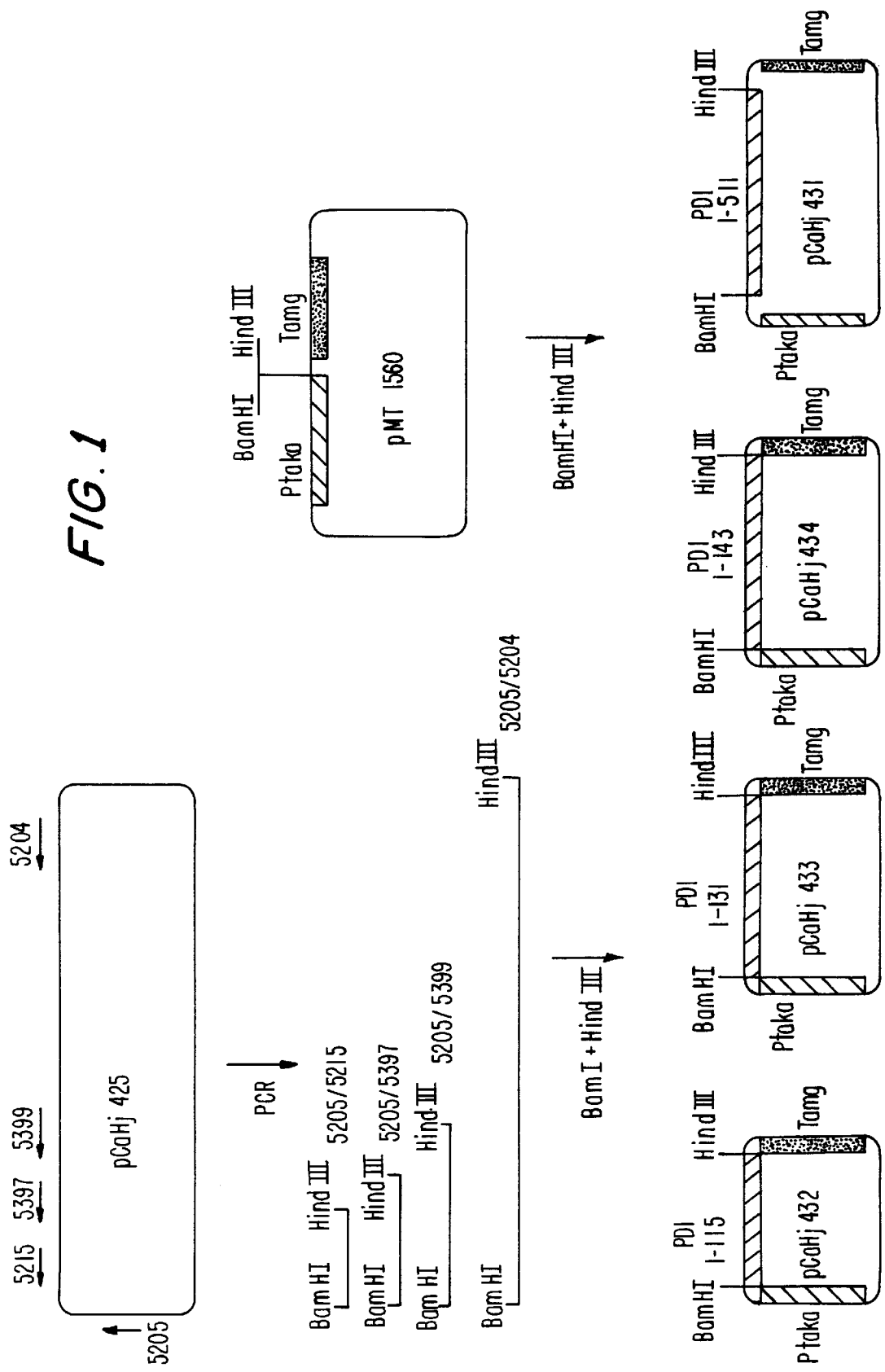

The amino acid sequence of the protein disulfide isomerase of the invention, which was isolated from a strain of the *A. oryzae*, has been aligned with that of protein disulfide isomerases of other origins and have been shown to have a degree of identity of about 38% with that of *Saccharomyces cerevisiae* (GenBank Acc. No. M62815) and 30% with that of Alfalfa (GenBank Acc. No. 11499).

These homologies are taken to indicate that some kind of evolutionary relationship exists between protein disulfide isomerases, and that the protein disulfide isomerase of the invention may represent a distinct class of protein disulfide isomerase. It is contemplated that the protein disulfide isomerase of the invention or DNA encoding the protein disulfide isomerase may be isolated from other organisms, including animals, especially a mammal, an insect, a plant or a microorgamism. In the present context, especially interesting origins are bacteria and fungi, including yeasts and filamentous fungi.

As indicated above the sequence of the isolated enzyme shows that the protein disulfide isomerase of the invention has two -Cys-X-Y-Cys- subunits in positions 58–61 and 393–396.

The invention consequently also comprises active truncated forms of the enzymes of the invention, wherein at least one subunit is retained. Examples hereof could be an enzyme having an amino acid sequence corresponding to the residues 20 to 100, residues 330 to 450, or residues 360 to 430 of the appended SEQ ID No. 3, or the corresponding sequence of the enzyme of the invention in question.

Under this aspect, the invention specifically relates to enzymes exhibiting protein disulfide isomerase activity comprising the amino acid residues 1–131 (SEQ ID No. 10), 1–141 (SEQ ID No.9), 1–143 (SEQ ID No. 8), 1–163 (SEQ ID No. 7), 1–174 (SEQ ID No. 6), 1–281 (SEQ ID No. 5), or 25–225 (SEQ ID No. 12) of the amino acid sequence shown in the appended SEQ ID No. 3, or variants/derivatives thereof exhibiting a protein disulfide isomerase activity. Further specific enzymes are enzymes exhibiting protein disulfide isomerase activity comprising the amino acid residues 1–115, of the amino acid sequence shown in the appended SEQ ID No. 3 extended with the following sequence:

Leu-Ile-Arg-Glu-Leu-Leu-Gln-Glu-Leu-Val-Asn-Lys-His-Leu (SEQ ID No. 11); and an enzyme comprising the amino acid residues 1–511, of the amino acid sequence shown in the appended SEQ ID No. 3, and wherein the amino acid residue in position 511 is changed from Glu to Ala (SEQ ID No. 4).

The DNA sequence of the DNA construct of the invention encoding a recombinant protein disulfide isomerase enzyme as defined above is preferably as shown in the appended SEQ ID No. 1 (genomic DNA) or SEQ ID No. 2 (cDNA). Analogues of said sequences, which differ in one or more codons, but which encodes the recombinant protein disulfide isomerase are also within the invention.

Similar DNA sequences coding for the truncated forms of the protein disulfide isomerases of the invention are also part of the invention. DNA sequences therefore can be taken from SEQ ID No. 1, or preferably SEQ ID No. 2.

The DNA sequence of the DNA construct of the invention may be isolated by well-known methods. Thus, the DNA sequence may, for instance, be isolated by establishing a cDNA or genomic library from an organism expected to harbour the sequence, and screening for positive clones by conventional procedures. Examples of such procedures are hybridization to oligonucleotide probes synthesized on the basis of the full amino acid sequence shown in SEQ ID No. 3, or a subsequence thereof in accordance with standard techniques (cf. Sambrook et al., 1989), and/or selection for clones expressing a protein disulfide isomerase activity as defined above, and/or selection for clones producing a protein which is reactive with an antibody raised against the protein disulfide isomerase comprising the amino acid sequence shown in SEQ ID No. 3 and in particular amino acid residues 1–143 thereof as shown in SEQ ID No. 8.

A preferred method of isolating a DNA construct of the invention from a cDNA or genomic library is by use of polymerase chain reaction (PCR) using degenerate oligonucleotide probes prepared on the basis of the amino acid sequence of the protein disulfide isomerase of the invention comprising amino acid residues 1–515 of SEQ ID No. 3. For instance, the PCR may be carried out using the techniques described in U.S. Pat. No. 4,683,202 or by R. K. Saiki et al. (1988).

Alternatively, the DNA sequence of the DNA construct of the invention may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA construct may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire recombinant DNA molecule, in accordance with standard techniques.

DNA constructs coding for the truncated forms of the enzyme of the invention may naturally be made in corresponding ways.

The recombinant expression vector carrying the DNA construct of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the recombinant protein disulfide isomerase of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Examples of Aspergillus selection markers include amdS, argB, niaD and sC, a marker giving rise to hygromycin resistance. Furthermore, the selection may be accomplished by co-transformation, e.g. as described in WO 91/17243.

While intracellular expression may be advantageous in some respects, e.g. when using certain bacteria as host cells, it is generally preferred that the expression is extracellular. The protein disulfide isomerase of the invention or truncated forms thereof comprising the amino acid sequences shown in the SEQ ID Nos. 3 to 12 may furthermore comprise a preregion permitting secretion of the expressed protein disulfide isomerase into the culture medium. If desirable, this preregion may be native to the protein disulfide isomerase of the invention or substituted with a different preregion or signal sequence, conveniently accomplished by substitution of the DNA sequences encoding the respective preregions.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. (1989)).

The cell of the invention either comprising a DNA construct or an expression vector of the invention as defined above is advantageously used as a host cell in the recombinant production of a polypeptide of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal, an avian, an insect, or a plant cell, but is preferably a microbial cell, e.g. a bacterial or a fungal (including yeast) cell.

Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may for instance be effected by protoplast transformation or by using competent cells in a manner known per se.

The yeast organism may favourably be selected from a species of Saccharomyces or Schizosaccharomyces, e.g. *Saccharomyces cerevisiae*. The filamentous fungus may advantageously belong to a species of Aspergillus, e.g. *Aspergillus oryzae* or *Aspergillus niger*. Alternatively, a strain of a Fusarium species, e.g. *F. oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

In a yet further aspect, the present invention relates to a method of producing a recombinant protein disulfide isomerase of the invention, which method comprises cultivating a host cell as described above under conditions conducive to the production of the protein disulfide isomerase and recovering the protein disulfide isomerase from the cells and/or culture medium.

The medium used to cultivate the cells may be any conventional medium suitable for growing the host cell in question and obtaining expression of the protein disulfide isomerase of the invention. Suitable media are available from commercial suppliers or may be prepared according to published recipes (e.g. in catalogues of the American Type Culture Collection).

The resulting protein disulfide isomerase may be recovered from the medium by conventional procedures including separating the cells from the medium by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

It is of course also possible to produce the protein disulfide isomerases of the invention by culturing the filamentous fungal natural host or parent organism of interest and recovering the protein disulfide isomerase from the culture broth in traditional ways.

The present invention also relates to compositions comprising the protein disulfide isomerase of the invention.

The compositions may suitably contain 0.01–200 mg of enzyme protein per gram, preferably 0.01–20 mg of enzyme protein per gram, especially 0.01–2 mg of enzyme protein per gram, or alternatively 0.02–0.2 mg of enzyme protein per gram, or 0.01–0.2 mg of enzyme protein per gram.

The compositions of the invention may contain other ingredients known in the art as e.g. excipients, stabilizers, fillers, detergents, etc.

The compositions of the invention may be formulated in any convenient form, e.g. as a powder, paste, liquid or in granular form. The enzyme may be stabilized in a liquid by inclusion of enzyme stabilizers. Usually, the pH of a solution of the composition of the invention will be 5–10 and in some instances 7.0–8.5. Other enzymes such as proteases, cellulases, oxidases, peroxidases, amylases or lipases may be included in the compositions of the invention, either separately or in a combined additive.

The compositions of the invention can be used for the treatment or degradation of scleroproteins, especially hair, skin and wool, dehairing and softening of hides, treatment and cleaning of fabrics, as additives to detergents, thickening and gelation of food and fodder, strengthening of gluten in bakery or pastry products, and as pharmaceuticals for the alleviation of eye sufferings.

The present invention is further illustrated in the following examples which should not, in any manner, be considered to limit the scope of the present invention.

MATERIALS AND METHODS

Strains

*Aspergillus oryzae* IFO 4177 available from Institute for Fermentation, Osaka; 17–25 Juso Hammachi 2-Chome Yodogawa-Ku, Osaka, Japan.

*Aspergillus niger* A524 (ATCC 16882)

*Aspergillus niger* TSA 1.

*E. coli* DH5αF'

Determination of PDI activity

The PDI is assayed using the insulin reduction assay described by James et al., Cell 67:581–589, 1991.

Plasmids pUC 19, pMT 1560, pToC 90

EXAMPLES

Example 1

Cloning of *Aspergillus oryzae* and *Aspergillus niger* PDI encoding genes 1.1. Design of oligo nucleotides for PCR amplification PDI from different organisms are highly homologous especially near the active site residues. In FIG. 1, the following 7 PDI gene products are aligned:

Bovine (*Bos taurus*) PDI (Yamauchi et al., Biochem. Biophys. Res. Commun. 146:1485–1492, 1987), Chicken (*Gallus gallus*) PDI (Parkkonen et al., Biochem. J. 256:1005–1011, 1988), Human (*Homo sapiens*) PDI (Rapilajaniemi et al. EMBO J. 6:643–649, 1987), Mouse (*Mus musculus*) PDI (Gong, et al., Nucleic Acids Res. 16:1203, 1988), Rabbit (*Oryctolagus cuniculus*) PDI (Fliegel et al., J. Biol. Chem. 265:15496–15502, 1990), Rat (*Rattus norvegicus*) PDI (Edman et al., Nature 317:267–270, 1985), Yeast (*Saccharomyces cerevisiae*) PDI (Tachikawa et al., J. Biochem. 110:306–313).

Each subunit contains two active centres (Freedman et al., Cell 57:1069–1072, 1989) and the homology in the surroundings of these active centres are particularly strong. A consensus amino acid sequence for the active centre closest to the N-terminus was determined from the alignment as -APWCGHCK- (SEQ ID NOS:33–38 respectively, and an oligo deoxyribonucleotide encoding the peptide -WCGHCK- (SEQ ID NOS:24) and extended with an EcoRI site in the 5' end, was synthesized:

5'TGGAATTCTGGTGYGGNCAYTGYAA3' (primer 4762, 25 nucleotides, 32 species, SEQ ID No. 13) (Y=C or T; R=A or G; N=A, T, C, or G).

A consensus amino acid sequence for the active centre closest to the C-terminus was determined: -YAPWCGHCK- (SEQ ID NO:24), and an oligo deoxyribonucleotide encoding the peptide -YAPWCG- (SEQ ID NO:24) in antisense and extended with a BamHI site in the 5' end was synthesized:

5'TGGGATCCRCACCANGGNGCRTA3' (primer 4763, 23 nucleotides, 64 species, SEQ ID NO. 14).

These oligo deoxyribonucleotides (primers 4762 and 4763) were used as primers in a PCR reaction to amplify PDI-encoding gene fragments from genomic DNA from *A. oryzae* and *A. niger.*

1.2 Amplification and cloning of fragments of PDI-encoding genes

Genomic DNA was prepared from *Aspergillus oryzae* IFO 4177 and *Aspergillus niger* A524 as described by Yelton et al. (Proc. Natl. Acad. Sci. U.S.A. 81:1470–1474, 1984).

PCR reaction mixtures contained Taq DNA polymerase buffer supplied by Clontech laboratories Inc. and diluted as described, 250 μM of each of dATP, dCTP, dGTP, and, dTTP, 100 pmol of each of primers 4762 and 4763, and 0.5 μg of genomic DNA of either *A. niger* or *A. oryzae.* The total reaction volume was 0.1 ml, and it was covered with 0.05 ml paraffin oil.

The following program was run on a Cetus Perkin Elmer thermal cycler:

1. cycle: 94° C. for 2 min., (when the temperature reached 94° C. 2.5 U of Taq DNA polymerase supplied by Clontech laboratories Inc. was added).

10 cycles: 94° C. for 1 min., 50° C. for 1 min., and 72° C. for 2 min.

30 cycles: 94° C. for 1 min., 55° C. for 1 min., and 72° C. for 2 min.

1 cycle: 72° C. for 5 min.

The reaction mixtures were loaded on an agarose gel, and both the A. oryzae and the A. niger DNA produced fragments of approximately 1.1 kb.

The fragments were digested with EcoRI and BamHI and ligated to pUC19 (Yanisch-Perron et al., Gene 33:103–119, 1985). The ligation mixture was transformed into E. coli DH5αF' (Woodcock et al., Nucleic Acids Res. (1989) 17:3469–3478). Recombinant plasmids were subjected to sequence analysis using the Sequenase™ kit (United States Biochemical) and a M13 universal primer following the manufacturers instructions. The analysis confirmed that both in the case of A. oryzae and in that of A. niger sequences homologous to other PDI genes were amplified and cloned.

1.3 Genome cloning of the A. oryzae PDI-encoding gene

Genomic DNA from A. oryzae was digested with the following restriction enzymes supplied by New England Biolabs Inc.: HindIII, BamHI, BamHI+HindIII, EcoRI, EcoRI+HindIII, SalI, SalI+HindIII, BglII, BglII+HindIII, PstI and PstI+HindIII. After digestion, the reaction mixtures were run on a 1% agarose gel and then blotted onto an Immobilon N™ membrane (Millipore Corporation) following the manufacturers instructions. The membrane was probed with the cloned A. oryzae PCR product isolated as a BamHI–EcoRI fragment and radio labelled with $^{32}$P. After stringent washes the membrane was subjected to autoradiography.

Genomic DNA from A. niger was digested with the following restriction enzymes: BglII, BamHI, BamHI+BglII, EcoRI, EcoRI+BglII, SalI, SalI+BglII, HindIII, HindIII+BglII, PstI and PstI+BglII. The Southern blot was made as described with A. oryzae, only the A. niger PCR product was used as probe.

1.4 Construction of genomic A. oryzae library

Southern analysis indicated that the A. oryzae PDI gene was located on a 6.8 kb BglII fragment. Genomic A. oryzae DNA was digested with BglII and fragments ranging from 5 kb to 8.5 kb were isolated from an agarose gel. Subcloning thereof and Southern analysis indicated that the A. oryzae PDI gene was located on a 2.3 kb BamHI, HindIII fragment. Genomic A. oryzae DNA was digested with BamHI and HindIII and fragments ranging from 1.9–3 kb were isolated from an agarose gel. This mixture of fragments was ligated to pUC19 digested with BamHI and HindIII. The ligation mixture was used to transform E. coli DH5αF'. The transformed E. coli cells were spread onto 10 agar plates using ampicillin selection.

1.5 Screening of the A. oryzae genomic library

The libraries were screened using the filter colony hybridization method described by Gergen et al. (Nucleic Acids Res. 7:2115–2136, 1979). The probe that was used for the Southern blot was also used for the colony hybridization. Positive clones were isolated and confirmed by sequence analysis using sequencing primers designed from the sequences of the PDI fragments. One of the plasmids containing the desired fragment was termed pCaHj 425.

1.6 Sequence of the gene

The gene was sequenced using the Taq DyeDeoxy™ Terminator cycle sequencing kit supplied by Applied Biosystems following the manufacturer's instructions. The sequence reactions were run on an Applied Biosystems 373A DNA sequencer and the data were evaluated using the Macintosh computer program SeqEd version 1.0 supplied by Applied Biosystems.

The sequence of the A. oryzae gene is shown in the appended SEQ ID No. 1.

The amino acid composition of the purified PDI obtained as described in Example 2 was in accordance with the composition deduced from the DNA-sequence shown in SEQ ID No. 1. From homology to other PDI genes and consensus splicing sequences a cDNA sequence as shown in SEQ ID no. 2 was suggested. The derived protein sequence is as shown in SEQ ID No. 3.

Example 2

Expression of truncated forms of the A. oryzae PDI gene 2.1 Construction of expression plasmids The PDI gene of A. oryzae was truncated at various positions by introduction stop codons. This was done by PCR amplification of the PDI gene using a 5' PCR primer harbouring a BamHI site at its 5' end and 8 different 3' primers corresponding to 8 different truncations each harbouring a HindIII site. The sequence of the 5' primer was:

5' TTCGGATCCACCATGCGGACTTTCGCACC 3' 5205.
(SEQ ID No. 15)

The sequences of the eight 3' primers were:

5' CCAAGCTTTAGAGATGCTTGTTGACAAGCTCCTG
GAGGAGCTCCCTGATAAGCTT 3' 5215.
(SEQ ID No. 16)

5' CCAAGCTTTAGACCATGTATGACACAATCGCCTCG
GTCTGACGAG 3' 5397.
(SEQ ID No. 17)

5' CCAAGCTTTAGACAGGGGACACAGCAGGTAG 3' 5895.
(SEQ ID No. 18)

5' CCAAGCTTTATGGGGTGACAGGGGACA 3' 5399.
(SEQ ID No. 19)

5' CCAAGCTTTAAGACGCGATATAACCAATAAC 3' 5894.
(SEQ ID No. 20)

5' CCAAGCTTTAAGTGGTGAATATATCATTGGC 3' 5893.
(SEQ ID No. 21)

5' CCAAGCTTAGTGTTTCTCGGCGATGAACTT 3' 6314.
(SEQ ID No. 22)

5' CCAAGCTTTACGCAGACTTGTCATCGCTAGT 3' 5204.
(SEQ ID No. 23)

Primer 5215 directed an extension of the PDI gene amino acid 1–115 with the sequence Leu-Ile-Arg-Glu-Leu-Leu-Gln-Glu-Leu-Val-Asn-Lys-His-Leu (SEQ ID NO:11); followed by a stop codon.

Primer 5397 introduced a stop codon after amino acid 131.

Primer 5895 introduced a stop codon after amino acid 141.

Primer 5399 introduced a stop codon after amino acid 143.

Primer 5894 introduced a stop codon after amino acid 163.

Primer 5893 introduced a stop codon after amino acid 174.

Primer 6314 introduced a stop codon after amino acid 281.

Primer 5204 introduced the mutation E511A (meaning substituting and a stop codon after amino acid 511.

The expression plasmids were constructed by PCR amplification using primer 5205 in combination with either 5215, 5397, 5895, 5399, 5894, 5893, 6314 or 5204 and pCaHj 425 as template using standard PCR conditions. The generated PCR fragments were digested with BamHI and HindIII and inserted into pMT 1560 (described in e.g. PCT/DK94/00138) digested with the same enzymes (See FIG. 3). The constructed plasmids were named pCaHj 432 (from primer 5215), pCaHj 433 (from primer 5397), PCaHj 441 (from primer 5895), pCaHj 434 (from primer 5399), pCaHj 440 (from primer 5894), pCaHj 439 (from primer 5893), pCaHj 445 (from primer 6314) and pCaHj 431 (from primer 5204).

2.2 Transformation of *A. oryzae* IFO 4177.

Each of the plasmids pCaHj 432, pCaHj 433, PCaHj 441, pCaHj 434, pCaHj 440, pCaHj 439, pCaHj 445 and pCaHj 431 were transformed into *A. oryzae* IFO 4177 by cotransformation with the amdS selection plasmid pToC 90 (described in WO91/17243) following the procedure described in the published EP patent application No. 238 023.

A number of transformants of each plasmid were evaluated.

2.3 Transformation of *A. niger* TSA 1.

Each of the plasmids PCaHj 441, pCaHj 434, pCaHj 440 and pCaHj 439 were transformed into *A. niger* TSA 1 by the same procedure as with *A. oryzae*.

A number of transformants of each plasmid were evaluated.

Example 3

Fermentation purification and characterization of the *Aspergillus oryzae* PDI truncations 3.1 *A. oryzae* IFO 4177 transformants.

Crude truncated PDI preparation was isolated from supernatants obtained by fermentation of the *A. oryzae* or *A. niger* pCaHj 432, pCaHj 433, PCaHj 441, pCaHj 434, pCaHj 440, pCaHj 439, pCaHj 445 or pCaHj 431 transformants in shake flasks containing YPM medium (1 liter: 5 g Difco Yeast extract, 10 g Difco peptone, 20 g maltose). The supernatant was recovered by filtration. The PDI truncation gene products were partially purified using a 1 ml HiTrap Q™ anion exchanger from Pharmacia LKB Biotechnology AB Uppsala, Sweden following the manufacturers instructions. Fractions were collected and analyzed by measuring the disulphide isomerase activity and by SDS PAGE.

The pCaHj 434 transformants secreted a protein of approx 14 kD (SDS PAGE) not present in supernatants of the untransformed strain. Enrichment of this protein by ion exchange was followed by increased disulphide isomerase activity. The approx. 14 kD band was blotted from an SDS Page gel and subjected to N-terminal amino acid sequence determination using an Applied Biosystems 473A protein sequencer. A sequence of 7 amino acids could unambiguously be determined as: Thr-Ala-Glu-Ala-Pro-Ser-Asp (SEQ ID NO:25). This sequence corresponds to residue 24–30 of the *A. oryzae* protein sequence. The size of the truncation expected from the amino acid sequence is thus 13.2 kD. So it can be concluded that the pCaHj 434 gene product is secreted to the supernatant, that it has the expected size and that it is catalytic active.

The pCaHj 441 transformants secreted a protein of the same size as the pCaHj 434 transformants. Also for this truncation enrichment of the protein was followed by increased disulphide isomerase activity demonstrating that the pCaHj 441 gene product is a catalytic active secreted protein.

The pCaHj 440 transformants secreted a protein of approx 16 kD not present in the untransformed strain. The expected size is 15.7 kD assuming the same N-terminal sequence as the pCaHj 434 product. Enrichment of the protein by ion exchange was followed by increased disulphide isomerase activity demonstrating that also the pCaHj 440 gene product is a catalytic active secreted protein.

The pCaHj 445 transformants secreted a protein of approx 30 kD not present in the untransformed strain. The expected size is 28.6 kD assuming the same N-terminal sequence as the pCaHj 434 product. Enrichment of the protein by ion exchange was followed by increased disulphide isomerase activity demonstrating that the pCaHj 440 gene product is a catalytic active secreted protein.

3.2 *A. niger* TSA 1 transformants.

Transformants of PCaHj 441, pCaHj 434, pCaHj 440 and pCaHj 439 were evaluated in the same way as the corresponding *A. oryzae* transformants with the exception that the N-terminal amino acid sequence was not determined for any of the proteins secreted by *A. niger*.

In all other aspects the same results were obtained with the *A. niger* transformants as with the *A. oryzae* transformants. However the fermentation yield of the truncations were generally lower in *A. niger* than in *A. oryzae*.

TABLE 1

(SEQ ID NOS: 26–32)

| | 1 | | | | | | 50 |
|---|---|---|---|---|---|---|---|
| Pdi_Mouse | . . . . . . . M L S | R A L L C L A L A W | A A R V G A D A L E | E E D N V L V L K K | S N F E E A L A A H | | |
| Pdi_Rat | . . . . . . . M L S | R A L L C L A L A W | A A R V G A D A L E | E E D N V L V L K K | S N F A E A L A A H | | |
| Pdi_Bovin | . . . . . . . M L R | R A L L C L A L T A | L F R A G A G A P D | E E D H V L V L H K | G N F D E A L A A H | | |
| Pdi_Human | . . . . . . . M L R | R A L L C L A V A A | L V R . . A D A P E | E E D H V L V L R K | S N F A E A L A A H | | |
| Pdi_Rabit | . . . . . . . M L R | R A V L C L A L A V | T A . G W A W A A E | E E D N V L V L K S | S N F A E E L A A H | | |
| Pdi_Chick | . . . . . . . . . . . | . . . . . . . . . . . | . . . . . . E P L E | E E D G V L V L R A | A N F E Q A L A A H | | |
| Pdi_Yeast | M K F S A G A V L S | W S S L L L A S S V | F A Q Q E A V A P E | D S A . V V K L A T | D S F N E Y I Q S H | | |

| | 51 | | | | | | 100 |
|---|---|---|---|---|---|---|---|
| Pdi_Mouse | K Y L L V E F Y A P | W C G H C K A L A P | E Y A K R A A K L K | A E G S E I R L A K | V D A T E E S D L A | | |
| Pdi_Rat | N Y L L V E F Y A P | W C G H C K A L A P | E Y A K A A A K L K | A E G S E I R L A K | V D A T E E S D L A | | |
| Pdi_Bovin | K Y L L V E F Y A P | W C G H C K A L A P | E Y A K A A G K L K | A E G S E I R L A K | V D A T E E S D L A | | |
| Pdi_Human | K Y L L V E F Y A P | W C G H C K A L A P | E Y A K A A G K L K | A E G S E I R L A K | V D A T E E S D L A | | |
| Pdi_Rabit | K H L L V E F Y A P | W C G H C K A L A P | E Y A K A A G K L K | A E G S D I R L A K | V D A T E E S D L A | | |
| Pdi_Chick | R H L L V E F Y A P | W C G H C K A L A P | E Y A K A A A Q L K | A E G S E I R L A K | V D A T E E A E L A | | |
| Pdi_Yeast | D L V L A E F F A P | W C G H C K N M A P | E Y V K A A E T L . | . V E K N I T L A Q | I D C T E N Q D L C | | |

TABLE 1-continued (SEQ ID NOS: 26–32)

```
           101                                                                                      150
Pdi_Mouse  QQYGVRGYPT  IKFFKNGDTA  SPKEYTAGRE  ADDIVNWLKK  RTGPAATTLS
Pdi_Rat    QQYGVRGYPT  IKFFKNGDTA  SPKEYTAGRE  ADDIVNWLKK  RTGPAATTLS
Pdi_Bovin  QQYGVRGYPT  IKFFKNGDTA  SPKEYTAGRE  ADDIVNWLKK  RTGPAASTLS
Pdi_Human  QQYGVRGYPT  IKFFRNGDTA  SPKEYTAGRE  ADDIVNWLKK  RTGPAATTLR
Pdi_Rabit  QQYGVRGYPT  IKFFKNGDTA  SPKEYTAGRE  ADDIVNWLKK  RTGPAATTLA
Pdi_Chick  QQFGVRGYPT  IKFFRNGDKA  APREYTAGRE  ADDIVSWLKK  RTGPAATTLT
Pdi_Yeast  MEHNIPGFPS  LKIFKNSDVN  NSIDYEGPRT  AEAIVQFMIK  QSQPAVAVVA 151                                                                                      200
Pdi_Mouse  DTAAAESLVD  SSEVTVIGFF  KDVESDSAKQ  FLLAAEAIDD  IPFGITSNSG
Pdi_Rat    DTAAAESLVD  SSEVTVIGFF  KDAGSDSAKQ  FLLAAEAVDD  IPFGITSNSD
Pdi_Bovin  DGAAAEALVE  SSEVAVIGFF  KDMESDSAKQ  FFLAAEVIDD  IPFGITSNSD
Pdi_Human  DGAAAESLVE  SSEVAVIGFF  KDVESDSAKQ  FLQAAEAIDD  IPFGITSNSD
Pdi_Rabit  DSAAAESLVE  SSEVAVIGFF  KDVESDAAKQ  FLLAAEATDD  IPFGLTASSD
Pdi_Chick  DAAAAETLVD  SSEVVVIGFF  KDVTSDAAKE  FLLAAESVDD  IPFGISSAD
Pdi_Yeast  DLPAYLANET  FVTPVIVQSG  KIDADFNATF  YSMANKHFND  YDFVSAENAD 201                                                                                      250
Pdi_Mouse  VFSKYQLDKD  GVVLFKKFDE  GR..NNFEGE  ITKEKLLD.F  IKHNQLPLVI
Pdi_Rat    VFSKYQLDKD  GVVLFKKFDE  GR..NNFEGE  ITKEKLLD.F  IKHNQLPLVI
Pdi_Bovin  VFSKYQLDKD  GVVLFKKFDE  GR..NNFEGE  VTKEKLLD.F  IKHNQLPLVI
Pdi_Human  VFSKYQLDKD  GVVLFKKFDE  GR..NNFEGE  VTKENLLD.F  IKHNQLPLVI
Pdi_Rabit  VFSRYQVHQD  GVVLFKKFDE  GR..NNFEGE  VTKEKLLD.F  IKHNQLPLVI
Pdi_Chick  VFSKYQLSQD  GVVLFKKFDE  GR..NNFEGD  LTKDNLLN.F  IKSNQLPLVI
Pdi_Yeast  ..DDFKL...  SIYLPSAMDE  PVVYNGKKAD  IADADVFEKW  LQVEALPYFG 251                                                                                      300
Pdi_Mouse  EFTEQTAPKI  FGGEIKTHIL  LFLPKSVSDY  DGKLSSFKRA  AEGF..KGKI
Pdi_Rat    EFTEQTAPKI  FGGEIKTHIL  LFLPKSVSDY  DGKLSNFKKA  AEGF..KGKI
Pdi_Bovin  EFTEQTAPKI  FGGIEKTHIL  LFLPKSVSDY  EGKLSNFKKA  AESF..KGKI
Pdi_Human  EFTEQTAPKI  FGGEIKTHIL  LFLPKSVSDY  DGKLSNFKTA  AESF..KGKI
Pdi_Rabit  EFTEQTAPKI  FGGEIKTHIL  LFLPRSAADH  DGKLSGFKQA  AEGF..KGKI
Pdi_Chick  EFTEQTAPKI  FGGEIKTHIL  LFLPKSVSDY  EGKLDNFKTA  AGNF..KGKI
Pdi_Yeast  EIDGSVFAQY  VESGLPLGYL  FY......ND  EEELEEYKPL  FTELAKKNRG 301                                                                                      350
Pdi_Mouse  LFIFIDSDHT  DNQRILEFFG  LKKEECPAVR  LITLEEEM..  .......TKY
Pdi_Rat    LFIFIDSDHT  DNQRILEFFG  LKKEECPAVR  LITLEEEM..  .......TKY
Pdi_Bovin  LFIFIDSDHT  DNQRILEFFG  LKKEECPAVR  LITLEEEM..  .......TKY
Pdi_Human  LFIFIDSDHT  DNQRILEFFG  LKKEECPAVR  LITLEEEM..  .......TKY
Pdi_Rabit  LFIFIDSDHA  DNQRILEFFG  LKKEECPAVR  LITLEEEM..  .......TKY
Pdi_Chick  LFIFIDSDHS  DNQRILEFFG  LKKEECPAVR  LITLEEEM..  .......TKY
Pdi_Yeast  LMNFVSIDAR  KFGRHAGNLN  M.DEQFPLFA  IHDMTEDLKY  GLPQLSEEAF 351                                                                                      400
Pdi_Mouse  KPESDELTAE  K..ITEFCHR  FLEGKIKPHL  MSQEVPEDWD  KQPVKVLVGA
Pdi_Rat    KPESDELTAE  K..ITQFCHH  FLEGKIKPHL  MSQELPEDWD  KQPVKVLVGK
Pdi_Bovin  KPESDELTAE  K..ITEFCHR  FLEGKIKPHL  MSQELPDDWD  KQPVKVLVGK
Pdi_Human  KPESEELTAE  R..ITEFCHR  FLEGKIKPHL  MSQERAGDWD  KQPVKVPVGK
Pdi_Rabit  KPESDELTAE  G..ITEFCQR  FLEGKIKPHL  MSQELPEDWD  RQPVKVLVGK
Pdi_Chick  KPESDDLTAD  K..IKEFCNK  FLEGKIKPHL  MSQDLPEDWD  KQPVKVLVGK
Pdi_Yeast  DELSDKIVLE  SKAIESLVKD  FLKGDASPIV  KSQEIFENQD  S.SVFQLVGK 401                                                                                      450
Pdi_Mouse  NFEEVAFDEK  KNVFVEFYAP  WCGHCKQLAP  IWDKLGETY.  KDHENIIIAK
Pdi_Rat    NFEEVAFDEK  KNVFVEFYAP  WCGHCKQLAP  IWDKLGETY.  KDHENIVIAK
Pdi_Bovin  NFEEVAFDEK  KNVFVEFYAP  WCGHCKQLAP  IWDKLGETY.  KDHENIVIAK
Pdi_Human  NFEDVAFDEK  KNVFVEFYAP  WCGHCKQLAP  IWDKLGETY.  KDHENIVIAK
Pdi_Rabit  NFEEVAFDEK  KNVFVEFYAP  WCGHCKQLAP  IWDKLGETY.  KEHQDIVIAK
Pdi_Chick  NFEEVAFDEN  KNVFVEFYAP  WCGHCKQLAP  IWDKLGETY.  RDHENIVIAK
Pdi_Yeast  NHDEIVNDPK  KDVLVLYYAP  WCGHCKRLAP  YTQELADTYA  NATSDVLIAK 451                                                                                      500
Pdi_Mouse  MDSTANEVEA  VKVHSFPTLK  FFPASADRTV  IDYNGERTLD  GFKKFLESGG
Pdi_Rat    MDSTANEVEA  VKVHSFPTLK  FFPASADRTV  IDYNGERTLD  GFKKFLESGG
Pdi_Bovin  MDSTANEVEA  VKVHSFPTLK  FFPASADRTV  IDYNGERTLD  GFKKFLESGG
Pdi_Human  MDSTANEVEA  VKVHSFPTLK  FFPASADRTV  IDYNGERTLD  GFKKFLESGG
Pdi_Rabit  MDSTANEVEA  VKVHSFPTLK  FFPAGPGRTV  IDYNGERTLD  GFKKFLESGG
Pdi_Chick  MDSTANEVEA  VKIHSFPTLK  FFPAGSGRNV  IDYNGERTLE  GFKKFLESGG
Pdi_Yeast  LDHTENDVRG  VVIEGYPTIV  LYPGGKKSES  VVYQGSRSLD  SLFDFIKENG
```

TABLE 1-continued (SEQ ID NOS: 26–32)

|  | 501 |  |  |  | 538 |
|---|---|---|---|---|---|
| Pdi_Mouse | QDGAGDDEDL | .DLEE..ALE | PDMEE..DDD | QKAVKDEL |  |
| Pdi_Rat | QDGAGDNDDL | .DLEE..ALE | PDMEE..DDD | QKAVKDEL |  |
| Pdi_Bovin | QDGAGDDDDL | EDLEE..AEE | PDLEE..DDD | QKAVKDEL |  |
| Pdi_Human | QDGAGDDDDL | EDLEE..AEE | PDMEE..DDD | QKAVKDEL |  |
| Pdi_Rabit | QDGAGDEDGL | EDLEE..AEE | PDLEE..DDD | QKAVRDEL |  |
| Pdi_Chick | QDGAAADDDL | EDLET..DEE | TDLEEGDDDE | QKIQKDEL |  |
| Pdi_Yeast | HFDVDGKALY | EEAQEKAAEE | ADADAELADE | EDAIHDEL |  |

TABLE 2

(SEQ ID NOS 33–38)

| Alfalfa | M-AKNVAIFG | LLFSLLLLVP | SQIFA----- | -------EES | STDAKE---- |
|---|---|---|---|---|---|
| Oryzae | MRTFAPWIL- | --SLLGASA- | --VAS----- | ------AADA | TAEAPS---- |
| Yeast | MKFSAGAVLS | WSSLLLASS- | --VFA----- | ------QQEA | VAPEDS---- |
| Bovine | M-LRRA-LLC | --LALTALF- | --RAG----- | -------AGA | PDEEDH---- |
| Rat | M-LSRA-LLC | --LALAWAA- | --RVG----- | -------ADA | LEEEDN---- |
| Mouse | MKLRKAWLLV | LLLALTQLLA | AASAGDAQED | TSDTENATEE | EEEEDDDDLE |

|  |  |  | ---FVL---- |  |  |
|---|---|---|---|---|---|
|  |  |  | ---DVV---- |  |  |
|  |  |  | ---AVV---- |  |  |
|  |  |  | ----VL---- |  |  |
|  |  |  | ----VL---- |  |  |
| VKEENGVWVL | NDGNFDNFVA | DKDTVLLEFY | APWCGHCKQF | APEYEKIAST |

|  |  |  | ----TLDNT- |  |
|---|---|---|---|---|
|  |  |  | ----SLTGD- |  |
|  |  |  | ----KLATD- |  |
|  |  |  | ----VLHKG- |  |
|  |  |  | ----VLKKS- |  |
| LKDNDPPIAV | AKIDATSASM | LASKFDVSGY | PTIKILKKGQ | AVDYDGSRTQ |

|  |  | -------NF | HDTVKKHDFI | VVEFYAPWCG |
|---|---|---|---|---|
|  |  | -------TF | ETFVKEHDLV | LAEFFAPWCG |
|  |  | -------SF | NEYIQSHDLV | LAEFFAPWCG |
|  |  | -------NF | DEALAAHKYL | LVEFYAPWCG |
|  |  | -------NF | AEPAAHNYLL | VEFY-APWCG |
| EEIVAKVREV | SQPDWTPPPE | VTLSLTKDNF | DDVVNNADII | LVEFYAPWCG |

| HCKKLAPEYE | KAASILSTHE | PPVVLAKVDA | NEEHNKDLAS | ENDVKGFPTI |
|---|---|---|---|---|
| HCKALAPKYE | QAATELKEKN | IPL--VKVDC | TEEEA--LCR | DQGVEGYPTL |
| HCKNMAPEYV | KAAETLVEKN | ITL--AQIDC | TENQD--LCM | EHNIPGFPSL |
| HCKALAPEYA | KAAGKLKAEG | SEIRLAKVDA | TEESD--LAQ | QYGVRGYPTI |
| HCKALAPEYA | KAAAKLKAEG | SEIRLAKVDA | TEESD--LAQ | QYGVRGYPTI |
| HCKKLAPEYE | KAAKELSKRS | PPIPLAKVDA | TEQTD--LAK | RFDVSGYPTL |

| KIFRNGG-KN | IQEYKGPREA | EGIVEYLKKQ | SGPAS-TEIK | SADDATAFVG |
|---|---|---|---|---|
| KIFRGLDAVK | P--YQGARQT | EAIVSYMVKQ | SLPAV-SPVT | PENLEE-IKT |
| KIFKNRDVNN | SIDYEGPRTA | EAIVQFMIKQ | SQPAV-AVVA | DLPAYL-ANE |
| KFFKNGDTAS | PKEYTAGREA | DDIVNWLKKR | TGPAA-STLS | DGAAAEALVE |
| KFFKNGDTAS | PKEYTAGREA | DDIVNWLKKR | TGPAA-TTLS | DTAAAESLVD |
| KIFRKG---R | PFDYNGPREK | YGIVDYMIEQ | SGPPSKEILT | LKQVQEFLKD |

| DNKVVIVGVF | PKFSGEEYDN | FIALAEKLRS | DYDFAHTLNA | KHLPKGDSSV |
|---|---|---|---|---|
| MDKIVVIGYI | ASDDQTANDI | FTTFAESQRD | NYLFAATSDA | SI--AKAEGV |
| TFVTPVIVQS | GKIDADFNAT | FYSMANKHFN | DYDFVSAENA | DD--DFKLSI |
| SSEVAVIGFF | KDMESDSAKQ | FFLAAEVI-D | DIPFGITSNS | DV--FSKYQL |
| SSEVTVIGFF | KDAGSDSAKQ | FLLAAEAV-D | DIPFGITSNS | DV--FSKYQL |
| GDDVVIIGLF | QGDGDPAYLQ | YQDAANNLRE | DYKFHHTFSP | EIAKFLKVSL |

| SGPVVRLFKP | FDELFVDS-- | -KDFNVEALE | KFIEESSTPI | VTVFNNEPSN |
|---|---|---|---|---|
| KQPSIVLYKD | FDEKKATYDG | EIEQDALLSW | VKTASTPLVG | ELGPETYSGY |
| YLPSAM--DE | PVVYNGKKAD | IADADVFEKW | LQVEALPYFG | EIDGSVFAQY |
| DKDGVVLFKK | FD---EGR-- | -NNFEGEVTK | EKLLDFIKHN | QLPLVIEFTE |
| DKDGVVLFKK | FD---EGR-- | -NNFEGEITK | EKLLDFIKHN | QLPLVIEFTE |
| GKLVLTHPEK | FQSKYEPRFH | VMDVQGSTEA | SAIKDYVVKH | ALPLVGHRKT |

TABLE 2-continued (SEQ ID NOS 33-38)

| | | | | | |
|---|---|---|---|---|---|
| HPFVVKFFNS | PNAKAMLFIN | FTTEGAESFK | TKYHEVAEQY | KQQGV-SFLV |
| ITAGIPLAYI | FAETKEEREQ | FTEEFKFIAE | KHKGSINIVT | IDAKLYGAHA |
| VESGLPLGYL | FYNDEEELEE | YKPLFTELAK | KNRGLMNFVS | IDARKFGRHA |
| QTAPKIFGGE | IKTHILLFLP | KSVSDYEGKL | SNFKKAAESF | KGKILFIFID |
| QTAPKIFGGE | IKTHILLFLP | KSVSDYDGKL | SNFKKAAEGF | KGKILFIFID |
| SNDAKRYSKR | PLVVVYYSVD | FSFDYRAATQ | FWRNKVLEVA | KDFPEYTFAI |
| | | | | |
| GDVESSQGAF | QYFGLKEEQV | PLI--IIQHN | DGKKFFKPN- | --LELDQLPT |
| GNLNLDPSKF | PAFAIQDPEK | NAKY------ | --PYDQSKE- | --VKAKDIGK |
| GNLNMK-EQF | PLFAIHDMTE | DLKYGLPQLS | EEAFDELSDK | IVLESKAIES |
| SDHTDNQRIL | EFFGLKKEEC | PAVR-LITLE | EEMTKYKPES | DELTAEKITE |
| SDHTDNQRIL | EFFGLKKEEC | PAVR-LITLE | EEMTKYKPES | DELTAEKITQ |
| ADEEDYATEV | KDLGL-SESG | EDVN-AAILD | ESGKKFAMEP | EEFDSDTLRE |
| | | | | |
| WLKAYKDGKV | EPFVKSEPIP | ETNN-EPVKV | VVGQTLEDVV | FKSGKNVLIE |
| FIQDVLDDKV | EPSIKSEAIP | ETQE-GPVTV | VVAHSYKDLV | LDNEKDVLLE |
| LVKDFLKGDA | SPIVKSQEIF | ENQD-SSVFQ | LVGKNHDEIV | NDPKKDVLVL |
| FCHRFLEGKI | KPHLMSQELP | DDWDKQPVKV | LVGKNFEEVA | FDEKKNVFVE |
| FCHHFLEGKI | KPHLMSQELP | EDWDKQPVKV | LVGKNFEEVA | FDEKKNVFVE |
| FVTAFKKGKL | KPVIKSQPVP | KN-NKGPVKV | VVGKTFDAIV | MDPKKDVLIE |
| | | | | |
| FYAPWCGHCK | QLAPILDEVA | VSFQS-DADV | VIAKLDATAN | DIPTDTFDVQ |
| FYAPWCGHCK | ALAPKYEELA | SLYKD-IPEV | TIAKIDATAN | DV--PD-SIT |
| YYAPWCGHCK | RLAPTYQELA | DTYANATSDV | LIAKLDHTEN | DV--RGVVIE |
| FYAPWCGHCK | QLAPIWDKLG | ETYKD-HENI | VIAKMDSTAN | EV--EAVKVH |
| FYAPWCGHCK | QLAPIWDKLG | ETYKD-HENI | VIAKMDSTAN | EV--EAVKVH |
| FYAPWCGHCK | QLEPIYTSLG | KKYKG-QKDL | VIAKMDATAN | DITNDQYKVE |
| | | | | |
| GYPTLYFRSA | SGK--LSQYD | GGRTKEDIIE | FIE------K | NKDKTGAAHQ |
| GFPTIKLFAA | GAKDSPVEYE | GSRTVEDLAN | FVK------E | NGKHKVDALE |
| GYPTIVLYPG | GKKSESVVYQ | GSRSLDSLFD | FIK------E | NGHFDVDGKA |
| SFPTLKFFPA | SADRTVIDYN | GERTLDGFKK | FLESGGQDGA | GDDDDLEDLE |
| SFPTLKFFPA | SADRTVIDYN | GERTLDGFKK | FLESGRQDGA | GDNDDLDLEE |
| GFPTIYFAPS | GDKKNPI--- | ---------K | F--------E | GGNRDLEHLS |
| | | | | |
| EVEQPKAAAQ | PE-------- | ---------- | AEQPKDEL | |
| VDPKKEQESG | DATETRAASD | ETETPAATSD | DKSEHDEL | |
| LYEEAQEKAA | EEAEADAEAE | ADADAELADE | EDAIHDEL | |
| EAEEPDLEED | DD-------- | ---------- | QKAVKDEL | |
| ALE-PDMEED | DD-------- | ---------- | QKAVKDEL | |
| KF--ID-EHA | TK-------- | ---------- | RSRTKEEL | |

REFERENCES CITED IN THE SPECIFICATION

Sambrook, J., Fritsch, E. F. & Maniatis, T. 1989. Molecular Cloning: A Laboratory Manual. 2. edition. Cold Spring Harbor Lab., Cold Spring Harbor, N.Y.

U.S. Pat. No. 4,683,202

Hudson et al, 1989, Practical Immunology, Third edition, Blackwell Scientific Publications.

Beaucage and Caruthers, 1981, Tetrahedron Letters 22, 1981, pp. 1859–1869

Matthes et al., 1984, The EMBO J. 3, 1984, pp. 801–805

R. K. Saiki et al., 1988, Science 239, pp. 487–491

WO 91/17243

EP 238 023

Malardier et al. Gene 78 (1989), pp. 147–156

Woodcock et al., Nucleic Acids Res. (1989) 17:3469–3478

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
        ( A ) LENGTH: 1953 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (  i i i  ) ANTI-SENSE: NO (  v i  ) ORIGINAL SOURCE:
    (  A  ) ORGANISM: Aspergillus oryzae
    (  B  ) STRAIN: IFO 4177

(  i x  ) FEATURE:
    (  A  ) NAME/KEY: CDS
    (  B  ) LOCATION: join(71..445, 503..880, 962..1402,
        1479..1829)

(  x i  ) SEQUENCE DESCRIPTION: SEQ ID NO: 1:

```
CCCTGCTGTC  CCCATAGACA  GTACACGT  CATCCTTTGA  TATTGTCACA  CTTGACAAAT              60

TCCCGACACC  ATG  CGG  ACT  TTC  GCA  CCT  TGG  ATC  TTG  AGC  CTT  CTA  GGG      109
            Met  Arg  Thr  Phe  Ala  Pro  Trp  Ile  Leu  Ser  Leu  Leu  Gly
             1                5                           10

GCT  TCT  GCT  GTA  GCT  TCT  GCT  GCC  GAT  GCG  ACT  GCC  GAA  GCT  CCC  TCC   157
Ala  Ser  Ala  Val  Ala  Ser  Ala  Ala  Asp  Ala  Thr  Ala  Glu  Ala  Pro  Ser
          15                      20                      25

GAT  GTG  GTC  TCG  CTC  ACC  GGG  GAC  ACA  TTC  GAA  ACT  TTC  GTC  AAG  GAG   205
Asp  Val  Val  Ser  Leu  Thr  Gly  Asp  Thr  Phe  Glu  Thr  Phe  Val  Lys  Glu
 30                      35                      40                         45

CAT  GAC  CTA  GTT  TTG  GCC  GAG  TTT  TTT  GCT  CCC  TGG  TGT  GGC  CAT  TGC   253
His  Asp  Leu  Val  Leu  Ala  Glu  Phe  Phe  Ala  Pro  Trp  Cys  Gly  His  Cys
               50                           55                           60

AAG  GCT  CTC  GCT  CCG  AAA  TAC  GAG  CAG  GCC  GCC  ACT  GAG  TTA  AAG  GAA   301
Lys  Ala  Leu  Ala  Pro  Lys  Tyr  Glu  Gln  Ala  Ala  Thr  Glu  Leu  Lys  Glu
               65                      70                      75

AAG  AAC  ATT  CCG  CTG  GTC  AAG  GTT  GAT  TGC  ACC  GAG  GAA  GAG  GCT  CTT   349
Lys  Asn  Ile  Pro  Leu  Val  Lys  Val  Asp  Cys  Thr  Glu  Glu  Glu  Ala  Leu
               80                      85                      90

TGT  AGG  GAC  CAA  GGT  GTT  GAA  GGT  TAC  CCC  ACG  CTG  AAG  ATT  TTC  CGT   397
Cys  Arg  Asp  Gln  Gly  Val  Glu  Gly  Tyr  Pro  Thr  Leu  Lys  Ile  Phe  Arg
      95                     100                     105

GGC  CTT  GAC  GCT  GTT  AAG  CCT  TAT  CAG  GGA  GCT  CGT  CAG  ACC  GAG  GCG   445
Gly  Leu  Asp  Ala  Val  Lys  Pro  Tyr  Gln  Gly  Ala  Arg  Gln  Thr  Glu  Ala
110                     115                     120                     125

GTAAGTGTCA  CCTGTTTGTT  AGCCTTGCTC  AAATAATATT  GACCGCTAGT  ATCATAG              502

ATT  GTT  TCA  TAC  ATG  GTC  AAG  CAG  TCA  CTA  CCT  GCT  GTG  TCC  CCT  GTC   550
Ile  Val  Ser  Tyr  Met  Val  Lys  Gln  Ser  Leu  Pro  Ala  Val  Ser  Pro  Val
               130                     135                     140

ACC  CCA  GAA  AAC  CTC  GAA  GAG  ATC  AAG  ACT  ATG  GAC  AAG  ATT  GTC  GTT   598
Thr  Pro  Glu  Asn  Leu  Glu  Glu  Ile  Lys  Thr  Met  Asp  Lys  Ile  Val  Val
               145                     150                     155

ATT  GGT  TAT  ATC  GCG  TCT  GAC  GAC  CAG  ACT  GCC  AAT  GAT  ATA  TTC  ACC   646
Ile  Gly  Tyr  Ile  Ala  Ser  Asp  Asp  Gln  Thr  Ala  Asn  Asp  Ile  Phe  Thr
               160                     165                     170

ACT  TTT  GCC  GAG  TCA  CAG  AGA  GAC  AAC  TAC  CTC  TTC  GCC  GCC  ACA  AGT   694
Thr  Phe  Ala  Glu  Ser  Gln  Arg  Asp  Asn  Tyr  Leu  Phe  Ala  Ala  Thr  Ser
     175                     180                     185

GAT  GCA  TCG  ATC  GCT  AAG  GCA  GAA  GGT  GTT  AAG  CAA  CCT  TCG  ATT  GTT   742
Asp  Ala  Ser  Ile  Ala  Lys  Ala  Glu  Gly  Val  Lys  Gln  Pro  Ser  Ile  Val
190                     195                     200                     205

CTC  TAT  AAA  GAC  TTC  GAT  GAA  AAG  AAA  GCT  ACT  TAT  GAT  GGA  GAG  ATT   790
Leu  Tyr  Lys  Asp  Phe  Asp  Glu  Lys  Lys  Ala  Thr  Tyr  Asp  Gly  Glu  Ile
               210                     215                     220

GAA  CAG  GAT  GCC  CTC  CTC  AGT  TGG  GTC  AAG  ACT  GCC  AGT  ACC  CCC  TTG   838
Glu  Gln  Asp  Ala  Leu  Leu  Ser  Trp  Val  Lys  Thr  Ala  Ser  Thr  Pro  Leu
               225                     230                     235

GTG  GGC  GAG  CTG  GGC  CCA  GAG  ACT  TAC  TCC  GGA  TAT  ATA  ACG             880
Val  Gly  Glu  Leu  Gly  Pro  Glu  Thr  Tyr  Ser  Gly  Tyr  Ile  Thr
               240                     245                     250
```

```
GTATGTCACA AGACACAATC TCAATATCGC TTCACAACGT TTAGTAAATA ATCATGAGTT         940

TCTGACATGG GTTTGGTTAA G GCT GGC ATT CCA CTG GCG TAC ATT TTC GCC         991
                         Ala Gly Ile Pro Leu Ala Tyr Ile Phe Ala
                                     255                     260

GAA ACC AAA GAA GAG CGT GAG CAG TTC ACC GAG GAG TTC AAG TTC ATC        1039
Glu Thr Lys Glu Glu Arg Glu Gln Phe Thr Glu Glu Phe Lys Phe Ile
            265             270                 275

GCC GAG AAA CAC AAG GGT TCC ATC AAT ATT GTC ACC ATT GAC GCC AAG        1087
Ala Glu Lys His Lys Gly Ser Ile Asn Ile Val Thr Ile Asp Ala Lys
            280             285                 290

TTG TAC GGC GCT CAT GCA GGC AAT CTC AAC CTT GAC CCC TCC AAG TTC        1135
Leu Tyr Gly Ala His Ala Gly Asn Leu Asn Leu Asp Pro Ser Lys Phe
    295             300             305

CCT GCA TTC GCT ATT CAA GAC CCT GAA AAG AAC GCC AAG TAT CCT TAT        1183
Pro Ala Phe Ala Ile Gln Asp Pro Glu Lys Asn Ala Lys Tyr Pro Tyr
310             315             320                 325

GAC CAG TCG AAG GAA GTC AAG GCC AAG GAT ATC GGT AAA TTC ATC CAA        1231
Asp Gln Ser Lys Glu Val Lys Ala Lys Asp Ile Gly Lys Phe Ile Gln
                330             335                 340

GAC GTT CTT GAT GAT AAA GTA GAG CCA AGC ATT AAG TCT GAG GCT ATT        1279
Asp Val Leu Asp Asp Lys Val Glu Pro Ser Ile Lys Ser Glu Ala Ile
            345             350                 355

CCT GAG ACT CAG GAA GGT CCT GTT ACT GTT GTT GTC GCG CAT TCC TAT        1327
Pro Glu Thr Gln Glu Gly Pro Val Thr Val Val Val Ala His Ser Tyr
            360             365                 370

AAG GAT CTC GTC CTT GAC AAC GAG AAG GAC GTC CTT CTC GAA TTT TAT        1375
Lys Asp Leu Val Leu Asp Asn Glu Lys Asp Val Leu Leu Glu Phe Tyr
    375             380                 385

GCG CCA TGG TGC GGA CAC TGC AAG GCC     GTAAGTTTC  CCCCTCTTTC         1422
Ala Pro Trp Cys Gly His Cys Lys Ala
390             395

TCTACAACGA ATTATATCCA CTCTCGCTTG CGAATACCTA ATTAAACCTT GAATAG          1478

CTT GCC CCG AAG TAC GAG GAA CTT GCA AGC CTT TAC AAG GAT ATT CCT        1526
Leu Ala Pro Lys Tyr Glu Glu Leu Ala Ser Leu Tyr Lys Asp Ile Pro
    400             405                 410

GAA GTT ACC ATC GCC AAA ATT GAC GCA ACG GCC AAC GAT GTC CCC GAC        1574
Glu Val Thr Ile Ala Lys Ile Asp Ala Thr Ala Asn Asp Val Pro Asp
415             420             425                 430

TCC ATT ACA GGA TTT CCT ACT ATT AAG CTC TTC GCT GCC GGC GCC AAG        1622
Ser Ile Thr Gly Phe Pro Thr Ile Lys Leu Phe Ala Ala Gly Ala Lys
                435             440                 445

GAC TCC CCA GTT GAA TAT GAA GGC TCT CGC ACG GTG GAG GAC CTC GCC        1670
Asp Ser Pro Val Glu Tyr Glu Gly Ser Arg Thr Val Glu Asp Leu Ala
            450             455                 460

AAC TTC GTC AAG GAG AAT GGC AAG CAC AAG GTC GAT GCT CTT GAA GTT        1718
Asn Phe Val Lys Glu Asn Gly Lys His Lys Val Asp Ala Leu Glu Val
        465             470                 475

GAT CCG AAG AAA GAA CAG GAG AGT GGC GAT GCC ACC GAG ACT CGG GCC        1766
Asp Pro Lys Lys Glu Gln Glu Ser Gly Asp Ala Thr Glu Thr Arg Ala
        480             485                 490

GCC TCT GAC GAG ACC GAA ACT CCT GCT GCT ACT AGC GAT GAC AAG TCT        1814
Ala Ser Asp Glu Thr Glu Thr Pro Ala Ala Thr Ser Asp Asp Lys Ser
495             500             505                 510

GAG CAT GAT GAA TTG TAAATTTCAT TTGGCCTGAT AGTTTGATCC ATATTTATGT        1869
Glu His Asp Glu Leu
                515

GAATTCTTGT ATTCTACCAG CAGTTTGAGC AATCGCAGCT ACTTCCGGCT TAGGAAACTG      1929

TTGTTCTATC CTAGTGGGAA GCTT                                             1953
```

( 2 ) INFORMATION FOR SEQ ID NO: 2:

( i ) SEQUENCE CHARACTERISTICS:
        ( A ) LENGTH: 1547 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Aspergillus oryzae
        ( B ) STRAIN: IFO 4177

( i x ) FEATURE:
        ( A ) NAME/KEY: CDS
        ( B ) LOCATION: 1..1547

( x i ) SEQUENCE DESCRIPTION: SEQ ID NO: 2:

```
ATG CGG ACT TTC GCA CCT TGG ATC TTG AGC CTT CTA GGG GCT TCT GCT        48
Met Arg Thr Phe Ala Pro Trp Ile Leu Ser Leu Leu Gly Ala Ser Ala
 1               5                  10                  15

GTA GCT TCT GCT GCC GAT GCG ACT GCC GAA GCT CCC TCC GAT GTG GTC        96
Val Ala Ser Ala Ala Asp Ala Thr Ala Glu Ala Pro Ser Asp Val Val
                20                  25                  30

TCG CTC ACC GGG GAC ACA TTC GAA ACT TTC GTC AAG GAG CAT GAC CTA       144
Ser Leu Thr Gly Asp Thr Phe Glu Thr Phe Val Lys Glu His Asp Leu
         35                  40                  45

GTT TTG GCC GAG TTT TTT GCT CCC TGG TGT GGC CAT TGC AAG GCT CTC       192
Val Leu Ala Glu Phe Phe Ala Pro Trp Cys Gly His Cys Lys Ala Leu
     50                  55                  60

GCT CCG AAA TAC GAG CAG GCC GCC ACT GAG TTA AAG GAA AAG AAC ATT       240
Ala Pro Lys Tyr Glu Gln Ala Ala Thr Glu Leu Lys Glu Lys Asn Ile
 65                  70                  75                  80

CCG CTG GTC AAG GTT GAT TGC ACC GAG GAA GAG GCT CTT TGT AGG GAC       288
Pro Leu Val Lys Val Asp Cys Thr Glu Glu Glu Ala Leu Cys Arg Asp
                 85                  90                  95

CAA GGT GTT GAA GGT TAC CCC ACG CTG AAG ATT TTC CGT GGC CTT GAC       336
Gln Gly Val Glu Gly Tyr Pro Thr Leu Lys Ile Phe Arg Gly Leu Asp
                100                 105                 110

GCT GTT AAG CCT TAT CAG GGA GCT CGT CAG ACC GAG GCG ATT GTT TCA       384
Ala Val Lys Pro Tyr Gln Gly Ala Arg Gln Thr Glu Ala Ile Val Ser
            115                 120                 125

TAC ATG GTC AAG CAG TCA CTA CCT GCT GTG TCC CCT GTC ACC CCA GAA       432
Tyr Met Val Lys Gln Ser Leu Pro Ala Val Ser Pro Val Thr Pro Glu
        130                 135                 140

AAC CTC GAA GAG ATC AAG ACT ATG GAC AAG ATT GTC GTT ATT GGT TAT       480
Asn Leu Glu Glu Ile Lys Thr Met Asp Lys Ile Val Val Ile Gly Tyr
145                 150                 155                 160

ATC GCG TCT GAC GAC CAG ACT GCC AAT GAT ATA TTC ACC ACT TTT GCC       528
Ile Ala Ser Asp Asp Gln Thr Ala Asn Asp Ile Phe Thr Thr Phe Ala
                165                 170                 175

GAG TCA CAG AGA GAC AAC TAC CTC TTC GCC GCC ACA AGT GAT GCA TCG       576
Glu Ser Gln Arg Asp Asn Tyr Leu Phe Ala Ala Thr Ser Asp Ala Ser
            180                 185                 190

ATC GCT AAG GCA GAA GGT GTT AAG CAA CCT TCG ATT GTT CTC TAT AAA       624
Ile Ala Lys Ala Glu Gly Val Lys Gln Pro Ser Ile Val Leu Tyr Lys
        195                 200                 205

GAC TTC GAT GAA AAG AAA GCT ACT TAT GAT GGA GAG ATT GAA CAG GAT       672
Asp Phe Asp Glu Lys Lys Ala Thr Tyr Asp Gly Glu Ile Glu Gln Asp
```

```
            210                           215                          220
GCC  CTC  CTC  AGT  TGG  GTC  AAG  ACT  GCC  AGT  ACC  CCC  TTG  GTG  GGC  GAG      720
Ala  Leu  Leu  Ser  Trp  Val  Lys  Thr  Ala  Ser  Thr  Pro  Leu  Val  Gly  Glu
225                      230                      235                      240

CTG  GGC  CCA  GAG  ACT  TAC  TCC  GGA  TAT  ATA  ACG  GCT  GGC  ATT  CCA  CTG      768
Leu  Gly  Pro  Glu  Thr  Tyr  Ser  Gly  Tyr  Ile  Thr  Ala  Gly  Ile  Pro  Leu
                    245                      250                      255

GCG  TAC  ATT  TTC  GCC  GAA  ACC  AAA  GAA  GAG  CGT  GAG  CAG  TTC  ACC  GAG      816
Ala  Tyr  Ile  Phe  Ala  Glu  Thr  Lys  Glu  Glu  Arg  Glu  Gln  Phe  Thr  Glu
               260                      265                      270

GAG  TTC  AAG  TTC  ATC  GCC  GAG  AAA  CAC  AAG  GGT  TCC  ATC  AAT  ATT  GTC      864
Glu  Phe  Lys  Phe  Ile  Ala  Glu  Lys  His  Lys  Gly  Ser  Ile  Asn  Ile  Val
          275                      280                      285

ACC  ATT  GAC  GCC  AAG  TTG  TAC  GGC  GCT  CAT  GCA  GGC  AAT  CTC  AAC  CTT      912
Thr  Ile  Asp  Ala  Lys  Leu  Tyr  Gly  Ala  His  Ala  Gly  Asn  Leu  Asn  Leu
     290                      295                      300

GAC  CCC  TCC  AAG  TTC  CCT  GCA  TTC  GCT  ATT  CAA  GAC  CCT  GAA  AAG  AAC      960
Asp  Pro  Ser  Lys  Phe  Pro  Ala  Phe  Ala  Ile  Gln  Asp  Pro  Glu  Lys  Asn
305                      310                      315                      320

GCC  AAG  TAT  CCT  TAT  GAC  CAG  TCG  AAG  GAA  GTC  AAG  GCC  AAG  GAT  ATC     1008
Ala  Lys  Tyr  Pro  Tyr  Asp  Gln  Ser  Lys  Glu  Val  Lys  Ala  Lys  Asp  Ile
                    325                      330                      335

GGT  AAA  TTC  ATC  CAA  GAC  GTT  CTT  GAT  GAT  AAA  GTA  GAG  CCA  AGC  ATT     1056
Gly  Lys  Phe  Ile  Gln  Asp  Val  Leu  Asp  Asp  Lys  Val  Glu  Pro  Ser  Ile
               340                      345                      350

AAG  TCT  GAG  GCT  ATT  CCT  GAG  ACT  CAG  GAA  GGT  CCT  GTT  ACT  GTT  GTT     1104
Lys  Ser  Glu  Ala  Ile  Pro  Glu  Thr  Gln  Glu  Gly  Pro  Val  Thr  Val  Val
          355                      360                      365

GTC  GCG  CAT  TCC  TAT  AAG  GAT  CTC  GTC  CTT  GAC  AAC  GAG  AAG  GAC  GTC     1152
Val  Ala  His  Ser  Tyr  Lys  Asp  Leu  Val  Leu  Asp  Asn  Glu  Lys  Asp  Val
     370                      375                      380

CTT  CTC  GAA  TTT  TAT  GCG  CCA  TGG  TGC  GGA  CAC  TGC  AAG  GCC  CTT  GCC     1200
Leu  Leu  Glu  Phe  Tyr  Ala  Pro  Trp  Cys  Gly  His  Cys  Lys  Ala  Leu  Ala
385                      390                      395                      400

CCG  AAG  TAC  GAG  GAA  CTT  GCA  AGC  CTT  TAC  AAG  GAT  ATT  CCT  GAA  GTT     1248
Pro  Lys  Tyr  Glu  Glu  Leu  Ala  Ser  Leu  Tyr  Lys  Asp  Ile  Pro  Glu  Val
                    405                      410                      415

ACC  ATC  GCC  AAA  ATT  GAC  GCA  ACG  GCC  AAC  GAT  GTC  CCC  GAC  TCC  ATT     1296
Thr  Ile  Ala  Lys  Ile  Asp  Ala  Thr  Ala  Asn  Asp  Val  Pro  Asp  Ser  Ile
               420                      425                      430

ACA  GGA  TTT  CCT  ACT  ATT  AAG  CTC  TTC  GCT  GCC  GGC  GCC  AAG  GAC  TCC     1344
Thr  Gly  Phe  Pro  Thr  Ile  Lys  Leu  Phe  Ala  Ala  Gly  Ala  Lys  Asp  Ser
          435                      440                      445

CCA  GTT  GAA  TAT  GAA  GGC  TCT  CGC  ACG  GTG  GAG  GAC  CTC  GCC  AAC  TTC     1392
Pro  Val  Glu  Tyr  Glu  Gly  Ser  Arg  Thr  Val  Glu  Asp  Leu  Ala  Asn  Phe
     450                      455                      460

GTC  AAG  GAG  AAT  GGC  AAG  CAC  AAG  GTC  GAT  GCT  CTT  GAA  GTT  GAT  CCG     1440
Val  Lys  Glu  Asn  Gly  Lys  His  Lys  Val  Asp  Ala  Leu  Glu  Val  Asp  Pro
465                      470                      475                      480

AAG  AAA  GAA  CAG  GAG  AGT  GGC  GAT  GCC  ACC  GAG  ACT  CGG  GCC  GCC  TCT     1488
Lys  Lys  Glu  Gln  Glu  Ser  Gly  Asp  Ala  Thr  Glu  Thr  Arg  Ala  Ala  Ser
                    485                      490                      495

GAC  GAG  ACC  GAA  ACT  CCT  GCT  GCT  ACT  AGC  GAT  GAC  AAG  TCT  GAG  CAT     1536
Asp  Glu  Thr  Glu  Thr  Pro  Ala  Ala  Thr  Ser  Asp  Asp  Lys  Ser  Glu  His
               500                      505                      510

GAT  GAA  TTG  TA                                                                   1547
Asp  Glu  Leu
          515
```

( 2 ) INFORMATION FOR SEQ ID NO: 3:

(i) SEQUENCE CHARACTERISTICS:
   (A) LENGTH: 515 amino acids
   (B) TYPE: amino acid
   (D) TOPOLOGY: linear (ii) MOLECULE TYPE: protein (xi) SEQUENCE DESCRIPTION: SEQ ID NO: 3:

```
Met Arg Thr Phe Ala Pro Trp Ile Leu Ser Leu Leu Gly Ala Ser Ala
 1               5                  10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
            35                  40                  45

Val Leu Ala Glu Phe Phe Ala Pro Trp Cys Gly His Cys Lys Ala Leu
        50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
                100                 105                 110

Ala Val Lys Pro Tyr Gln Gly Ala Arg Gln Thr Glu Ala Ile Val Ser
            115                 120                 125

Tyr Met Val Lys Gln Ser Leu Pro Ala Val Ser Pro Val Thr Pro Glu
    130                 135                 140

Asn Leu Glu Glu Ile Lys Thr Met Asp Lys Ile Val Val Ile Gly Tyr
145                 150                 155                 160

Ile Ala Ser Asp Asp Gln Thr Ala Asn Asp Ile Phe Thr Thr Phe Ala
                165                 170                 175

Glu Ser Gln Arg Asp Asn Tyr Leu Phe Ala Ala Thr Ser Asp Ala Ser
            180                 185                 190

Ile Ala Lys Ala Glu Gly Val Lys Gln Pro Ser Ile Val Leu Tyr Lys
        195                 200                 205

Asp Phe Asp Glu Lys Lys Ala Thr Tyr Asp Gly Glu Ile Glu Gln Asp
    210                 215                 220

Ala Leu Leu Ser Trp Val Lys Thr Ala Ser Thr Pro Leu Val Gly Glu
225                 230                 235                 240

Leu Gly Pro Glu Thr Tyr Ser Gly Tyr Ile Thr Ala Gly Ile Pro Leu
                245                 250                 255

Ala Tyr Ile Phe Ala Glu Thr Lys Glu Glu Arg Glu Gln Phe Thr Glu
            260                 265                 270

Glu Phe Lys Phe Ile Ala Glu Lys His Lys Gly Ser Ile Asn Ile Val
        275                 280                 285

Thr Ile Asp Ala Lys Leu Tyr Gly Ala His Ala Gly Asn Leu Asn Leu
    290                 295                 300

Asp Pro Ser Lys Phe Pro Ala Phe Ala Ile Gln Asp Pro Glu Lys Asn
305                 310                 315                 320

Ala Lys Tyr Pro Tyr Asp Gln Ser Lys Glu Val Lys Ala Lys Asp Ile
                325                 330                 335

Gly Lys Phe Ile Gln Asp Val Leu Asp Lys Val Glu Pro Ser Ile
            340                 345                 350

Lys Ser Glu Ala Ile Pro Glu Thr Gln Glu Gly Pro Val Thr Val Val
        355                 360                 365

Val Ala His Ser Tyr Lys Asp Leu Val Leu Asp Asn Glu Lys Asp Val
```

|   |   |   |   |   | 370 |   |   |   |   | 375 |   |   |   |   | 380 |   |
|---|---|---|---|---|---|---|---|---|---|---|---|---|---|---|---|---|

Leu Leu Glu Phe Tyr Ala Pro Trp Cys Gly His Cys Lys Ala Leu Ala
385                     390                     395                     400

Pro Lys Tyr Glu Glu Leu Ala Ser Leu Tyr Lys Asp Ile Pro Glu Val
                405                     410                     415

Thr Ile Ala Lys Ile Asp Ala Thr Ala Asn Asp Val Pro Asp Ser Ile
                420                     425                     430

Thr Gly Phe Pro Thr Ile Lys Leu Phe Ala Ala Gly Ala Lys Asp Ser
            435                     440                     445

Pro Val Glu Tyr Glu Gly Ser Arg Thr Val Glu Asp Leu Ala Asn Phe
        450                     455                     460

Val Lys Glu Asn Gly Lys His Lys Val Asp Ala Leu Glu Val Asp Pro
465                     470                     475                     480

Lys Lys Glu Gln Glu Ser Gly Asp Ala Thr Glu Thr Arg Ala Ala Ser
                485                     490                     495

Asp Glu Thr Glu Thr Pro Ala Ala Thr Ser Asp Asp Lys Ser Glu His
            500                     505                     510

Asp Glu Leu
        515

( 2 ) INFORMATION FOR SEQ ID NO: 4:

( i ) SEQUENCE CHARACTERISTICS:
        ( A ) LENGTH: 511 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

Met Arg Thr Phe Ala Pro Trp Ile Leu Ser Leu Leu Gly Ala Ser Ala
1               5                       10                      15

Val Ala Ser Ala Ala Asp Ala Thr Ala Glu Ala Pro Ser Asp Val Val
            20                      25                      30

Ser Leu Thr Gly Asp Thr Phe Glu Thr Phe Val Lys Glu His Asp Leu
        35                      40                      45

Val Leu Ala Glu Phe Phe Ala Pro Trp Cys Gly His Cys Lys Ala Leu
    50                      55                      60

Ala Pro Lys Tyr Glu Gln Ala Ala Thr Glu Leu Lys Glu Lys Asn Ile
65                      70                      75                      80

Pro Leu Val Lys Val Asp Cys Thr Glu Glu Ala Leu Cys Arg Asp
                85                      90                      95

Gln Gly Val Glu Gly Tyr Pro Thr Leu Lys Ile Phe Arg Gly Leu Asp
                100                     105                     110

Ala Val Lys Pro Tyr Gln Gly Ala Arg Gln Thr Glu Ala Ile Val Ser
            115                     120                     125

Tyr Met Val Lys Gln Ser Leu Pro Ala Val Ser Pro Val Thr Pro Glu
    130                     135                     140

Asn Leu Glu Glu Ile Lys Thr Met Asp Lys Ile Val Val Ile Gly Tyr
145                     150                     155                     160

Ile Ala Ser Asp Asp Gln Thr Ala Asn Asp Ile Phe Thr Thr Phe Ala
                165                     170                     175

Glu Ser Gln Arg Asp Asn Tyr Leu Phe Ala Ala Thr Ser Asp Ala Ser
            180                     185                     190

Ile Ala Lys Ala Glu Gly Val Lys Gln Pro Ser Ile Val Leu Tyr Lys
        195                     200                     205

```
Asp  Phe  Asp  Glu  Lys  Lys  Ala  Thr  Tyr  Asp  Gly  Glu  Ile  Glu  Gln  Asp
     210                 215                 220

Ala  Leu  Leu  Ser  Trp  Val  Lys  Thr  Ala  Ser  Thr  Pro  Leu  Val  Gly  Glu
225                      230                 235                           240

Leu  Gly  Pro  Glu  Thr  Tyr  Ser  Gly  Tyr  Ile  Thr  Ala  Gly  Ile  Pro  Leu
                    245                      250                      255

Ala  Tyr  Ile  Phe  Ala  Glu  Thr  Lys  Glu  Glu  Arg  Glu  Gln  Phe  Thr  Glu
               260                      265                      270

Glu  Phe  Lys  Phe  Ile  Ala  Glu  Lys  His  Lys  Gly  Ser  Ile  Asn  Ile  Val
          275                      280                      285

Thr  Ile  Asp  Ala  Lys  Leu  Tyr  Gly  Ala  His  Ala  Gly  Asn  Leu  Asn  Leu
     290                      295                      300

Asp  Pro  Ser  Lys  Phe  Pro  Ala  Phe  Ala  Ile  Gln  Asp  Pro  Glu  Lys  Asn
305                      310                      315                      320

Ala  Lys  Tyr  Pro  Tyr  Asp  Gln  Ser  Lys  Glu  Val  Lys  Ala  Lys  Asp  Ile
                    325                      330                      335

Gly  Lys  Phe  Ile  Gln  Asp  Val  Leu  Asp  Asp  Lys  Val  Glu  Pro  Ser  Ile
               340                      345                      350

Lys  Ser  Glu  Ala  Ile  Pro  Glu  Thr  Gln  Glu  Gly  Pro  Val  Thr  Val  Val
          355                      360                      365

Val  Ala  His  Ser  Tyr  Lys  Asp  Leu  Val  Leu  Asp  Asn  Glu  Lys  Asp  Val
     370                      375                      380

Leu  Leu  Glu  Phe  Tyr  Ala  Pro  Trp  Cys  Gly  His  Cys  Lys  Ala  Leu  Ala
385                      390                      395                      400

Pro  Lys  Tyr  Glu  Glu  Leu  Ala  Ser  Leu  Tyr  Lys  Asp  Ile  Pro  Glu  Val
                    405                      410                      415

Thr  Ile  Ala  Lys  Ile  Asp  Ala  Thr  Ala  Asn  Asp  Val  Pro  Asp  Ser  Ile
               420                      425                      430

Thr  Gly  Phe  Pro  Thr  Ile  Lys  Leu  Phe  Ala  Ala  Gly  Ala  Lys  Asp  Ser
          435                      440                      445

Pro  Val  Glu  Tyr  Glu  Gly  Ser  Arg  Thr  Val  Glu  Asp  Leu  Ala  Asn  Phe
     450                      455                      460

Val  Lys  Glu  Asn  Gly  Lys  His  Lys  Val  Asp  Ala  Leu  Glu  Val  Asp  Pro
465                      470                      475                      480

Lys  Lys  Glu  Gln  Glu  Ser  Gly  Asp  Ala  Thr  Glu  Thr  Arg  Ala  Ala  Ser
                    485                      490                      495

Asp  Glu  Thr  Glu  Thr  Pro  Ala  Ala  Thr  Ser  Asp  Asp  Lys  Ser  Ala
               500                      505                      510
```

( 2 ) INFORMATION FOR SEQ ID NO: 5:

( i ) SEQUENCE CHARACTERISTICS:
        ( A ) LENGTH: 281 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

```
Met  Arg  Thr  Phe  Ala  Pro  Trp  Ile  Leu  Ser  Leu  Leu  Gly  Ala  Ser  Ala
1                   5                        10                      15

Val  Ala  Ser  Ala  Ala  Asp  Ala  Thr  Ala  Glu  Ala  Pro  Ser  Asp  Val  Val
               20                       25                      30

Ser  Leu  Thr  Gly  Asp  Thr  Phe  Glu  Thr  Phe  Val  Lys  Glu  His  Asp  Leu
          35                       40                      45

Val  Leu  Ala  Glu  Phe  Phe  Ala  Pro  Trp  Cys  Gly  His  Cys  Lys  Ala  Leu
     50                       55                      60
```

| Ala | Pro | Lys | Tyr | Glu | Gln | Ala | Ala | Thr | Glu | Leu | Lys | Glu | Lys | Asn | Ile |
| 65 | | | | 70 | | | | 75 | | | | | | | 80 |

| Pro | Leu | Val | Lys | Val | Asp | Cys | Thr | Glu | Glu | Ala | Leu | Cys | Arg | Asp |
| | | | | 85 | | | | 90 | | | | | 95 | |

| Gln | Gly | Val | Glu | Gly | Tyr | Pro | Thr | Leu | Lys | Ile | Phe | Arg | Gly | Leu | Asp |
| | | | 100 | | | | 105 | | | | | 110 | | | |

| Ala | Val | Lys | Pro | Tyr | Gln | Gly | Ala | Arg | Gln | Thr | Glu | Ala | Ile | Val | Ser |
| | | 115 | | | | | 120 | | | | | 125 | | | |

| Tyr | Met | Val | Lys | Gln | Ser | Leu | Pro | Ala | Val | Ser | Pro | Val | Thr | Pro | Glu |
| | 130 | | | | 135 | | | | | 140 | | | | | |

| Asn | Leu | Glu | Glu | Ile | Lys | Thr | Met | Asp | Lys | Ile | Val | Val | Ile | Gly | Tyr |
| 145 | | | | | 150 | | | | 155 | | | | | | 160 |

| Ile | Ala | Ser | Asp | Asp | Gln | Thr | Ala | Asn | Asp | Ile | Phe | Thr | Thr | Phe | Ala |
| | | | | 165 | | | | 170 | | | | | 175 | | |

| Glu | Ser | Gln | Arg | Asp | Asn | Tyr | Leu | Phe | Ala | Ala | Thr | Ser | Asp | Ala | Ser |
| | | | 180 | | | | | 185 | | | | | 190 | | |

| Ile | Ala | Lys | Ala | Glu | Gly | Val | Lys | Gln | Pro | Ser | Ile | Val | Leu | Tyr | Lys |
| | | 195 | | | | | 200 | | | | | 205 | | | |

| Asp | Phe | Asp | Glu | Lys | Lys | Ala | Thr | Tyr | Asp | Gly | Glu | Ile | Glu | Gln | Asp |
| | 210 | | | | | 215 | | | | | 220 | | | | |

| Ala | Leu | Leu | Ser | Trp | Val | Lys | Thr | Ala | Ser | Thr | Pro | Leu | Val | Gly | Glu |
| 225 | | | | | 230 | | | | | 235 | | | | | 240 |

| Leu | Gly | Pro | Glu | Thr | Tyr | Ser | Gly | Tyr | Ile | Thr | Ala | Gly | Ile | Pro | Leu |
| | | | | 245 | | | | | 250 | | | | | 255 | |

| Ala | Tyr | Ile | Phe | Ala | Glu | Thr | Lys | Glu | Glu | Arg | Glu | Gln | Phe | Thr | Glu |
| | | | 260 | | | | | 265 | | | | | 270 | | |

| Glu | Phe | Lys | Phe | Ile | Ala | Glu | Lys | His |
| | | 275 | | | | | 280 | |

( 2 ) INFORMATION FOR SEQ ID NO: 6:

( i ) SEQUENCE CHARACTERISTICS:
        ( A ) LENGTH: 174 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

| Met | Arg | Thr | Phe | Ala | Pro | Trp | Ile | Leu | Ser | Leu | Leu | Gly | Ala | Ser | Ala |
| 1 | | | | 5 | | | | | 10 | | | | | 15 | |

| Val | Ala | Ser | Ala | Ala | Asp | Ala | Thr | Ala | Glu | Ala | Pro | Ser | Asp | Val | Val |
| | | | | 20 | | | | 25 | | | | | 30 | | |

| Ser | Leu | Thr | Gly | Asp | Thr | Phe | Glu | Thr | Phe | Val | Lys | Glu | His | Asp | Leu |
| | | | 35 | | | | 40 | | | | | 45 | | | |

| Val | Leu | Ala | Glu | Phe | Phe | Ala | Pro | Trp | Cys | Gly | His | Cys | Lys | Ala | Leu |
| | | 50 | | | | | 55 | | | | | 60 | | | |

| Ala | Pro | Lys | Tyr | Glu | Gln | Ala | Ala | Thr | Glu | Leu | Lys | Glu | Lys | Asn | Ile |
| 65 | | | | 70 | | | | 75 | | | | | | | 80 |

| Pro | Leu | Val | Lys | Val | Asp | Cys | Thr | Glu | Glu | Ala | Leu | Cys | Arg | Asp |
| | | | | 85 | | | | 90 | | | | | 95 | |

| Gln | Gly | Val | Glu | Gly | Tyr | Pro | Thr | Leu | Lys | Ile | Phe | Arg | Gly | Leu | Asp |
| | | | 100 | | | | 105 | | | | | 110 | | | |

| Ala | Val | Lys | Pro | Tyr | Gln | Gly | Ala | Arg | Gln | Thr | Glu | Ala | Ile | Val | Ser |
| | | 115 | | | | | 120 | | | | | 125 | | | |

| Tyr | Met | Val | Lys | Gln | Ser | Leu | Pro | Ala | Val | Ser | Pro | Val | Thr | Pro | Glu |

|  |  |  | 130 |  |  |  | 135 |  |  |  | 140 |  |  |  |
|---|---|---|---|---|---|---|---|---|---|---|---|---|---|---|

Asn Leu Glu Glu Ile Lys Thr Met Asp Lys Ile Val Val Ile Gly Tyr
145                     150                 155                 160

Ile Ala Ser Asp Asp Gln Thr Ala Asn Asp Ile Phe Thr Thr
                165                 170

(2) INFORMATION FOR SEQ ID NO: 7:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO: 7:

Met Arg Thr Phe Ala Pro Trp Ile Leu Ser Leu Leu Gly Ala Ser Ala
1               5                   10                  15

Val Ala Ser Ala Ala Asp Ala Thr Ala Glu Ala Pro Ser Asp Val Val
                20                  25                  30

Ser Leu Thr Gly Asp Thr Phe Glu Thr Phe Val Lys Glu His Asp Leu
            35                  40                  45

Val Leu Ala Glu Phe Phe Ala Pro Trp Cys Gly His Cys Lys Ala Leu
        50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
                100                 105                 110

Ala Val Lys Pro Tyr Gln Gly Ala Arg Gln Thr Glu Ala Ile Val Ser
        115                 120                 125

Tyr Met Val Lys Gln Ser Leu Pro Ala Val Ser Pro Val Thr Pro Glu
    130                 135                 140

Asn Leu Glu Glu Ile Lys Thr Met Asp Lys Ile Val Val Ile Gly Tyr
145                 150                 155                 160

Ile Ala Ser (2) INFORMATION FOR SEQ ID NO: 8:

(i) SEQUENCE CHARACTERISTICS:
        (A) LENGTH: 143 amino acids
        (B) TYPE: amino acid
        (D) TOPOLOGY: linear (ii) MOLECULE TYPE: protein (xi) SEQUENCE DESCRIPTION: SEQ ID NO: 8:

Met Arg Thr Phe Ala Pro Trp Ile Leu Ser Leu Leu Gly Ala Ser Ala
1               5                   10                  15

Val Ala Ser Ala Ala Asp Ala Thr Ala Glu Ala Pro Ser Asp Val Val
                20                  25                  30

Ser Leu Thr Gly Asp Thr Phe Glu Thr Phe Val Lys Glu His Asp Leu
            35                  40                  45

Val Leu Ala Glu Phe Phe Ala Pro Trp Cys Gly His Cys Lys Ala Leu
        50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp

```
                                      85                            90                              95
Gln  Gly  Val  Glu  Gly  Tyr  Pro  Thr  Leu  Lys  Ile  Phe  Arg  Gly  Leu  Asp
                    100                      105                    110

Ala  Val  Lys  Pro  Tyr  Gln  Gly  Ala  Arg  Gln  Thr  Glu  Ala  Ile  Val  Ser
          115                      120                    125

Tyr  Met  Val  Lys  Gln  Ser  Leu  Pro  Ala  Val  Ser  Pro  Val  Thr  Pro
     130                      135                    140
```

( 2 ) INFORMATION FOR SEQ ID NO: 9:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

```
Met  Arg  Thr  Phe  Ala  Pro  Trp  Ile  Leu  Ser  Leu  Leu  Gly  Ala  Ser  Ala
 1                        5                       10                       15

Val  Ala  Ser  Ala  Ala  Asp  Ala  Thr  Ala  Glu  Ala  Pro  Ser  Asp  Val  Val
                    20                       25                       30

Ser  Leu  Thr  Gly  Asp  Thr  Phe  Glu  Thr  Phe  Val  Lys  Glu  His  Asp  Leu
               35                       40                       45

Val  Leu  Ala  Glu  Phe  Phe  Ala  Pro  Trp  Cys  Gly  His  Cys  Lys  Ala  Leu
          50                       55                       60

Ala  Pro  Lys  Tyr  Glu  Gln  Ala  Ala  Thr  Glu  Leu  Lys  Glu  Lys  Asn  Ile
 65                       70                       75                       80

Pro  Leu  Val  Lys  Val  Asp  Cys  Thr  Glu  Glu  Ala  Leu  Cys  Arg  Asp
                         85                       90                       95

Gln  Gly  Val  Glu  Gly  Tyr  Pro  Thr  Leu  Lys  Ile  Phe  Arg  Gly  Leu  Asp
                    100                      105                    110

Ala  Val  Lys  Pro  Tyr  Gln  Gly  Ala  Arg  Gln  Thr  Glu  Ala  Ile  Val  Ser
          115                      120                    125

Tyr  Met  Val  Lys  Gln  Ser  Leu  Pro  Ala  Val  Ser  Pro  Val
     130                      135                    140
```

( 2 ) INFORMATION FOR SEQ ID NO: 10:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

```
Met  Arg  Thr  Phe  Ala  Pro  Trp  Ile  Leu  Ser  Leu  Leu  Gly  Ala  Ser  Ala
 1                        5                       10                       15

Val  Ala  Ser  Ala  Ala  Asp  Ala  Thr  Ala  Glu  Ala  Pro  Ser  Asp  Val  Val
                    20                       25                       30

Ser  Leu  Thr  Gly  Asp  Thr  Phe  Glu  Thr  Phe  Val  Lys  Glu  His  Asp  Leu
               35                       40                       45

Val  Leu  Ala  Glu  Phe  Phe  Ala  Pro  Trp  Cys  Gly  His  Cys  Lys  Ala  Leu
          50                       55                       60

Ala  Pro  Lys  Tyr  Glu  Gln  Ala  Ala  Thr  Glu  Leu  Lys  Glu  Lys  Asn  Ile
 65                       70                       75                       80

Pro  Leu  Val  Lys  Val  Asp  Cys  Thr  Glu  Glu  Ala  Leu  Cys  Arg  Asp
                         85                       90                       95
```

| | | | | | | | | | | | | | | |
|---|---|---|---|---|---|---|---|---|---|---|---|---|---|---|
| Gln | Gly | Val | Glu | Gly | Tyr | Pro | Thr | Leu | Lys | Ile | Phe | Arg | Gly | Leu | Asp |
| | | | 100 | | | | 105 | | | | | | 110 | | |
| Ala | Val | Lys | Pro | Tyr | Gln | Gly | Ala | Arg | Gln | Thr | Glu | Ala | Ile | Val | Ser |
| | | | 115 | | | | 120 | | | | | 125 | | | |
| Tyr | Met | Val |
| | | 130 |

(2) INFORMATION FOR SEQ ID NO: 11:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO: 11:

| | | | | | | | | | | | | | | | |
|---|---|---|---|---|---|---|---|---|---|---|---|---|---|---|---|
| Met | Arg | Thr | Phe | Ala | Pro | Trp | Ile | Leu | Ser | Leu | Leu | Gly | Ala | Ser | Ala |
| 1 | | | | 5 | | | | | 10 | | | | | 15 | |
| Val | Ala | Ser | Ala | Ala | Asp | Ala | Thr | Ala | Glu | Ala | Pro | Ser | Asp | Val | Val |
| | | | 20 | | | | 25 | | | | | 30 | | | |
| Ser | Leu | Thr | Gly | Asp | Thr | Phe | Glu | Thr | Phe | Val | Lys | Glu | His | Asp | Leu |
| | | 35 | | | | | 40 | | | | | 45 | | | |
| Val | Leu | Ala | Glu | Phe | Phe | Ala | Pro | Trp | Cys | Gly | His | Cys | Lys | Ala | Leu |
| | 50 | | | | | 55 | | | | | 60 | | | | |
| Ala | Pro | Lys | Tyr | Glu | Gln | Ala | Ala | Thr | Glu | Leu | Lys | Glu | Lys | Asn | Ile |
| 65 | | | | | 70 | | | | | 75 | | | | | 80 |
| Pro | Leu | Val | Lys | Val | Asp | Cys | Thr | Glu | Glu | Ala | Leu | Cys | Arg | Asp |
| | | | | 85 | | | | | 90 | | | | | 95 |
| Gln | Gly | Val | Glu | Gly | Tyr | Pro | Thr | Leu | Lys | Ile | Phe | Arg | Gly | Leu | Asp |
| | | | 100 | | | | 105 | | | | | | 110 | | |
| Ala | Val | Lys | Leu | Ile | Arg | Glu | Leu | Leu | Gln | Glu | Leu | Val | Asn | Lys | His |
| | | | 115 | | | | 120 | | | | | 125 | | | |
| Leu |

(2) INFORMATION FOR SEQ ID NO: 12:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO: 12:

| | | | | | | | | | | | | | | | |
|---|---|---|---|---|---|---|---|---|---|---|---|---|---|---|---|
| Ala | Glu | Ala | Pro | Ser | Asp | Val | Val | Ser | Leu | Thr | Gly | Asp | Thr | Phe | Glu |
| 1 | | | | 5 | | | | | 10 | | | | | 15 | |
| Thr | Phe | Val | Lys | Glu | His | Asp | Leu | Val | Leu | Ala | Glu | Phe | Phe | Ala | Pro |
| | | | 20 | | | | 25 | | | | | 30 | | | |
| Trp | Cys | Gly | His | Cys | Lys | Ala | Leu | Ala | Pro | Lys | Tyr | Glu | Gln | Ala | Ala |
| | | 35 | | | | | 40 | | | | | 45 | | | |
| Thr | Glu | Leu | Lys | Glu | Lys | Asn | Ile | Pro | Leu | Val | Lys | Val | Asp | Cys | Thr |
| | 50 | | | | | 55 | | | | | 60 | | | | |
| Glu | Glu | Glu | Ala | Leu | Cys | Arg | Asp | Gln | Gly | Val | Glu | Gly | Tyr | Pro | Thr |
| 65 | | | | | 70 | | | | | 75 | | | | | 80 |
| Leu | Lys | Ile | Phe | Arg | Gly | Leu | Asp | Ala | Val | Lys | Pro | Tyr | Gln | Gly | Ala |
| | | | | 85 | | | | | 90 | | | | | 95 | |
| Arg | Gln | Thr | Glu | Ala | Ile | Val | Ser | Tyr | Met | Val | Lys | Gln | Ser | Leu | Pro |
| | | | 100 | | | | 105 | | | | | 110 | | | |

| Ala | Val | Ser<br>115 | Pro | Val | Thr | Pro | Glu | Asn<br>120 | Leu | Glu | Glu | Ile | Lys<br>125 | Thr | Met |
| --- | --- | --- | --- | --- | --- | --- | --- | --- | --- | --- | --- | --- | --- | --- | --- |
| Asp | Lys<br>130 | Ile | Val | Val | Ile | Gly<br>135 | Tyr | Ile | Ala | Ser | Asp<br>140 | Asp | Gln | Thr | Ala |
| Asn<br>145 | Asp | Ile | Phe | Thr | Thr<br>150 | Phe | Ala | Glu | Ser | Gln<br>155 | Arg | Asp | Asn | Tyr | Leu<br>160 |
| Phe | Ala | Ala | Thr | Ser<br>165 | Asp | Ala | Ser | Ile | Ala<br>170 | Lys | Ala | Glu | Gly | Val<br>175 | Lys |
| Gln | Pro | Ser | Ile<br>180 | Val | Leu | Tyr | Lys | Asp<br>185 | Phe | Asp | Glu | Lys | Lys<br>190 | Ala | Thr |
| Tyr | Asp | Gly | Glu<br>195 | Ile | Glu | Gln | Asp<br>200 | | | | | | | | |

( 2 ) INFORMATION FOR SEQ ID NO: 13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: primer 4762

( i i i ) HYPOTHETICAL: YES ( i i i ) ANTI-SENSE: NO ( x i ) SEQUENCE DESCRIPTION: SEQ ID NO: 13:

TGGAATTCTG GTGYGGNCAY TGYAA     25

( 2 ) INFORMATION FOR SEQ ID NO: 14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: primer 4763

( i i i ) HYPOTHETICAL: YES ( i i i ) ANTI-SENSE: NO ( x i ) SEQUENCE DESCRIPTION: SEQ ID NO: 14:

TGGGATCCRC ACCANGGNGC RTA     23

( 2 ) INFORMATION FOR SEQ ID NO: 15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: primer 5205

( i i i ) HYPOTHETICAL: YES ( i i i ) ANTI-SENSE: NO ( x i ) SEQUENCE DESCRIPTION: SEQ ID NO: 15:

TTCGGATCCA CCATGCGGAC TTTCGCACC     29

( 2 ) INFORMATION FOR SEQ ID NO: 16:

( i ) SEQUENCE CHARACTERISTICS:
        ( A ) LENGTH: 55 base pairs (B) TYPE: nucleic acid
(C) STRANDEDNESS: single
(D) TOPOLOGY: linear (ii) MOLECULE TYPE: primer 5215

(iii) HYPOTHETICAL: YES (iii) ANTI-SENSE: NO (xi) SEQUENCE DESCRIPTION: SEQ ID NO: 16:

CCAAGCTTTA GAGATGCTTG TTGACAAGCT CCTGGAGGAG CTCCCTGATA AGCTT    55

(2) INFORMATION FOR SEQ ID NO: 17:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: primer 5397

(iii) HYPOTHETICAL: YES (iii) ANTI-SENSE: NO (xi) SEQUENCE DESCRIPTION: SEQ ID NO: 17:

CCAAGCTTTA GACCATGTAT GACACAATCG CCTCGGTCTG ACGAG    45

(2) INFORMATION FOR SEQ ID NO: 18:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: primer 5895

(iii) HYPOTHETICAL: YES (iii) ANTI-SENSE: NO (xi) SEQUENCE DESCRIPTION: SEQ ID NO: 18:

CCAAGCTTTA GACAGGGGAC ACAGCAGGTA G    31

(2) INFORMATION FOR SEQ ID NO: 19:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: primer 5399

(iii) HYPOTHETICAL: YES (iii) ANTI-SENSE: NO (xi) SEQUENCE DESCRIPTION: SEQ ID NO: 19:

CCAAGCTTTA TGGGGTGACA GGGGACA    27

(2) INFORMATION FOR SEQ ID NO: 20:

(i) SEQUENCE CHARACTERISTICS:
(A) LENGTH: 31 base pairs
(B) TYPE: nucleic acid
(C) STRANDEDNESS: single
(D) TOPOLOGY: linear ( i i ) MOLECULE TYPE: primer 5894

( i i i ) HYPOTHETICAL: YES ( i i i ) ANTI-SENSE: NO ( x i ) SEQUENCE DESCRIPTION: SEQ ID NO: 20:

CCAAGCTTTA AGACGCGATA TAACCAATAA C    31

( 2 ) INFORMATION FOR SEQ ID NO: 21:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: primer 5893

( i i i ) HYPOTHETICAL: YES ( i i i ) ANTI-SENSE: NO ( x i ) SEQUENCE DESCRIPTION: SEQ ID NO: 21:

CCAAGCTTTA AGTGGTGAAT ATATCATTGG C    31

( 2 ) INFORMATION FOR SEQ ID NO: 22:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: primer 6314

( i i i ) HYPOTHETICAL: YES ( i i i ) ANTI-SENSE: NO ( x i ) SEQUENCE DESCRIPTION: SEQ ID NO: 22:

CCAAGCTTAG TGTTTCTCGG CGATGAACTT    30

( 2 ) INFORMATION FOR SEQ ID NO: 23:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: primer 5204

( i i i ) HYPOTHETICAL: YES ( i i i ) ANTI-SENSE: NO ( x i ) SEQUENCE DESCRIPTION: SEQ ID NO: 23:

CCAAGCTTTA CGCAGACTTG TCATCGCTAG T    31

( 2 ) INFORMATION FOR SEQ ID NO:24:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:24:

-continued

```
Ala  Pro  Trp  Cys  Gly  His  Cys  Lys
1              5
```

(2) INFORMATION FOR SEQ ID NO:25:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:25:

```
Thr  Ala  Glu  Ala  Pro  Ser  Asp
1              5
```

(2) INFORMATION FOR SEQ ID NO:26:

(i) SEQUENCE CHARACTERISTICS:
      (A) LENGTH: 3052 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:26:

```
Met  Leu  Ser  Arg  Ala  Leu  Leu  Cys  Leu  Ala  Leu  Ala  Trp  Ala  Ala  Arg
1                   5                   10                  15
Val  Gly  Ala  Asp  Ala  Leu  Glu  Glu  Asp  Asn  Val  Leu  Val  Leu  Lys
                    20                  25                  30
Lys  Ser  Asn  Phe  Ala  Glu  Ala  Leu  Ala  Ala  His  Met  Leu  Arg  Arg  Ala
               35                  40                  45
Leu  Leu  Cys  Leu  Ala  Leu  Thr  Ala  Leu  Phe  Arg  Ala  Gly  Ala  Gly  Ala
     50                  55                       60
Pro  Asp  Glu  Glu  Asp  His  Val  Leu  Val  Leu  His  Lys  Gly  Asn  Phe  Asp
65                       70                  75                       80
Glu  Ala  Leu  Ala  Ala  His  Met  Leu  Arg  Arg  Ala  Leu  Leu  Cys  Leu  Ala
                    85                  90                  95
Val  Ala  Ala  Leu  Val  Arg  Ala  Asp  Ala  Pro  Glu  Glu  Glu  Asp  His  Val
               100                      105                 110
Leu  Val  Leu  Arg  Lys  Ser  Asn  Phe  Ala  Glu  Ala  Leu  Ala  Ala  His  Met
               115                      120                 125
Leu  Arg  Arg  Ala  Val  Leu  Cys  Leu  Ala  Leu  Ala  Val  Thr  Ala  Gly  Trp
     130                      135                      140
Ala  Trp  Ala  Ala  Glu  Glu  Glu  Asp  Asn  Val  Leu  Val  Leu  Lys  Ser  Ser
145                      150                      155                 160
Asn  Phe  Ala  Glu  Glu  Leu  Ala  Ala  His  Glu  Pro  Leu  Glu  Glu  Glu  Asp
                         165                 170                 175
Gly  Val  Leu  Val  Leu  Arg  Ala  Ala  Asn  Phe  Glu  Gln  Ala  Leu  Ala  Ala
               180                 185                      190
His  Met  Lys  Phe  Ser  Ala  Gly  Ala  Val  Leu  Ser  Trp  Ser  Ser  Leu  Leu
          195                 200                 205
Leu  Ala  Ser  Ser  Val  Phe  Ala  Gln  Gln  Glu  Ala  Val  Ala  Pro  Glu  Asp
     210                      215                 220
Ser  Ala  Val  Val  Lys  Leu  Ala  Thr  Asp  Ser  Phe  Asn  Glu  Tyr  Ile  Gln
225                      230                 235                      240
Ser  His  Asn  Tyr  Leu  Leu  Val  Glu  Phe  Tyr  Ala  Pro  Trp  Cys  Gly  His
                    245                 250                 255
```

-continued

```
Cys Lys Ala Leu Ala Pro Glu Tyr Ala Lys Ala Ala Ala Lys Leu Lys
            260                 265                 270

Ala Glu Gly Ser Glu Ile Arg Leu Ala Lys Val Asp Ala Thr Glu Glu
        275                 280                 285

Ser Asp Leu Ala Lys Tyr Leu Val Glu Phe Tyr Ala Pro Trp Cys
    290                 295                 300

Gly His Cys Lys Ala Leu Ala Pro Glu Tyr Ala Lys Ala Ala Gly Lys
305                 310                 315                 320

Leu Lys Ala Glu Gly Ser Glu Ile Arg Leu Ala Lys Val Asp Ala Thr
                325                 330                 335

Glu Glu Ser Asp Leu Ala Lys Tyr Leu Val Glu Phe Tyr Ala Pro
            340                 345                 350

Trp Cys Gly His Cys Lys Ala Leu Ala Pro Glu Tyr Ala Lys Ala Ala
        355                 360                 365

Gly Lys Leu Lys Ala Glu Gly Ser Glu Ile Arg Leu Ala Lys Val Asp
    370                 375                 380

Ala Thr Glu Glu Ser Asp Leu Ala Lys Tyr Leu Val Glu Phe Tyr
385                 390                 395                 400

Ala Pro Trp Cys Gly His Cys Lys Ala Leu Ala Pro Glu Tyr Ala Lys
                405                 410                 415

Ala Ala Gly Lys Leu Lys Ala Glu Gly Ser Asp Ile Arg Leu Ala Lys
            420                 425                 430

Val Asp Ala Thr Glu Glu Ser Asp Leu Ala Arg His Leu Leu Val Glu
        435                 440                 445

Phe Tyr Ala Pro Trp Cys Gly His Cys Lys Ala Leu Ala Pro Glu Tyr
    450                 455                 460

Ala Lys Ala Ala Ala Gln Leu Lys Ala Glu Gly Ser Glu Ile Arg Leu
465                 470                 475                 480

Ala Lys Val Asp Ala Thr Glu Glu Ala Glu Leu Ala Asp Leu Val Leu
                485                 490                 495

Ala Glu Phe Phe Ala Pro Trp Cys Gly His Cys Lys Asn Met Ala Pro
            500                 505                 510

Glu Tyr Val Lys Ala Ala Glu Thr Leu Val Glu Lys Asn Ile Thr Leu
        515                 520                 525

Ala Gln Ile Asp Cys Thr Glu Asn Gln Asp Leu Cys Gln Gln Tyr Gly
    530                 535                 540

Val Arg Gly Tyr Pro Thr Ile Lys Phe Phe Lys Asn Gly Asp Thr Ala
545                 550                 555                 560

Ser Pro Lys Glu Tyr Thr Ala Gly Arg Glu Ala Asp Asp Ile Val Asn
                565                 570                 575

Trp Leu Lys Lys Arg Thr Gly Pro Ala Ala Thr Thr Leu Ser Gln Gln
            580                 585                 590

Tyr Gly Val Arg Gly Tyr Pro Thr Ile Lys Phe Phe Lys Asn Gly Asp
        595                 600                 605

Thr Ala Ser Pro Lys Glu Tyr Thr Ala Gly Arg Glu Ala Asp Asp Ile
    610                 615                 620

Val Asn Trp Leu Lys Lys Arg Thr Gly Pro Ala Ala Ser Thr Leu Ser
625                 630                 635                 640

Gln Gln Tyr Gly Val Arg Gly Tyr Pro Thr Ile Lys Phe Phe Arg Asn
                645                 650                 655

Gly Asp Thr Ala Ser Pro Lys Glu Tyr Thr Ala Gly Arg Glu Ala Asp
            660                 665                 670

Asp Ile Val Asn Trp Leu Lys Lys Arg Thr Gly Pro Ala Ala Thr Thr
        675                 680                 685
```

-continued

```
Leu  Arg  Gln  Gln  Tyr  Gly  Val  Arg  Gly  Tyr  Pro  Thr  Ile  Lys  Phe  Phe
690                 695                 700

Lys  Asn  Gly  Asp  Thr  Ala  Ser  Pro  Lys  Glu  Tyr  Thr  Ala  Gly  Arg  Glu
705                 710                 715                 720

Ala  Asp  Asp  Ile  Val  Asn  Trp  Leu  Lys  Lys  Arg  Thr  Gly  Pro  Ala  Ala
                    725                 730                 735

Thr  Thr  Leu  Ala  Gln  Gln  Tyr  Gly  Val  Arg  Gly  Tyr  Pro  Thr  Ile  Lys
               740                 745                 750

Phe  Phe  Arg  Asn  Gly  Asp  Lys  Ala  Ala  Pro  Arg  Glu  Tyr  Thr  Ala  Gly
          755                 760                 765

Arg  Glu  Ala  Asp  Asp  Ile  Val  Ser  Trp  Leu  Lys  Lys  Arg  Thr  Gly  Pro
     770                 775                 780

Ala  Ala  Thr  Thr  Leu  Thr  Met  Glu  His  Asn  Ile  Pro  Gly  Phe  Pro  Ser
785                 790                 795                 800

Leu  Lys  Ile  Phe  Lys  Asn  Ser  Asp  Val  Asn  Asn  Ser  Ile  Asp  Tyr  Glu
                    805                 810                 815

Gly  Pro  Arg  Thr  Ala  Glu  Ala  Val  Gln  Phe  Met  Ile  Lys  Gln  Ser  Gln
               820                 825                 830

Pro  Ala  Val  Ala  Val  Ala  Asp  Thr  Ala  Ala  Ala  Glu  Ser  Leu  Val
          835                 840                 845

Asp  Ser  Ser  Glu  Val  Thr  Val  Ile  Gly  Phe  Phe  Lys  Asp  Ala  Gly  Ser
850                 855                 860

Asp  Ser  Ala  Lys  Gln  Phe  Leu  Leu  Ala  Ala  Glu  Ala  Val  Asp  Asp  Ile
865                 870                 875                 880

Pro  Phe  Gly  Ile  Thr  Ser  Asn  Ser  Asp  Gly  Ala  Ala  Ala  Glu  Ala
                    885                 890                 895

Leu  Val  Glu  Ser  Ser  Glu  Val  Ala  Val  Ile  Gly  Phe  Phe  Lys  Asp  Met
          900                 905                 910

Glu  Ser  Asp  Ser  Ala  Lys  Gln  Phe  Phe  Leu  Ala  Ala  Glu  Val  Ile  Asp
          915                 920                 925

Asp  Ile  Pro  Phe  Gly  Ile  Thr  Ser  Asn  Ser  Asp  Gly  Ala  Ala  Ala
     930                 935                 940

Glu  Ser  Leu  Val  Glu  Ser  Ser  Glu  Val  Ala  Val  Ile  Gly  Phe  Phe  Lys
945                 950                 955                 960

Asp  Val  Glu  Ser  Asp  Ser  Ala  Lys  Gln  Phe  Leu  Gln  Ala  Ala  Glu  Ala
               965                 970                 975

Ile  Asp  Asp  Ile  Pro  Phe  Gly  Ile  Thr  Ser  Asn  Ser  Asp  Asp  Ser  Ala
               980                 985                 990

Ala  Ala  Glu  Ser  Leu  Val  Glu  Ser  Ser  Glu  Val  Ala  Val  Ile  Gly  Phe
     995                 1000                1005

Phe  Lys  Asp  Val  Glu  Ser  Asp  Ala  Ala  Lys  Gln  Phe  Leu  Leu  Ala  Ala
     1010                1015                1020

Glu  Ala  Thr  Asp  Asp  Ile  Pro  Phe  Gly  Leu  Thr  Ala  Ser  Ser  Asp  Asp
1025                1030                1035                1040

Ala  Ala  Ala  Ala  Glu  Thr  Leu  Val  Asp  Ser  Ser  Glu  Val  Val  Val  Ile
               1045                1050                1055

Gly  Phe  Phe  Lys  Asp  Val  Thr  Ser  Asp  Ala  Ala  Lys  Glu  Phe  Leu  Leu
               1060                1065                1070

Ala  Ala  Glu  Ser  Val  Asp  Asp  Ile  Pro  Phe  Gly  Ile  Ser  Ser  Ser  Ala
          1075                1080                1085

Asp  Asp  Leu  Pro  Ala  Tyr  Leu  Ala  Asn  Glu  Thr  Phe  Val  Thr  Pro  Val
1090                1095                1100

Ile  Val  Gln  Ser  Gly  Lys  Ile  Asp  Ala  Asp  Phe  Asn  Ala  Thr  Phe  Tyr
```

-continued

```
          1105                1110                1115                1120

Ser  Met  Ala  Asn  Lys  His  Phe  Asn  Asp  Tyr  Asp  Phe  Val  Ser  Ala  Glu
                        1125                1130                1135

Asn  Ala  Asp  Val  Phe  Ser  Lys  Tyr  Gln  Leu  Asp  Lys  Asp  Gly  Val  Val
                        1140                1145                1150

Leu  Phe  Lys  Lys  Phe  Asp  Glu  Gly  Arg  Asn  Asn  Phe  Glu  Gly  Glu  Ile
                        1155                1160                1165

Thr  Lys  Glu  Lys  Leu  Leu  Asp  Phe  Ile  Lys  His  Asn  Gln  Leu  Pro  Leu
              1170                1175                1180

Val  Ile  Val  Phe  Ser  Lys  Tyr  Gln  Leu  Asp  Lys  Asp  Gly  Val  Val  Leu
    1185                1190                1195                           1200

Phe  Lys  Lys  Phe  Asp  Glu  Gly  Arg  Asn  Asn  Phe  Glu  Gly  Glu  Val  Thr
                        1205                1210                1215

Lys  Glu  Lys  Leu  Leu  Asp  Phe  Ile  Lys  His  Asn  Gln  Leu  Pro  Leu  Val
                        1220                1225                1230

Ile  Val  Phe  Ser  Lys  Tyr  Gln  Leu  Asp  Lys  Asp  Gly  Val  Val  Leu  Phe
                   1235                1240                1245

Lys  Lys  Phe  Asp  Glu  Gly  Arg  Asn  Asn  Phe  Glu  Gly  Glu  Val  Thr  Lys
                   1250                1255                1260

Glu  Asn  Leu  Leu  Asp  Phe  Ile  Lys  His  Asn  Gln  Leu  Pro  Leu  Val  Ile
    1265                1270                1275                           1280

Val  Phe  Ser  Arg  Tyr  Gln  Val  His  Gln  Asp  Gly  Val  Val  Leu  Phe  Lys
                        1285                1290                1295

Lys  Phe  Asp  Glu  Gly  Arg  Asn  Asn  Phe  Glu  Gly  Glu  Val  Thr  Lys  Glu
                   1300                1305                1310

Lys  Leu  Leu  Asp  Phe  Ile  Lys  His  Asn  Gln  Leu  Pro  Leu  Val  Ile  Val
                   1315                1320                1325

Phe  Ser  Lys  Tyr  Gln  Leu  Ser  Gln  Asp  Gly  Val  Val  Leu  Phe  Lys  Lys
                   1330                1335                1340

Phe  Asp  Glu  Gly  Arg  Asn  Asn  Phe  Glu  Gly  Asp  Leu  Thr  Lys  Asp  Asn
    1345                1350                1355                           1360

Leu  Leu  Asn  Phe  Ile  Lys  Ser  Asn  Gln  Leu  Pro  Leu  Val  Ile  Asp  Asp
                        1365                1370                1375

Phe  Lys  Leu  Ser  Ile  Tyr  Leu  Pro  Ser  Ala  Met  Asp  Glu  Pro  Val  Val
                        1380                1385                1390

Tyr  Asn  Gly  Lys  Lys  Ala  Asp  Ile  Ala  Asp  Ala  Asp  Val  Phe  Glu  Lys
                        1395                1400                1405

Trp  Leu  Gln  Val  Glu  Ala  Leu  Pro  Tyr  Phe  Gly  Glu  Phe  Thr  Glu  Gln
                   1410                1415                1420

Thr  Ala  Pro  Lys  Ile  Phe  Gly  Gly  Glu  Ile  Lys  Thr  His  Ile  Leu  Leu
    1425                1430                1435                           1440

Phe  Leu  Pro  Lys  Ser  Val  Ser  Asp  Tyr  Asp  Gly  Lys  Leu  Ser  Asn  Phe
                        1445                1450                1455

Lys  Lys  Ala  Ala  Glu  Gly  Phe  Lys  Gly  Lys  Ile  Glu  Phe  Thr  Glu  Gln
                        1460                1465                1470

Thr  Ala  Pro  Lys  Ile  Phe  Gly  Gly  Glu  Ile  Lys  Thr  His  Ile  Leu  Leu
                   1475                1480                1485

Phe  Leu  Pro  Lys  Ser  Val  Ser  Asp  Tyr  Glu  Gly  Lys  Leu  Ser  Asn  Phe
                   1490                1495                1500

Lys  Lys  Ala  Ala  Glu  Ser  Phe  Lys  Gly  Lys  Ile  Glu  Phe  Thr  Glu  Gln
    1505                1510                1515                           1520

Thr  Ala  Pro  Lys  Ile  Phe  Gly  Gly  Glu  Ile  Lys  Thr  His  Ile  Leu  Leu
                        1525                1530                1535
```

```
Phe Leu Pro Lys Ser Val Ser Asp Tyr Asp Gly Lys Leu Ser Asn Phe
            1540                1545                1550

Lys Thr Ala Ala Glu Ser Phe Lys Gly Lys Ile Glu Phe Thr Glu Gln
            1555                1560                1565

Thr Ala Pro Lys Ile Phe Gly Gly Glu Ile Lys Thr His Ile Leu Leu
            1570                1575                1580

Phe Leu Pro Arg Ser Ala Ala Asp His Asp Gly Lys Leu Ser Gly Phe
1585                1590                1595                1600

Lys Gln Ala Ala Glu Gly Phe Lys Gly Lys Ile Glu Phe Thr Glu Gln
            1605                1610                1615

Thr Ala Pro Lys Ile Phe Gly Gly Glu Ile Lys Thr His Ile Leu Leu
            1620                1625                1630

Phe Leu Pro Lys Ser Val Ser Asp Tyr Glu Gly Lys Leu Asp Asn Phe
            1635                1640                1645

Lys Thr Ala Ala Gly Asn Phe Lys Gly Lys Ile Glu Ile Asp Gly Ser
            1650                1655                1660

Val Phe Ala Gln Tyr Val Glu Ser Gly Leu Pro Leu Gly Tyr Leu Phe
1665                1670                1675                1680

Tyr Asn Asp Glu Glu Glu Leu Glu Glu Tyr Lys Pro Leu Phe Thr Glu
            1685                1690                1695

Leu Ala Lys Lys Asn Arg Gly Leu Phe Ile Phe Ile Asp Ser Asp His
            1700                1705                1710

Thr Asp Asn Gln Arg Ile Leu Glu Phe Phe Gly Leu Lys Lys Glu Glu
            1715                1720                1725

Cys Pro Ala Val Arg Leu Ile Thr Leu Glu Glu Glu Met Thr Lys Tyr
            1730                1735                1740

Leu Phe Ile Phe Ile Asp Ser Asp His Thr Asp Asn Gln Arg Ile Leu
1745                1750                1755                1760

Glu Phe Phe Gly Leu Lys Lys Glu Glu Cys Pro Ala Val Arg Leu Ile
            1765                1770                1775

Thr Leu Glu Glu Glu Met Thr Lys Tyr Leu Phe Ile Phe Ile Asp Ser
            1780                1785                1790

Asp His Thr Asp Asn Gln Arg Ile Leu Glu Phe Phe Gly Leu Lys Lys
            1795                1800                1805

Glu Glu Cys Pro Ala Val Arg Leu Ile Thr Leu Glu Glu Glu Met Thr
            1810                1815                1820

Lys Tyr Leu Phe Ile Phe Ile Asp Ser Asp His Ala Asp Asn Gln Arg
1825                1830                1835                1840

Ile Leu Glu Phe Phe Gly Leu Lys Lys Glu Glu Cys Pro Ala Val Arg
            1845                1850                1855

Leu Ile Thr Leu Glu Glu Glu Met Thr Lys Tyr Leu Phe Ile Phe Ile
            1860                1865                1870

Asp Ser Asp His Ser Asp Asn Gln Arg Ile Leu Glu Phe Phe Gly Leu
            1875                1880                1885

Lys Lys Glu Glu Cys Pro Ala Val Arg Leu Ile Thr Leu Glu Glu Glu
            1890                1895                1900

Met Thr Lys Tyr Leu Met Asn Phe Val Ser Ile Asp Ala Arg Lys Phe
            1905                1910                1915                1920

Gly Arg His Ala Gly Asn Leu Asn Met Lys Glu Gln Phe Pro Leu Phe
            1925                1930                1935

Ala Ile His Asp Met Thr Glu Asp Leu Lys Tyr Gly Leu Pro Gln Leu
            1940                1945                1950

Ser Glu Glu Ala Phe Lys Pro Glu Ser Asp Glu Leu Thr Ala Glu Lys
            1955                1960                1965
```

```
Ile Thr Gln Phe Cys His His Phe Leu Glu Gly Lys Ile Lys Pro His
    1970                1975                1980

Leu Met Ser Gln Glu Leu Pro Glu Asp Trp Asp Lys Gln Pro Val Lys
1985                1990                1995                2000

Val Leu Val Gly Lys Lys Pro Glu Ser Asp Glu Leu Thr Ala Glu Lys
                2005                2010                2015

Ile Thr Glu Phe Cys His Arg Phe Leu Glu Gly Lys Ile Lys Pro His
    2020                2025                2030

Leu Met Ser Gln Glu Leu Pro Asp Asp Trp Asp Lys Gln Pro Val Lys
    2035                2040                2045

Val Leu Val Gly Lys Lys Pro Glu Ser Glu Glu Leu Thr Ala Glu Arg
    2050                2055                2060

Ile Thr Glu Phe Cys His Arg Phe Leu Glu Gly Lys Ile Lys Pro His
2065                2070                2075                2080

Leu Met Ser Gln Glu Arg Ala Asp Gly Asp Trp Asp Lys Gln Pro Val
                2085                2090                2095

Lys Val Pro Val Gly Lys Lys Pro Glu Ser Asp Glu Leu Thr Ala Glu
                2100                2105                2110

Gly Ile Thr Glu Phe Cys Gln Arg Phe Leu Glu Gly Lys Ile Lys Pro
            2115                2120                2125

His Leu Met Ser Gln Glu Leu Pro Asp Glu Asp Trp Asp Arg Gln Pro
        2130                2135                2140

Val Lys Val Leu Val Gly Lys Lys Pro Glu Ser Asp Asp Leu Thr Ala
2145                2150                2155                2160

Asp Lys Ile Lys Glu Phe Cys Asn Lys Phe Leu Glu Gly Lys Ile Lys
                2165                2170                2175

Pro His Leu Met Ser Gln Asp Leu Pro Glu Asp Trp Asp Lys Gln Pro
            2180                2185                2190

Val Lys Val Leu Val Gly Lys Asp Glu Leu Ser Asp Lys Ile Val Leu
            2195                2200                2205

Glu Ser Lys Ala Ile Glu Ser Leu Asx Lys Asp Phe Leu Lys Gly Asp
        2210                2215                2220

Ala Ser Pro Ile Val Lys Ser Gln Glu Ile Phe Glu Asn Gln Asp Ser
2225                2230                2235                2240

Ser Val Phe Gln Leu Val Gly Lys Asn Phe Glu Glu Val Ala Phe Asp
                2245                2250                2255

Glu Lys Lys Asn Val Phe Val Glu Phe Tyr Ala Pro Trp Cys Gly His
                2260                2265                2270

Cys Lys Gln Leu Ala Pro Ile Trp Asp Lys Leu Gly Glu Thr Tyr Lys
            2275                2280                2285

Asp His Glu Asn Ile Ile Ile Ala Lys Asn Phe Glu Glu Val Ala Phe
    2290                2295                2300

Asp Glu Lys Lys Asn Val Phe Val Glu Phe Tyr Ala Pro Trp Cys Gly
2305                2310                2315                2320

His Cys Lys Gln Leu Ala Pro Ile Trp Asp Lys Leu Gly Glu Thr Tyr
                2325                2330                2335

Lys Asp His Glu Asn Ile Ile Ile Ala Lys Asn Phe Glu Asp Val Ala
            2340                2345                2350

Phe Asp Glu Lys Lys Asn Val Phe Val Glu Phe Tyr Ala Pro Trp Cys
        2355                2360                2365

Gly His Cys Lys Gln Leu Ala Pro Ile Trp Asp Lys Leu Gly Glu Thr
    2370                2375                2380

Tyr Lys Asp His Glu Asn Ile Ile Ile Ala Lys Asn Phe Glu Glu Val
```

```
                2385                    2390                   2395                   2400

Ala Phe Asp Glu Lys Lys Asn Val Phe Val Glu Phe Tyr Ala Pro Trp
                        2405                   2410                   2415

Cys Gly His Cys Lys Gln Leu Ala Pro Ile Trp Asp Lys Leu Gly Glu
                        2420                   2425                   2430

Thr Tyr Lys Glu His Gln Asp Ile Val Ile Ala Lys Asn Phe Glu Glu
                        2435                   2440                   2445

Val Ala Phe Asp Glu Asn Lys Asn Val Phe Val Glu Phe Tyr Ala Pro
                        2450                   2455                   2460

Trp Cys Gly His Cys Lys Gln Leu Ala Pro Ala Trp Asp Lys Leu Gly
2465                    2470                   2475                   2480

Pro Thr Tyr Arg Asp His Glu Asn Ile Val Ile Ala Lys Asn His Asp
                        2485                   2490                   2495

Glu Ile Val Asn Asp Pro Lys Lys Asp Val Leu Val Leu Tyr Tyr Ala
                        2500                   2505                   2510

Pro Trp Cys Gly His Cys Lys Arg Leu Ala Pro Thr Tyr Gln Glu Leu
                        2515                   2520                   2525

Ala Asp Thr Tyr Ala Asn Ala Thr Ser Asp Val Leu Ile Ala Lys Met
                        2530                   2535                   2540

Asp Ser Thr Ala Asn Glu Val Glu Ala Val Lys Val His Ser Phe Pro
2545                    2550                   2555                   2560

Thr Leu Lys Phe Phe Pro Ala Ser Ala Asp Arg Thr Val Ile Asp Tyr
                        2565                   2570                   2575

Asn Gly Glu Arg Thr Leu Asp Gly Phe Lys Lys Phe Leu Glu Ser Gly
                        2580                   2585                   2590

Gly Met Asp Ser Thr Ala Asn Glu Val Glu Ala Val Lys Val His Ser
                        2595                   2600                   2605

Phe Pro Thr Leu Lys Phe Phe Pro Ala Ser Ala Asp Arg Thr Val Ile
                        2610                   2615                   2620

Asp Tyr Asn Gly Glu Arg Thr Leu Asp Gly Phe Lys Lys Phe Leu Glu
2625                    2630                   2635                   2640

Ser Gly Gly Met Asp Ser Thr Ala Asn Glu Val Glu Ala Val Lys Val
                        2645                   2650                   2655

His Ser Phe Pro Thr Leu Lys Phe Phe Pro Ala Ser Ala Asp Arg Thr
                        2660                   2665                   2670

Val Ile Asp Tyr Asn Gly Glu Arg Thr Leu Asp Gly Phe Lys Lys Phe
                        2675                   2680                   2685

Leu Glu Ser Gly Gly Met Asp Ser Thr Ala Asn Glu Val Glu Ala Val
2690                    2695                   2700

Lys Val His Ser Phe Pro Thr Leu Lys Phe Phe Pro Ala Gly Pro Gly
2705                    2710                   2715                   2720

Arg Thr Val Ile Asp Tyr Asn Gly Glu Arg Thr Leu Asp Gly Phe Lys
                        2725                   2730                   2735

Lys Phe Leu Glu Ser Gly Gly Met Asp Ser Thr Ala Asn Glu Val Glu
                        2740                   2745                   2750

Ala Val Lys Val His Ser Phe Pro Thr Leu Lys Phe Phe Pro Ala Gly
                        2755                   2760                   2765

Ser Gly Arg Asn Val Ile Asp Tyr Asn Gly Glu Arg Thr Leu Glu Gly
                        2770                   2775                   2780

Phe Lys Lys Phe Leu Glu Ser Gly Gly Leu Asp His Thr Glu Asn Asp
2785                    2790                   2795                   2800

Val Arg Gly Val Val Ile Glu Gly Tyr Pro Thr Ile Val Leu Tyr Pro
                        2805                   2810                   2815
```

```
Gly  Gly  Lys  Lys  Ser  Glu  Ser  Val  Val  Tyr  Gln  Gly  Ser  Arg  Ser  Leu
               2820                2825                2830

Asp  Ser  Leu  Phe  Asp  Phe  Ile  Lys  Glu  Asn  Gly  Gln  Asp  Gly  Ala  Gly
               2835                2840                2845

Asp  Asn  Asp  Asp  Leu  Asp  Leu  Glu  Glu  Ala  Leu  Glu  Pro  Asp  Met  Glu
               2850                2855                2860

Glu  Asp  Asp  Asp  Gln  Lys  Ala  Val  Lys  Asp  Glu  Leu  Gln  Asp  Gly  Ala
2865                2870                2875                          2880

Gly  Asp  Asp  Asp  Asp  Leu  Glu  Asp  Leu  Glu  Glu  Ala  Glu  Glu  Pro  Asp
               2885                2890                2895

Leu  Glu  Glu  Asp  Asp  Asp  Gln  Lys  Ala  Val  Lys  Asp  Glu  Leu  Gln  Asp
               2900                2905                2910

Gly  Ala  Gly  Asp  Asp  Asp  Asp  Leu  Glu  Asp  Leu  Glu  Glu  Ala  Glu  Glu
               2915                2920                2925

Pro  Asp  Met  Glu  Glu  Asp  Asp  Asp  Gln  Lys  Ala  Val  Lys  Asp  Glu  Leu
               2930                2935                2940

Gln  Asp  Gly  Ala  Gly  Asp  Glu  Asp  Gly  Leu  Glu  Asp  Leu  Glu  Glu  Ala
2945                2950                2955                          2960

Glu  Glu  Pro  Asp  Leu  Glu  Glu  Asp  Asp  Asp  Gln  Lys  Ala  Val  Arg  Asp
               2965                2970                2975

Glu  Leu  Gln  Asp  Gly  Ala  Ala  Ala  Asp  Asp  Asp  Leu  Glu  Asp  Leu  Glu
               2980                2985                2990

Thr  Asp  Glu  Glu  Thr  Asp  Leu  Glu  Glu  Gly  Asp  Asp  Asp  Glu  Gln  Lys
               2995                3000                3005

Ile  Gln  Lys  Asp  Glu  Leu  His  Phe  Asp  Val  Asp  Gly  Lys  Ala  Leu  Tyr
               3010                3015                3020

Glu  Glu  Ala  Gln  Glu  Lys  Ala  Ala  Glu  Glu  Ala  Asp  Ala  Asp  Ala  Glu
3025                3030                3035                          3040

Leu  Ala  Asp  Glu  Glu  Asp  Ala  Ile  His  Asp  Glu  Leu
               3045                3050
```

(2) INFORMATION FOR SEQ ID NO:27:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Met  Leu  Ser  Arg  Ala  Leu  Leu  Cys  Leu  Ala  Leu  Ala  Trp  Ala  Ala  Arg
1                   5                   10                  15

Val  Gly  Ala  Asp  Ala  Leu  Glu  Glu  Glu  Asp  Asn  Val  Leu  Val  Leu  Lys
               20                  25                  30

Lys  Ser  Asn  Phe  Ala  Glu  Ala  Leu  Ala  Ala  His  Asn  Tyr  Leu  Leu  Val
               35                  40                  45

Glu  Phe  Tyr  Ala  Pro  Trp  Cys  Gly  His  Cys  Lys  Ala  Leu  Ala  Pro  Glu
     50                       55                      60

Tyr  Ala  Lys  Ala  Ala  Ala  Lys  Leu  Lys  Ala  Glu  Gly  Ser  Glu  Ile  Arg
65                       70                      75                       80

Leu  Ala  Lys  Val  Asp  Ala  Thr  Glu  Glu  Ser  Asp  Leu  Ala  Gln  Gln  Tyr
               85                  90                  95

Gly  Val  Arg  Gly  Tyr  Pro  Thr  Ile  Lys  Phe  Phe  Lys  Asn  Gly  Asp  Thr
               100                 105                 110

Ala  Ser  Pro  Lys  Glu  Tyr  Thr  Ala  Gly  Arg  Glu  Ala  Asp  Asp  Ile  Val
```

|     |     |     |     | 115 |     |     |     |     | 120 |     |     |     |     | 125 |     |     |     |
| --- | --- | --- | --- | --- | --- | --- | --- | --- | --- | --- | --- | --- | --- | --- | --- | --- | --- |
| Asn | Trp | Leu | Lys | Lys | Arg | Thr | Gly | Pro | Ala | Ala | Thr | Thr | Leu | Ser | Asp |
|     | 130 |     |     |     |     | 135 |     |     |     |     | 140 |     |     |     |     |
| Thr | Ala | Ala | Ala | Glu | Ser | Leu | Val | Asp | Ser | Ser | Glu | Val | Thr | Val | Ile |
| 145 |     |     |     |     | 150 |     |     |     |     | 155 |     |     |     |     | 160 |
| Gly | Phe | Phe | Lys | Asp | Ala | Gly | Ser | Asp | Ser | Ala | Lys | Gln | Phe | Leu | Leu |
|     |     |     |     | 165 |     |     |     |     | 170 |     |     |     |     | 175 |     |
| Ala | Ala | Glu | Ala | Val | Asp | Asp | Ile | Pro | Phe | Gly | Ile | Thr | Ser | Asn | Ser |
|     |     |     | 180 |     |     |     |     | 185 |     |     |     |     | 190 |     |     |
| Asp | Val | Phe | Ser | Lys | Tyr | Gln | Leu | Asp | Lys | Asp | Gly | Val | Val | Leu | Phe |
|     |     | 195 |     |     |     |     | 200 |     |     |     |     | 205 |     |     |     |
| Lys | Lys | Phe | Asp | Glu | Gly | Arg | Asn | Asn | Phe | Glu | Gly | Glu | Ile | Thr | Lys |
|     | 210 |     |     |     |     | 215 |     |     |     |     | 220 |     |     |     |     |
| Glu | Lys | Leu | Leu | Asp | Phe | Ile | Lys | His | Asn | Gln | Leu | Pro | Leu | Val | Ile |
| 225 |     |     |     |     | 230 |     |     |     |     | 235 |     |     |     |     | 240 |
| Glu | Phe | Thr | Glu | Gln | Thr | Ala | Pro | Lys | Ile | Phe | Gly | Gly | Glu | Ile | Lys |
|     |     |     |     | 245 |     |     |     |     | 250 |     |     |     |     | 255 |     |
| Thr | His | Ile | Leu | Leu | Phe | Leu | Pro | Lys | Ser | Val | Ser | Asp | Tyr | Asp | Gly |
|     |     |     | 260 |     |     |     |     | 265 |     |     |     |     | 270 |     |     |
| Lys | Leu | Ser | Asn | Phe | Lys | Lys | Ala | Ala | Glu | Gly | Phe | Lys | Gly | Lys | Ile |
|     |     | 275 |     |     |     |     | 280 |     |     |     |     | 285 |     |     |     |
| Leu | Phe | Ile | Phe | Ile | Asp | Ser | Asp | His | Thr | Asp | Asn | Gln | Arg | Ile | Leu |
|     | 290 |     |     |     |     | 295 |     |     |     |     | 300 |     |     |     |     |
| Glu | Phe | Phe | Gly | Leu | Lys | Lys | Glu | Glu | Cys | Pro | Ala | Val | Arg | Leu | Ile |
| 305 |     |     |     |     | 310 |     |     |     |     | 315 |     |     |     |     | 320 |
| Thr | Leu | Glu | Glu | Glu | Met | Thr | Lys | Tyr | Lys | Pro | Glu | Ser | Asp | Glu | Leu |
|     |     |     |     | 325 |     |     |     |     | 330 |     |     |     |     | 335 |     |
| Thr | Ala | Glu | Lys | Ile | Thr | Gln | Phe | Cys | His | His | Phe | Leu | Glu | Gly | Lys |
|     |     |     | 340 |     |     |     |     | 345 |     |     |     |     | 350 |     |     |
| Ile | Lys | Pro | His | Leu | Met | Ser | Gln | Glu | Leu | Pro | Glu | Asp | Trp | Asp | Lys |
|     |     | 355 |     |     |     |     | 360 |     |     |     |     | 365 |     |     |     |
| Gln | Pro | Val | Lys | Val | Leu | Val | Gly | Lys | Asn | Phe | Glu | Glu | Val | Ala | Phe |
|     | 370 |     |     |     |     | 375 |     |     |     |     | 380 |     |     |     |     |
| Asp | Glu | Lys | Lys | Asn | Val | Phe | Val | Glu | Phe | Tyr | Ala | Pro | Trp | Cys | Gly |
| 385 |     |     |     |     | 390 |     |     |     |     | 395 |     |     |     |     | 400 |
| His | Cys | Lys | Gln | Leu | Ala | Pro | Ile | Trp | Asp | Lys | Leu | Gly | Glu | Thr | Tyr |
|     |     |     |     | 405 |     |     |     |     | 410 |     |     |     |     | 415 |     |
| Lys | Asp | His | Glu | Asn | Ile | Ile | Ile | Ala | Lys | Met | Asp | Ser | Thr | Ala | Asn |
|     |     |     | 420 |     |     |     |     | 425 |     |     |     |     | 430 |     |     |
| Glu | Val | Glu | Ala | Val | Lys | Val | His | Ser | Phe | Pro | Thr | Leu | Lys | Phe | Phe |
|     |     | 435 |     |     |     |     | 440 |     |     |     |     | 445 |     |     |     |
| Pro | Ala | Ser | Ala | Asp | Arg | Thr | Val | Ile | Asp | Tyr | Asn | Gly | Glu | Arg | Thr |
|     | 450 |     |     |     |     | 455 |     |     |     |     | 460 |     |     |     |     |
| Leu | Asp | Gly | Phe | Lys | Lys | Phe | Leu | Glu | Ser | Gly | Gly | Gln | Asp | Gly | Ala |
| 465 |     |     |     |     | 470 |     |     |     |     | 475 |     |     |     |     | 480 |
| Gly | Asp | Asn | Asp | Asp | Leu | Asp | Leu | Glu | Glu | Ala | Leu | Glu | Pro | Asp | Met |
|     |     |     |     | 485 |     |     |     |     | 490 |     |     |     |     | 495 |     |
| Glu | Glu | Asp | Asp | Asp | Gln | Lys | Ala | Val | Lys | Asp | Glu | Leu |     |     |     |
|     |     |     | 500 |     |     |     |     | 505 |     |     |     |     |     |     |     |

( 2 ) INFORMATION FOR SEQ ID NO:28:

( i ) SEQUENCE CHARACTERISTICS:
( A ) LENGTH: 510 amino acids
( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:28:

```
Met Leu Arg Arg Ala Leu Leu Cys Leu Ala Leu Thr Ala Leu Phe Arg
 1               5                  10                  15

Ala Gly Ala Gly Ala Pro Asp Glu Glu Asp His Val Leu Val Leu His
            20                  25                  30

Lys Gly Asn Phe Asp Glu Ala Leu Ala Ala His Lys Tyr Leu Leu Val
             35                  40                  45

Glu Phe Tyr Ala Pro Trp Cys Gly His Cys Lys Ala Leu Ala Pro Glu
     50                  55                  60

Tyr Ala Lys Ala Ala Gly Lys Leu Lys Ala Glu Gly Ser Glu Ile Arg
 65                  70                  75                  80

Leu Ala Lys Val Asp Ala Thr Glu Glu Ser Asp Leu Ala Gln Gln Tyr
                 85                  90                  95

Gly Val Arg Gly Tyr Pro Thr Ile Lys Phe Phe Lys Asn Gly Asp Thr
                100                 105                 110

Ala Ser Pro Lys Glu Tyr Thr Ala Gly Arg Glu Ala Asp Asp Ile Val
            115                 120                 125

Asn Trp Leu Lys Lys Arg Thr Gly Pro Ala Ala Ser Thr Leu Ser Asp
            130                 135                 140

Gly Ala Ala Ala Glu Ala Leu Val Glu Ser Ser Glu Val Ala Val Ile
145                 150                 155                 160

Gly Phe Phe Lys Asp Met Glu Ser Asp Ser Ala Lys Gln Phe Phe Leu
                165                 170                 175

Ala Ala Glu Val Ile Asp Asp Ile Pro Phe Gly Ile Thr Ser Asn Ser
            180                 185                 190

Asp Val Phe Ser Lys Tyr Gln Leu Asp Lys Asp Gly Val Val Leu Phe
            195                 200                 205

Lys Lys Phe Asp Glu Gly Arg Asn Asn Phe Glu Gly Glu Val Thr Lys
210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255

Thr His Ile Leu Leu Phe Leu Pro Lys Ser Val Ser Asp Tyr Glu Gly
            260                 265                 270

Lys Leu Ser Asn Phe Lys Lys Ala Ala Glu Ser Phe Lys Gly Lys Ile
            275                 280                 285

Leu Phe Ile Phe Ile Asp Ser Asp His Thr Asp Asn Gln Arg Ile Leu
    290                 295                 300

Glu Phe Phe Gly Leu Lys Lys Glu Glu Cys Pro Ala Val Arg Leu Ile
305                 310                 315                 320

Thr Leu Glu Glu Glu Met Thr Lys Tyr Lys Pro Glu Ser Asp Glu Leu
                325                 330                 335

Thr Ala Glu Lys Ile Thr Glu Phe Cys His Arg Phe Leu Glu Gly Lys
            340                 345                 350

Ile Lys Pro His Leu Met Ser Gln Glu Leu Pro Asp Asp Trp Asp Lys
            355                 360                 365

Gln Pro Val Lys Val Leu Val Gly Lys Asn Phe Glu Glu Val Ala Phe
    370                 375                 380

Asp Glu Lys Lys Asn Val Phe Val Glu Phe Tyr Ala Pro Trp Cys Gly
```

-continued

```
             385                           390                           395                           400
     His  Cys  Lys  Gln  Leu  Ala  Pro  Ile  Trp  Asp  Lys  Leu  Gly  Glu  Thr  Tyr
                         405                           410                           415

Lys  Asp  His  Glu  Asn  Ile  Ile  Ile  Ala  Lys  Met  Asp  Ser  Thr  Ala  Asn
                         420                           425                           430

Glu  Val  Glu  Ala  Val  Lys  Val  His  Ser  Phe  Pro  Thr  Leu  Lys  Phe  Phe
                         435                           440                           445

Pro  Ala  Ser  Ala  Asp  Arg  Thr  Val  Ile  Asp  Tyr  Asn  Gly  Glu  Arg  Thr
                         450                           455                           460

Leu  Asp  Gly  Phe  Lys  Lys  Phe  Leu  Glu  Ser  Gly  Gln  Asp  Gly  Ala
     465                           470                           475                           480

Gly  Asp  Asp  Asp  Asp  Leu  Glu  Asp  Leu  Glu  Ala  Glu  Glu  Pro  Asp
                              485                           490                           495

Leu  Glu  Glu  Asp  Asp  Asp  Gln  Lys  Ala  Val  Lys  Asp  Glu  Leu
                         500                           505                           510
```

( 2 ) INFORMATION FOR SEQ ID NO:29:

( i ) SEQUENCE CHARACTERISTICS:
        ( A ) LENGTH: 509 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
     Met  Leu  Arg  Arg  Ala  Leu  Leu  Cys  Leu  Ala  Val  Ala  Ala  Leu  Val  Arg
     1                        5                           10                            15

Ala  Asp  Ala  Pro  Glu  Glu  Glu  Asp  His  Val  Leu  Val  Leu  Arg  Lys  Ser
                         20                            25                            30

Asn  Phe  Ala  Glu  Ala  Leu  Ala  Ala  His  Lys  Tyr  Leu  Leu  Val  Glu  Phe
                         35                            40                            45

Tyr  Ala  Pro  Trp  Cys  Gly  His  Cys  Lys  Ala  Leu  Ala  Pro  Glu  Tyr  Ala
                         50                            55                            60

Lys  Ala  Ala  Gly  Lys  Leu  Lys  Ala  Glu  Gly  Ser  Glu  Ile  Arg  Leu  Ala
     65                            70                            75                            80

Lys  Val  Asp  Ala  Thr  Glu  Glu  Ser  Asp  Leu  Ala  Gln  Gln  Tyr  Gly  Val
                         85                            90                            95

Arg  Gly  Tyr  Pro  Thr  Ile  Lys  Phe  Phe  Arg  Asn  Gly  Asp  Thr  Ala  Ser
                         100                           105                           110

Pro  Lys  Glu  Tyr  Thr  Ala  Gly  Arg  Glu  Ala  Asp  Asp  Ile  Val  Asn  Trp
                         115                           120                           125

Leu  Lys  Lys  Arg  Thr  Gly  Pro  Ala  Ala  Thr  Thr  Leu  Arg  Asp  Gly  Ala
                         130                           135                           140

Ala  Ala  Glu  Ser  Leu  Val  Glu  Ser  Ser  Glu  Val  Ala  Val  Ile  Gly  Phe
     145                           150                           155                           160

Phe  Lys  Asp  Val  Glu  Ser  Asp  Ser  Ala  Lys  Gln  Phe  Leu  Gln  Ala  Ala
                         165                           170                           175

Glu  Ala  Ile  Asp  Asp  Ile  Pro  Phe  Gly  Ile  Thr  Ser  Asn  Ser  Asp  Val
                         180                           185                           190

Phe  Ser  Lys  Tyr  Gln  Leu  Asp  Lys  Asp  Gly  Val  Val  Leu  Phe  Lys  Lys
                         195                           200                           205

Phe  Asp  Glu  Gly  Arg  Asn  Asn  Phe  Glu  Gly  Glu  Val  Thr  Lys  Glu  Asn
                         210                           215                           220

Leu  Leu  Asp  Phe  Ile  Lys  His  Asn  Gln  Leu  Pro  Leu  Val  Ile  Glu  Phe
     225                           230                           235                           240
```

|     |     |     |     |     |     |     |     |     |     |     |     |     |     |     |
| --- | --- | --- | --- | --- | --- | --- | --- | --- | --- | --- | --- | --- | --- | --- |
| Thr | Glu | Gln | Thr | Ala | Pro | Lys | Ile | Phe | Gly | Gly | Glu | Ile | Lys | Thr | His |
|     |     |     |     | 245 |     |     |     |     | 250 |     |     |     |     | 255 |
| Ile | Leu | Leu | Phe | Leu | Pro | Lys | Ser | Val | Ser | Asp | Tyr | Asp | Gly | Lys | Leu |
|     |     |     | 260 |     |     |     |     | 265 |     |     |     |     | 270 |     |
| Ser | Asn | Phe | Lys | Thr | Ala | Ala | Glu | Ser | Phe | Lys | Gly | Lys | Ile | Leu | Phe |
|     |     | 275 |     |     |     |     | 280 |     |     |     |     | 285 |     |     |
| Ile | Phe | Ile | Asp | Ser | Asp | His | Thr | Asp | Asn | Gln | Arg | Ile | Leu | Glu | Phe |
|     | 290 |     |     |     |     | 295 |     |     |     |     | 300 |     |     |     |
| Phe | Gly | Leu | Lys | Lys | Glu | Glu | Cys | Pro | Ala | Val | Arg | Leu | Ile | Thr | Leu |
| 305 |     |     |     |     | 310 |     |     |     |     | 315 |     |     |     |     | 320 |
| Glu | Glu | Glu | Met | Thr | Lys | Tyr | Lys | Pro | Glu | Ser | Glu | Glu | Leu | Thr | Ala |
|     |     |     |     | 325 |     |     |     |     | 330 |     |     |     |     | 335 |     |
| Glu | Arg | Ile | Thr | Glu | Phe | Cys | His | Arg | Phe | Leu | Glu | Gly | Lys | Ile | Lys |
|     |     |     | 340 |     |     |     |     | 345 |     |     |     |     | 350 |     |     |
| Pro | His | Leu | Met | Ser | Gln | Glu | Arg | Ala | Asp | Gly | Asp | Trp | Asp | Lys | Gln |
|     |     | 355 |     |     |     |     | 360 |     |     |     |     | 365 |     |     |     |
| Pro | Val | Lys | Val | Pro | Val | Gly | Lys | Asn | Phe | Glu | Asp | Val | Ala | Phe | Asp |
|     | 370 |     |     |     |     | 375 |     |     |     |     | 380 |     |     |     |     |
| Glu | Lys | Lys | Asn | Val | Phe | Val | Glu | Phe | Tyr | Ala | Pro | Trp | Cys | Gly | His |
| 385 |     |     |     |     | 390 |     |     |     |     | 395 |     |     |     |     | 400 |
| Cys | Lys | Gln | Leu | Ala | Pro | Ile | Trp | Asp | Lys | Leu | Gly | Glu | Thr | Tyr | Lys |
|     |     |     |     | 405 |     |     |     |     | 410 |     |     |     |     | 415 |     |
| Asp | His | Glu | Asn | Ile | Ile | Ile | Ala | Lys | Met | Asp | Ser | Thr | Ala | Asn | Glu |
|     |     |     |     | 420 |     |     |     |     | 425 |     |     |     |     | 430 |     |
| Val | Glu | Ala | Val | Lys | Val | His | Ser | Phe | Pro | Thr | Leu | Lys | Phe | Phe | Pro |
|     |     |     | 435 |     |     |     |     | 440 |     |     |     |     | 445 |     |     |
| Ala | Ser | Ala | Asp | Arg | Thr | Val | Ile | Asp | Tyr | Asn | Gly | Glu | Arg | Thr | Leu |
|     | 450 |     |     |     |     | 455 |     |     |     |     | 460 |     |     |     |     |
| Asp | Gly | Phe | Lys | Lys | Phe | Leu | Glu | Ser | Gly | Gly | Gln | Asp | Gly | Ala | Gly |
| 465 |     |     |     |     | 470 |     |     |     |     | 475 |     |     |     |     | 480 |
| Asp | Asp | Asp | Asp | Leu | Glu | Asp | Leu | Glu | Glu | Ala | Glu | Glu | Pro | Asp | Met |
|     |     |     |     | 485 |     |     |     |     | 490 |     |     |     |     | 495 |     |
| Glu | Glu | Asp | Asp | Asp | Gln | Lys | Ala | Val | Lys | Asp | Glu | Leu |     |     |     |
|     |     |     |     | 500 |     |     |     | 505 |     |     |     |     |     |     |     |

(2) INFORMATION FOR SEQ ID NO:30:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Leu | Arg | Arg | Ala | Val | Leu | Cys | Leu | Ala | Leu | Ala | Val | Thr | Ala | Gly |
| 1   |     |     |     | 5   |     |     |     |     | 10  |     |     |     |     | 15  |     |
| Trp | Ala | Trp | Ala | Ala | Glu | Glu | Glu | Asp | Asn | Val | Leu | Val | Leu | Lys | Ser |
|     |     |     |     | 20  |     |     |     |     | 25  |     |     |     |     | 30  |     |
| Ser | Asn | Phe | Ala | Glu | Glu | Leu | Ala | Ala | His | Lys | Tyr | Leu | Leu | Val | Glu |
|     |     | 35  |     |     |     |     | 40  |     |     |     |     | 45  |     |     |     |
| Phe | Tyr | Ala | Pro | Trp | Cys | Gly | His | Cys | Lys | Ala | Leu | Ala | Pro | Glu | Tyr |
|     | 50  |     |     |     |     | 55  |     |     |     |     | 60  |     |     |     |     |
| Ala | Lys | Ala | Ala | Gly | Lys | Leu | Lys | Ala | Glu | Gly | Ser | Asp | Ile | Arg | Leu |
| 65  |     |     |     |     | 70  |     |     |     |     | 75  |     |     |     |     | 80  |

|     |     |     |     |     |     |     |     |     |     |     |     |     |     |     |
|---|---|---|---|---|---|---|---|---|---|---|---|---|---|---|
| Ala | Lys | Val | Asp | Ala | Thr | Glu | Glu | Ser | Asp | Leu | Ala | Gln | Gln | Tyr | Gly |
|     |     |     |     | 85  |     |     |     | 90  |     |     |     |     | 95  |     |
| Val | Arg | Gly | Tyr | Pro | Thr | Ile | Lys | Phe | Phe | Lys | Asn | Gly | Asp | Thr | Ala |
|     |     |     |     | 100 |     |     |     | 105 |     |     |     |     | 110 |     |
| Ser | Pro | Lys | Glu | Tyr | Thr | Ala | Gly | Arg | Glu | Ala | Asp | Asp | Ile | Val | Asn |
|     |     |     | 115 |     |     |     | 120 |     |     |     |     | 125 |     |     |
| Trp | Leu | Lys | Lys | Arg | Thr | Gly | Pro | Ala | Ala | Thr | Thr | Leu | Ala | Asp | Ser |
|     |     | 130 |     |     |     | 135 |     |     |     |     | 140 |     |     |     |
| Ala | Ala | Ala | Glu | Ser | Leu | Val | Glu | Ser | Ser | Glu | Val | Ala | Val | Ile | Gly |
| 145 |     |     |     |     | 150 |     |     |     |     | 155 |     |     |     |     | 160 |
| Phe | Phe | Lys | Asp | Val | Glu | Ser | Asp | Ala | Ala | Lys | Gln | Phe | Leu | Leu | Ala |
|     |     |     |     | 165 |     |     |     | 170 |     |     |     |     | 175 |     |
| Ala | Glu | Ala | Thr | Asp | Asp | Ile | Pro | Phe | Gly | Leu | Thr | Ala | Ser | Ser | Asp |
|     |     |     | 180 |     |     |     | 185 |     |     |     |     | 190 |     |     |
| Val | Phe | Ser | Arg | Tyr | Gln | Val | His | Gln | Asp | Gly | Val | Val | Leu | Phe | Lys |
|     |     | 195 |     |     |     | 200 |     |     |     |     | 205 |     |     |     |
| Lys | Phe | Asp | Glu | Gly | Arg | Asn | Asn | Phe | Glu | Gly | Glu | Val | Thr | Lys | Glu |
|     | 210 |     |     |     |     | 215 |     |     |     |     | 220 |     |     |     |
| Lys | Leu | Leu | Asp | Phe | Ile | Lys | His | Asn | Gln | Leu | Pro | Leu | Val | Ile | Glu |
| 225 |     |     |     |     | 230 |     |     |     |     | 235 |     |     |     |     | 240 |
| Phe | Thr | Glu | Gln | Thr | Ala | Pro | Lys | Ile | Phe | Gly | Gly | Glu | Ile | Lys | Thr |
|     |     |     |     | 245 |     |     |     | 250 |     |     |     |     | 255 |     |
| His | Ile | Leu | Leu | Phe | Leu | Pro | Arg | Ser | Ala | Ala | Asp | His | Asp | Gly | Lys |
|     |     |     | 260 |     |     |     | 265 |     |     |     |     | 270 |     |     |
| Leu | Ser | Gly | Phe | Lys | Gln | Ala | Ala | Glu | Gly | Phe | Lys | Gly | Lys | Ile | Leu |
|     |     | 275 |     |     |     | 280 |     |     |     |     | 285 |     |     |     |
| Phe | Ile | Phe | Ile | Asp | Ser | Asp | His | Ala | Asp | Asn | Gln | Arg | Ile | Leu | Glu |
|     | 290 |     |     |     |     | 295 |     |     |     |     | 300 |     |     |     |
| Phe | Phe | Gly | Leu | Lys | Lys | Glu | Glu | Cys | Pro | Ala | Val | Arg | Leu | Ile | Thr |
| 305 |     |     |     |     | 310 |     |     |     |     | 315 |     |     |     |     | 320 |
| Leu | Glu | Glu | Glu | Met | Thr | Lys | Tyr | Lys | Pro | Glu | Ser | Asp | Glu | Leu | Thr |
|     |     |     |     | 325 |     |     |     | 330 |     |     |     |     | 335 |     |
| Ala | Glu | Gly | Ile | Thr | Glu | Phe | Cys | Gln | Arg | Phe | Leu | Glu | Gly | Lys | Ile |
|     |     |     | 340 |     |     |     | 345 |     |     |     |     | 350 |     |     |
| Lys | Pro | His | Leu | Met | Ser | Gln | Glu | Leu | Pro | Asp | Glu | Asp | Trp | Asp | Arg |
|     |     | 355 |     |     |     | 360 |     |     |     |     | 365 |     |     |     |
| Gln | Pro | Val | Lys | Val | Leu | Val | Gly | Lys | Asn | Phe | Glu | Glu | Val | Ala | Phe |
|     | 370 |     |     |     |     | 375 |     |     |     |     | 380 |     |     |     |
| Asp | Glu | Lys | Lys | Asn | Val | Phe | Val | Glu | Phe | Tyr | Ala | Pro | Trp | Cys | Gly |
| 385 |     |     |     |     | 390 |     |     |     |     | 395 |     |     |     |     | 400 |
| His | Cys | Lys | Gln | Leu | Ala | Pro | Ile | Trp | Asp | Lys | Leu | Gly | Glu | Thr | Tyr |
|     |     |     |     | 405 |     |     |     | 410 |     |     |     |     | 415 |     |
| Lys | Glu | His | Gln | Asp | Ile | Val | Ile | Ala | Lys | Met | Asp | Ser | Thr | Ala | Asn |
|     |     |     | 420 |     |     |     | 425 |     |     |     |     | 430 |     |     |
| Glu | Val | Glu | Ala | Val | Lys | Val | His | Ser | Phe | Pro | Thr | Leu | Lys | Phe | Phe |
|     |     | 435 |     |     |     | 440 |     |     |     |     | 445 |     |     |     |
| Pro | Ala | Gly | Pro | Gly | Arg | Thr | Val | Ile | Asp | Tyr | Asn | Gly | Glu | Arg | Thr |
|     | 450 |     |     |     |     | 455 |     |     |     |     | 460 |     |     |     |
| Leu | Asp | Gly | Phe | Lys | Lys | Phe | Leu | Glu | Ser | Gly | Gly | Gln | Asp | Gly | Ala |
| 465 |     |     |     |     | 470 |     |     |     |     | 475 |     |     |     |     | 480 |
| Gly | Asp | Glu | Asp | Gly | Leu | Glu | Asp | Leu | Glu | Glu | Ala | Glu | Glu | Pro | Asp |
|     |     |     |     | 485 |     |     |     | 490 |     |     |     |     | 495 |     |
| Leu | Glu | Glu | Asp | Asp | Asp | Gln | Lys | Ala | Val | Arg | Asp | Glu | Leu |     |     |
|     |     |     | 500 |     |     |     | 505 |     |     |     |     | 510 |     |     |     |

( 2 ) INFORMATION FOR SEQ ID NO:31:

( i ) SEQUENCE CHARACTERISTICS:
        ( A ) LENGTH: 493 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Glu Pro Leu Glu Glu Asp Gly Val Leu Val Leu Arg Ala Ala Asn
 1               5                  10                  15

Phe Glu Gln Ala Leu Ala Ala His Arg His Leu Leu Val Glu Phe Tyr
            20                  25                  30

Ala Pro Trp Cys Gly His Cys Lys Ala Leu Ala Pro Glu Tyr Ala Lys
        35                  40                  45

Ala Ala Ala Gln Leu Lys Ala Glu Gly Ser Glu Ile Arg Leu Ala Lys
    50                  55                  60

Val Asp Ala Thr Glu Glu Ala Glu Leu Ala Gln Gln Phe Gly Val Arg
65                  70                  75                  80

Gly Tyr Pro Thr Ile Lys Phe Phe Arg Asn Gly Asp Lys Ala Ala Pro
                85                  90                  95

Arg Glu Tyr Thr Ala Gly Arg Glu Ala Asp Asp Ile Val Ser Trp Leu
                100                 105                 110

Lys Lys Arg Thr Gly Pro Ala Ala Thr Thr Leu Thr Asp Ala Ala Ala
            115                 120                 125

Ala Glu Thr Leu Val Asp Ser Ser Glu Val Val Val Ile Gly Phe Phe
    130                 135                 140

Lys Asp Val Thr Ser Asp Ala Ala Lys Glu Phe Leu Leu Ala Ala Glu
145                 150                 155                 160

Ser Val Asp Asp Ile Pro Phe Gly Ile Ser Ser Ser Ala Asp Val Phe
                165                 170                 175

Ser Lys Tyr Gln Leu Ser Gln Asp Gly Val Val Leu Phe Lys Lys Phe
                180                 185                 190

Asp Glu Gly Arg Asn Asn Phe Glu Gly Asp Leu Thr Lys Asp Asn Leu
            195                 200                 205

Leu Asn Phe Ile Lys Ser Asn Gln Leu Pro Leu Val Ile Glu Phe Thr
    210                 215                 220

Glu Gln Thr Ala Pro Lys Ile Phe Gly Gly Glu Ile Lys Thr His Ile
225                 230                 235                 240

Leu Leu Phe Leu Pro Lys Ser Val Ser Asp Tyr Glu Gly Lys Leu Asp
                245                 250                 255

Asn Phe Lys Thr Ala Ala Gly Asn Phe Lys Gly Lys Ile Leu Phe Ile
            260                 265                 270

Phe Ile Asp Ser Asp His Ser Asp Asn Gln Arg Ile Leu Glu Phe Phe
    275                 280                 285

Gly Leu Lys Lys Glu Glu Cys Pro Ala Val Arg Leu Ile Thr Leu Glu
    290                 295                 300

Glu Glu Met Thr Lys Tyr Lys Pro Glu Ser Asp Asp Leu Thr Ala Asp
305                 310                 315                 320

Lys Ile Lys Glu Phe Cys Asn Lys Phe Leu Glu Gly Lys Ile Lys Pro
                325                 330                 335

His Leu Met Ser Gln Asp Leu Pro Glu Asp Trp Asp Lys Gln Pro Val
            340                 345                 350
```

|     |     |     |     |     |     |     |     |     |     |     |     |     |     |     |
| --- | --- | --- | --- | --- | --- | --- | --- | --- | --- | --- | --- | --- | --- | --- |
| Lys | Val | Leu<br>355 | Val | Gly | Lys | Asn | Phe<br>360 | Glu | Glu | Val | Ala | Phe<br>365 | Asp | Glu | Asn |
| Lys | Asn<br>370 | Val | Phe | Val | Glu<br>375 | Phe | Tyr | Ala | Pro | Trp<br>380 | Cys | Gly | His | Cys | Lys |
| Gln<br>385 | Leu | Ala | Pro | Ala | Trp<br>390 | Asp | Lys | Leu | Gly | Pro<br>395 | Thr | Tyr | Arg | Asp | His<br>400 |
| Glu | Asn | Ile | Val | Ile<br>405 | Ala | Lys | Met | Asp | Ser<br>410 | Thr | Ala | Asn | Glu | Val<br>415 | Glu |
| Ala | Val | Lys | Ile<br>420 | His | Ser | Phe | Pro | Thr<br>425 | Leu | Lys | Phe | Phe | Pro<br>430 | Ala | Gly |
| Ser | Gly | Arg<br>435 | Asn | Val | Ile | Asp | Tyr<br>440 | Asn | Gly | Glu | Arg | Thr<br>445 | Leu | Glu | Gly |
| Phe | Lys<br>450 | Lys | Phe | Leu | Glu | Ser<br>455 | Gly | Gly | Gln | Asp | Gly<br>460 | Ala | Ala | Ala | Asp |
| Asp<br>465 | Asp | Leu | Glu | Asp | Leu<br>470 | Glu | Thr | Asp | Glu | Glu<br>475 | Thr | Asp | Leu | Glu | Glu<br>480 |
| Gly | Asp | Asp | Asp | Glu<br>485 | Gln | Lys | Ile | Gln | Lys<br>490 | Asp | Glu | Leu | | | |

( 2 ) INFORMATION FOR SEQ ID NO:32:

( i ) SEQUENCE CHARACTERISTICS:
        ( A ) LENGTH: 521 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

|     |     |     |     |     |     |     |     |     |     |     |     |     |     |     |     |
| --- | --- | --- | --- | --- | --- | --- | --- | --- | --- | --- | --- | --- | --- | --- | --- |
| Met<br>1 | Lys | Phe | Ser | Ala<br>5 | Gly | Ala | Val | Leu | Ser<br>10 | Trp | Ser | Ser | Leu | Leu<br>15 | Leu |
| Ala | Ser | Ser | Val<br>20 | Phe | Ala | Gln | Gln | Glu<br>25 | Ala | Val | Ala | Pro | Glu<br>30 | Asp | Ser |
| Ala | Val | Val<br>35 | Lys | Leu | Ala | Thr | Asp<br>40 | Ser | Phe | Asn | Glu | Tyr<br>45 | Ile | Gln | Ser |
| His | Asp<br>50 | Leu | Val | Leu | Ala | Glu<br>55 | Phe | Phe | Ala | Pro | Trp<br>60 | Cys | Gly | His | Cys |
| Lys<br>65 | Asn | Met | Ala | Pro | Glu<br>70 | Tyr | Val | Lys | Ala | Ala<br>75 | Glu | Thr | Leu | Val | Glu<br>80 |
| Lys | Asn | Ile | Thr | Leu<br>85 | Ala | Gln | Ile | Asp | Cys<br>90 | Thr | Glu | Asn | Gln<br>95 | Asp | Leu |
| Cys | Met | Glu | His<br>100 | Asn | Ile | Pro | Gly | Phe<br>105 | Pro | Ser | Leu | Lys | Ile<br>110 | Phe | Lys |
| Asn | Ser | Asp<br>115 | Val | Asn | Asn | Ser | Ile<br>120 | Asp | Tyr | Glu | Gly | Pro<br>125 | Arg | Thr | Ala |
| Glu | Ala<br>130 | Val | Gln | Phe | Met | Ile<br>135 | Lys | Gln | Ser | Gln | Pro<br>140 | Ala | Val | Ala | Val |
| Val<br>145 | Ala | Asp | Leu | Pro | Ala<br>150 | Tyr | Leu | Ala | Asn | Glu<br>155 | Thr | Phe | Val | Thr | Pro<br>160 |
| Val | Ile | Val | Gln | Ser<br>165 | Gly | Lys | Ile | Asp | Ala<br>170 | Asp | Phe | Asn | Ala | Thr<br>175 | Phe |
| Tyr | Ser | Met | Ala<br>180 | Asn | Lys | His | Phe | Asn<br>185 | Asp | Tyr | Asp | Phe | Val<br>190 | Ser | Ala |
| Glu | Asn | Ala<br>195 | Asp | Asp | Asp | Phe | Lys<br>200 | Leu | Ser | Ile | Tyr | Leu<br>205 | Pro | Ser | Ala |
| Met | Asp | Glu | Pro | Val | Val | Tyr | Asn | Gly | Lys | Lys | Ala | Asp | Ile | Ala | Asp |

|     |     |     |     |     | 210 |     |     |     |     | 215 |     |     |     |     | 220 |     |     |     |     |
|---|---|---|---|---|---|---|---|---|---|---|---|---|---|---|---|---|---|---|---|
| Ala 225 | Asp | Val | Phe | Glu | Lys 230 | Trp | Leu | Gln | Val | Glu 235 | Ala | Leu | Pro | Tyr | Phe 240 |
| Gly | Glu | Ile | Asp | Gly 245 | Ser | Val | Phe | Ala | Gln 250 | Tyr | Val | Glu | Ser | Gly 255 | Leu |
| Pro | Leu | Gly | Tyr 260 | Leu | Phe | Tyr | Asn | Asp 265 | Glu | Glu | Leu | Glu 270 | Glu | Tyr |
| Lys | Pro | Leu 275 | Phe | Thr | Glu | Leu | Ala 280 | Lys | Lys | Asn | Arg | Gly 285 | Leu | Met | Asn |
| Phe | Val 290 | Ser | Ile | Asp | Ala | Arg 295 | Lys | Phe | Gly | Arg | His 300 | Ala | Gly | Asn | Leu |
| Asn 305 | Met | Lys | Glu | Gln | Phe 310 | Pro | Leu | Phe | Ala | Ile 315 | His | Asp | Met | Thr | Glu 320 |
| Asp | Leu | Lys | Tyr | Gly 325 | Leu | Pro | Gln | Leu | Ser 330 | Glu | Glu | Ala | Phe | Asp 335 | Glu |
| Leu | Ser | Asp | Lys 340 | Ile | Val | Leu | Glu | Ser 345 | Lys | Ala | Ile | Glu | Ser 350 | Leu | Asx |
| Lys | Asp | Phe 355 | Leu | Lys | Gly | Asp | Ala 360 | Ser | Pro | Ile | Val | Lys 365 | Ser | Gln | Glu |
| Ile | Phe 370 | Glu | Asn | Gln | Asp | Ser 375 | Ser | Val | Phe | Gln | Leu 380 | Val | Gly | Lys | Asn |
| His 385 | Asp | Glu | Ile | Val | Asn 390 | Asp | Pro | Lys | Lys | Asp 395 | Val | Leu | Val | Leu | Tyr 400 |
| Tyr | Ala | Pro | Trp | Cys 405 | Gly | His | Cys | Lys | Arg 410 | Leu | Ala | Pro | Thr | Tyr 415 | Gln |
| Glu | Leu | Ala | Asp 420 | Thr | Tyr | Ala | Asn | Ala 425 | Thr | Ser | Asp | Val | Leu 430 | Ile | Ala |
| Lys | Leu | Asp 435 | His | Thr | Glu | Asn | Asp 440 | Val | Arg | Gly | Val | Val 445 | Ile | Glu | Gly |
| Tyr | Pro 450 | Thr | Ile | Val | Leu | Tyr 455 | Pro | Gly | Gly | Lys | Lys 460 | Ser | Glu | Ser | Val |
| Val 465 | Tyr | Gln | Gly | Ser | Arg 470 | Ser | Leu | Asp | Ser | Leu 475 | Phe | Asp | Phe | Ile | Lys 480 |
| Glu | Asn | Gly | His | Phe 485 | Asp | Val | Asp | Gly | Lys 490 | Ala | Leu | Tyr | Glu | Glu 495 | Ala |
| Gln | Glu | Lys | Ala 500 | Ala | Glu | Glu | Ala 505 | Asp | Ala | Asp | Ala | Glu 510 | Leu | Ala | Asp |
| Glu | Glu | Asp 515 | Ala | Ile | His | Asp | Glu 520 | Leu |

( 2 ) INFORMATION FOR SEQ ID NO:33:

( i ) SEQUENCE CHARACTERISTICS:
        ( A ) LENGTH: 512 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

| Met 1 | Ala | Lys | Asn | Val 5 | Ala | Ile | Phe | Gly | Leu 10 | Leu | Phe | Ser | Leu | Leu 15 | Leu |
|---|---|---|---|---|---|---|---|---|---|---|---|---|---|---|---|
| Leu | Val | Pro | Ser | Gln 20 | Ile | Phe | Ala | Glu | Glu 25 | Ser | Ser | Thr | Asp | Ala 30 | Lys |
| Glu | Phe | Val | Leu 35 | Thr | Leu | Asp | Asn 40 | Thr | Asn | Phe | His | Asp 45 | Thr | Val | Lys |

| Lys | His | Asp | Phe | Ile | Val | Val | Glu | Phe | Tyr | Ala | Pro | Trp | Cys | Gly | His |
|---|---|---|---|---|---|---|---|---|---|---|---|---|---|---|---|
| | 50 | | | | 55 | | | | | 60 | | | | | |

Cys Lys Lys Leu Ala Pro Glu Tyr Glu Lys Ala Ala Ser Ile Leu Ser
65 70 75 80

Thr His Glu Pro Pro Val Val Leu Ala Lys Val Asp Ala Asn Glu Glu
85 90 95

His Asn Lys Asp Leu Ala Ser Glu Asn Asp Val Lys Gly Phe Pro Thr
100 105 110

Ile Lys Ile Phe Arg Asn Gly Lys Asn Ile Gln Glu Tyr Lys Gly
115 120 125

Pro Arg Glu Ala Glu Gly Ile Val Glu Tyr Leu Lys Lys Gln Ser Gly
130 135 140

Pro Ala Ser Thr Glu Ile Lys Ser Ala Asp Asp Ala Thr Ala Phe Val
145 150 155 160

Gly Asp Asn Lys Val Val Ile Val Gly Val Phe Pro Lys Phe Ser Gly
165 170 175

Glu Glu Tyr Asp Asn Phe Ile Ala Leu Ala Glu Lys Leu Arg Ser Asp
180 185 190

Tyr Asp Phe Ala His Thr Leu Asn Ala Lys His Leu Pro Lys Gly Asp
195 200 205

Ser Ser Val Ser Gly Pro Val Arg Leu Phe Lys Pro Phe Asp Glu
210 215 220

Leu Phe Val Asp Ser Lys Asp Phe Asn Val Glu Ala Leu Glu Lys Phe
225 230 235 240

Ile Glu Glu Ser Ser Thr Pro Ile Val Thr Val Phe Asn Asn Glu Pro
245 250 255

Ser Asn His Pro Phe Val Val Lys Phe Asn Ser Pro Asn Ala Lys
260 265 270

Ala Met Leu Phe Ile Asn Phe Thr Thr Glu Gly Ala Glu Ser Phe Lys
275 280 285

Thr Lys Tyr His Glu Val Ala Glu Gln Tyr Lys Gln Gln Gly Val Ser
290 295 300

Phe Leu Val Gly Asp Val Glu Ser Ser Gln Gly Ala Phe Gln Tyr Phe
305 310 315 320

Gly Leu Lys Glu Glu Gln Val Pro Leu Ile Ile Ile Gln His Asn Asp
325 330 335

Gly Lys Lys Phe Phe Lys Pro Asn Leu Glu Leu Asp Gln Leu Pro Thr
340 345 350

Trp Leu Lys Ala Tyr Lys Asp Gly Lys Val Glu Pro Phe Val Lys Ser
355 360 365

Glu Pro Ile Pro Glu Thr Asn Asn Glu Pro Val Lys Val Val Val Gly
370 375 380

Gln Thr Leu Glu Asp Val Val Phe Lys Ser Gly Lys Asn Val Leu Ile
385 390 395 400

Glu Phe Tyr Ala Pro Trp Cys Gly His Cys Lys Gln Leu Ala Pro Ile
405 410 415

Leu Asp Glu Val Ala Val Ser Phe Gln Ser Asp Ala Asp Val Val Ile
420 425 430

Ala Lys Leu Asp Ala Thr Ala Asn Asp Ile Pro Thr Asp Thr Phe Asp
435 440 445

Val Gln Gly Tyr Pro Thr Leu Tyr Phe Arg Ser Ala Ser Gly Lys Leu
450 455 460

Ser Gln Tyr Asp Gly Gly Arg Thr Lys Glu Asp Ile Ile Glu Phe Ile

-continued

|   |   |   |   |   |   |   |   |   |   |   |   |   |   |   |   |
|---|---|---|---|---|---|---|---|---|---|---|---|---|---|---|---|
|   |   | 465 |   |   |   | 470 |   |   |   | 475 |   |   |   | 480 |   |
| Glu | Lys | Asn | Lys | Asp | Lys | Thr | Gly | Ala | Ala | His | Gln | Glu | Val | Glu | Gln |
|   |   |   |   | 485 |   |   |   |   | 490 |   |   |   |   | 495 |   |
| Pro | Lys | Ala | Ala | Ala | Gln | Pro | Glu | Ala | Gln | Pro | Lys | Asp | Glu | Leu |   |
|   |   |   | 500 |   |   |   | 505 |   |   |   | 510 |   |   |   |   |

( 2 ) INFORMATION FOR SEQ ID NO:34:

( i ) SEQUENCE CHARACTERISTICS:
      ( A ) LENGTH: 515 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:34:

| Met | Arg | Thr | Phe | Ala | Pro | Trp | Ile | Leu | Ser | Leu | Leu | Gly | Ala | Ser | Ala |
|---|---|---|---|---|---|---|---|---|---|---|---|---|---|---|---|
| 1 |   |   |   | 5 |   |   |   |   | 10 |   |   |   |   | 15 |   |
| Val | Ala | Ser | Ala | Ala | Asp | Ala | Thr | Ala | Glu | Ala | Pro | Ser | Asp | Val | Val |
|   |   |   | 20 |   |   |   | 25 |   |   |   | 30 |   |   |   |   |
| Ser | Leu | Thr | Gly | Asp | Thr | Phe | Glu | Thr | Phe | Val | Lys | Glu | His | Asp | Leu |
|   |   | 35 |   |   |   | 40 |   |   |   |   | 45 |   |   |   |   |
| Val | Leu | Ala | Glu | Phe | Phe | Ala | Pro | Trp | Cys | Gly | His | Cys | Lys | Ala | Leu |
|   | 50 |   |   |   |   | 55 |   |   |   |   | 60 |   |   |   |   |
| Ala | Pro | Lys | Tyr | Glu | Gln | Ala | Ala | Thr | Glu | Leu | Lys | Glu | Lys | Asn | Ile |
| 65 |   |   |   |   | 70 |   |   |   |   | 75 |   |   |   |   | 80 |
| Pro | Leu | Val | Lys | Val | Asp | Cys | Thr | Glu | Glu | Ala | Leu | Cys | Arg | Asp |   |
|   |   |   |   | 85 |   |   |   |   | 90 |   |   |   | 95 |   |   |
| Gln | Gly | Val | Glu | Gly | Tyr | Pro | Thr | Leu | Lys | Ile | Phe | Arg | Gly | Leu | Asp |
|   |   |   | 100 |   |   |   |   | 105 |   |   |   |   | 110 |   |   |
| Ala | Val | Lys | Pro | Tyr | Gln | Gly | Ala | Arg | Gln | Thr | Glu | Ala | Ile | Val | Ser |
|   |   | 115 |   |   |   |   | 120 |   |   |   |   | 125 |   |   |   |
| Tyr | Met | Val | Lys | Gln | Ser | Leu | Pro | Ala | Val | Ser | Pro | Val | Thr | Pro | Glu |
|   | 130 |   |   |   |   | 135 |   |   |   |   | 140 |   |   |   |   |
| Asn | Leu | Glu | Glu | Ile | Lys | Thr | Met | Asp | Lys | Ile | Val | Val | Ile | Gly | Tyr |
| 145 |   |   |   |   | 150 |   |   |   |   | 155 |   |   |   |   | 160 |
| Ile | Ala | Ser | Asp | Asp | Gln | Thr | Ala | Asn | Asp | Ile | Phe | Thr | Thr | Phe | Ala |
|   |   |   |   | 165 |   |   |   |   | 170 |   |   |   |   | 175 |   |
| Glu | Ser | Gln | Arg | Asp | Asn | Tyr | Leu | Phe | Ala | Ala | Thr | Ser | Asp | Ala | Ser |
|   |   |   | 180 |   |   |   |   | 185 |   |   |   |   | 190 |   |   |
| Ile | Ala | Lys | Ala | Glu | Gly | Val | Lys | Gln | Pro | Ser | Ile | Val | Leu | Tyr | Lys |
|   |   | 195 |   |   |   |   | 200 |   |   |   |   | 205 |   |   |   |
| Asp | Phe | Asp | Glu | Lys | Lys | Ala | Thr | Tyr | Asp | Gly | Glu | Ile | Glu | Gln | Asp |
|   | 210 |   |   |   |   | 215 |   |   |   |   | 220 |   |   |   |   |
| Ala | Leu | Leu | Ser | Trp | Val | Lys | Thr | Ala | Ser | Thr | Pro | Leu | Val | Gly | Glu |
| 225 |   |   |   |   | 230 |   |   |   |   | 235 |   |   |   |   | 240 |
| Leu | Gly | Pro | Glu | Thr | Tyr | Ser | Gly | Tyr | Ile | Thr | Ala | Gly | Ile | Pro | Leu |
|   |   |   |   | 245 |   |   |   |   | 250 |   |   |   |   | 255 |   |
| Ala | Tyr | Ile | Phe | Ala | Glu | Thr | Lys | Glu | Glu | Arg | Glu | Gln | Phe | Thr | Glu |
|   |   |   | 260 |   |   |   |   | 265 |   |   |   |   | 270 |   |   |
| Glu | Phe | Lys | Phe | Ile | Ala | Glu | Lys | His | Lys | Gly | Ser | Ile | Asn | Ile | Val |
|   |   | 275 |   |   |   |   | 280 |   |   |   |   | 285 |   |   |   |
| Thr | Ile | Asp | Ala | Lys | Leu | Tyr | Gly | Ala | His | Ala | Gly | Asn | Leu | Asn | Leu |
|   | 290 |   |   |   |   | 295 |   |   |   |   | 300 |   |   |   |   |
| Asp | Pro | Ser | Lys | Phe | Pro | Ala | Phe | Ala | Ile | Gln | Asp | Pro | Glu | Lys | Asn |
| 305 |   |   |   |   | 310 |   |   |   |   | 315 |   |   |   |   | 320 |

-continued

```
Ala    Lys    Tyr    Pro    Tyr    Asp    Gln    Ser    Lys    Glu    Val    Lys    Ala    Lys    Asp    Ile
                            325                          330                                        335

Gly    Lys    Phe    Ile    Gln    Asp    Val    Leu    Asp    Asp    Lys    Val    Glu    Pro    Ser    Ile
                     340                          345                                 350

Lys    Ser    Glu    Ala    Ile    Pro    Glu    Thr    Gln    Glu    Gly    Pro    Val    Thr    Val    Val
              355                                 360                                 365

Val    Ala    His    Ser    Tyr    Lys    Asp    Leu    Val    Leu    Asp    Asn    Glu    Lys    Asp    Val
       370                                 375                          380

Leu    Leu    Glu    Phe    Tyr    Ala    Pro    Trp    Cys    Gly    His    Cys    Lys    Ala    Leu    Ala
385                                 390                          395                                        400

Pro    Lys    Tyr    Glu    Glu    Leu    Ala    Ser    Leu    Tyr    Lys    Asp    Ile    Pro    Glu    Val
                            405                          410                                        415

Thr    Ile    Ala    Lys    Ile    Asp    Ala    Thr    Ala    Asn    Asp    Val    Pro    Asp    Ser    Ile
                     420                          425                                 430

Thr    Gly    Phe    Pro    Thr    Ile    Lys    Leu    Phe    Ala    Ala    Gly    Ala    Lys    Asp    Ser
              435                                 440                                 445

Pro    Val    Glu    Tyr    Glu    Gly    Ser    Arg    Thr    Val    Glu    Asp    Leu    Ala    Asn    Phe
       450                                 455                          460

Val    Lys    Glu    Asn    Gly    Lys    His    Lys    Val    Asp    Ala    Leu    Glu    Val    Asp    Pro
465                                 470                          475                                        480

Lys    Lys    Glu    Gln    Glu    Ser    Gly    Asp    Ala    Thr    Glu    Thr    Arg    Ala    Ala    Ser
                            485                          490                                        495

Asp    Glu    Thr    Glu    Thr    Pro    Ala    Ala    Thr    Ser    Asp    Asp    Lys    Ser    Glu    His
                     500                                 505                          510

Asp    Glu    Leu
              515
```

(2) INFORMATION FOR SEQ ID NO:35:

(i) SEQUENCE CHARACTERISTICS:
        (A) LENGTH: 530 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Met    Lys    Phe    Ser    Ala    Gly    Ala    Val    Leu    Ser    Trp    Ser    Ser    Leu    Leu    Leu
1                           5                           10                                        15

Ala    Ser    Ser    Val    Phe    Ala    Gln    Gln    Glu    Ala    Val    Ala    Pro    Glu    Asp    Ser
                     20                          25                                 30

Ala    Val    Val    Lys    Leu    Ala    Thr    Asp    Ser    Phe    Asn    Glu    Tyr    Ile    Gln    Ser
              35                                 40                                 45

His    Asp    Leu    Val    Leu    Ala    Glu    Phe    Phe    Ala    Pro    Trp    Cys    Gly    His    Cys
       50                                 55                          60

Lys    Asn    Met    Ala    Pro    Glu    Tyr    Val    Lys    Ala    Ala    Glu    Thr    Leu    Val    Glu
65                                 70                          75                                         80

Lys    Asn    Ile    Thr    Leu    Ala    Gln    Ile    Asp    Cys    Thr    Glu    Asn    Gln    Asp    Leu
                            85                          90                                         95

Cys    Met    Glu    His    Asn    Ile    Pro    Gly    Phe    Pro    Ser    Leu    Lys    Ile    Phe    Lys
                     100                         105                                110

Asn    Arg    Asp    Val    Asn    Asn    Ser    Ile    Asp    Tyr    Glu    Gly    Pro    Arg    Thr    Ala
              115                                120                                125

Glu    Ala    Ile    Val    Gln    Phe    Met    Ile    Lys    Gln    Ser    Gln    Pro    Ala    Val    Ala
       130                                135                          140
```

```
Val  Val  Ala  Asp  Leu  Pro  Ala  Tyr  Leu  Ala  Asn  Glu  Thr  Phe  Val  Thr
145            150                 155                           160

Pro  Val  Ile  Val  Gln  Ser  Gly  Lys  Ile  Asp  Ala  Asp  Phe  Asn  Ala  Thr
               165                 170                           175

Phe  Tyr  Ser  Met  Ala  Asn  Lys  His  Phe  Asn  Asp  Tyr  Asp  Phe  Val  Ser
               180                 185                      190

Ala  Glu  Asn  Ala  Asp  Asp  Asp  Phe  Lys  Leu  Ser  Ile  Tyr  Leu  Pro  Ser
          195                 200                      205

Ala  Met  Asp  Glu  Pro  Val  Val  Tyr  Asn  Gly  Lys  Lys  Ala  Asp  Ile  Ala
          210                 215                 220

Asp  Ala  Asp  Val  Phe  Glu  Lys  Trp  Leu  Gln  Val  Glu  Ala  Leu  Pro  Tyr
225                 230                      235                           240

Phe  Gly  Glu  Ile  Asp  Gly  Ser  Val  Phe  Ala  Gln  Tyr  Val  Glu  Ser  Gly
               245                      250                      255

Leu  Pro  Leu  Gly  Tyr  Leu  Phe  Tyr  Asn  Asp  Glu  Glu  Glu  Leu  Glu  Glu
               260                      265                      270

Tyr  Lys  Pro  Leu  Phe  Thr  Glu  Leu  Ala  Lys  Lys  Asn  Arg  Gly  Leu  Met
          275                      280                 285

Asn  Phe  Val  Ser  Ile  Asp  Ala  Arg  Lys  Phe  Gly  Arg  His  Ala  Gly  Asn
     290                      295                 300

Leu  Asn  Met  Lys  Glu  Gln  Phe  Pro  Leu  Phe  Ala  Ile  His  Asp  Met  Thr
305                      310                      315                      320

Glu  Asp  Leu  Lys  Tyr  Gly  Leu  Pro  Gln  Leu  Ser  Glu  Glu  Ala  Phe  Asp
                325                      330                           335

Glu  Leu  Ser  Asp  Lys  Ile  Val  Leu  Glu  Ser  Lys  Ala  Ile  Glu  Ser  Leu
               340                 345                      350

Val  Lys  Asp  Phe  Leu  Lys  Gly  Asp  Ala  Ser  Pro  Ile  Val  Lys  Ser  Gln
          355                      360                 365

Glu  Ile  Phe  Glu  Asn  Gln  Asp  Ser  Ser  Val  Phe  Gln  Leu  Val  Gly  Lys
370                      375                      380

Asn  His  Asp  Glu  Ile  Val  Asn  Asp  Pro  Lys  Lys  Asp  Val  Leu  Val  Leu
385                      390                 395                           400

Tyr  Tyr  Ala  Pro  Trp  Cys  Gly  His  Cys  Lys  Arg  Leu  Ala  Pro  Thr  Tyr
               405                      410                           415

Gln  Glu  Leu  Ala  Asp  Thr  Tyr  Ala  Asn  Ala  Thr  Ser  Asp  Val  Leu  Ile
               420                 425                      430

Ala  Lys  Leu  Asp  His  Thr  Glu  Asn  Asp  Val  Arg  Gly  Val  Val  Ile  Glu
          435                      440                 445

Gly  Tyr  Pro  Thr  Ile  Val  Leu  Tyr  Pro  Gly  Gly  Lys  Lys  Ser  Glu  Ser
     450                      455                 460

Val  Val  Tyr  Gln  Gly  Ser  Arg  Ser  Leu  Asp  Ser  Leu  Phe  Asp  Phe  Ile
465                      470                 475                           480

Lys  Glu  Asn  Gly  His  Phe  Asp  Val  Asp  Gly  Lys  Ala  Leu  Tyr  Glu  Glu
                485                      490                           495

Ala  Gln  Glu  Lys  Ala  Ala  Glu  Glu  Ala  Glu  Ala  Asp  Ala  Glu  Ala  Glu
               500                 505                      510

Ala  Asp  Ala  Asp  Ala  Glu  Leu  Ala  Asp  Glu  Glu  Asp  Ala  Ile  His  Asp
               515                 520                      525

Glu  Leu
530
```

( 2 ) INFORMATION FOR SEQ ID NO:36:

( i ) SEQUENCE CHARACTERISTICS:

( A ) LENGTH: 510 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:36:

```
Met Leu Arg Arg Ala Leu Leu Cys Leu Ala Leu Thr Ala Leu Phe Arg
 1               5                  10                  15

Ala Gly Ala Gly Ala Pro Asp Glu Glu Asp His Val Leu Val Leu His
            20              25                  30

Lys Gly Asn Phe Asp Glu Ala Leu Ala Ala His Lys Tyr Leu Leu Val
        35                  40                  45

Glu Phe Tyr Ala Pro Trp Cys Gly His Cys Lys Ala Leu Ala Pro Glu
    50              55                  60

Tyr Ala Lys Ala Ala Gly Lys Leu Lys Ala Glu Gly Ser Glu Ile Arg
65                  70                  75                  80

Leu Ala Lys Val Asp Ala Thr Glu Glu Ser Asp Leu Ala Gln Gln Tyr
                85                  90                  95

Gly Val Arg Gly Tyr Pro Thr Ile Lys Phe Phe Lys Asn Gly Asp Thr
            100                 105                 110

Ala Ser Pro Lys Glu Tyr Thr Ala Gly Arg Glu Ala Asp Asp Ile Val
        115                 120                 125

Asn Trp Leu Lys Lys Arg Thr Gly Pro Ala Ala Ser Thr Leu Ser Asp
    130                 135                 140

Gly Ala Ala Ala Glu Ala Leu Val Glu Ser Ser Glu Val Ala Val Ile
145                 150                 155                 160

Gly Phe Phe Lys Asp Met Glu Ser Asp Ser Ala Lys Gln Phe Phe Leu
                165                 170                 175

Ala Ala Glu Val Ile Asp Asp Ile Pro Phe Gly Ile Thr Ser Asn Ser
            180                 185                 190

Asp Val Phe Ser Lys Tyr Gln Leu Asp Lys Asp Gly Val Val Leu Phe
        195                 200                 205

Lys Lys Phe Asp Glu Gly Arg Asn Asn Phe Glu Gly Glu Val Thr Lys
    210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255

Thr His Ile Leu Leu Phe Leu Pro Lys Ser Val Ser Asp Tyr Glu Gly
            260                 265                 270

Lys Leu Ser Asn Phe Lys Lys Ala Ala Glu Ser Phe Lys Gly Lys Ile
        275                 280                 285

Leu Phe Ile Phe Ile Asp Ser Asp His Thr Asp Asn Gln Arg Ile Leu
    290                 295                 300

Glu Phe Glu Gly Leu Lys Lys Glu Glu Cys Pro Ala Val Arg Leu Ile
305                 310                 315                 320

Thr Leu Glu Glu Glu Met Thr Lys Tyr Lys Pro Glu Ser Asp Glu Leu
                325                 330                 335

Thr Ala Glu Lys Ile Thr Glu Phe Cys His Arg Phe Leu Glu Gly Lys
            340                 345                 350

Ile Lys Pro His Leu Met Ser Gln Glu Leu Pro Asp Asp Trp Asp Lys
        355                 360                 365

Gln Pro Val Lys Val Leu Val Gly Lys Asn Phe Glu Glu Val Ala Phe
    370                 375                 380
```

```
Asp  Glu  Lys  Lys  Asn  Val  Phe  Val  Glu  Phe  Tyr  Ala  Pro  Trp  Cys  Gly
385                 390                 395                           400

His  Cys  Lys  Gln  Leu  Ala  Pro  Ile  Trp  Asp  Lys  Leu  Gly  Glu  Thr  Tyr
                    405                      410                      415

Lys  Asp  His  Glu  Asn  Ile  Val  Ile  Ala  Lys  Met  Asp  Ser  Thr  Ala  Asn
               420                      425                      430

Glu  Val  Glu  Ala  Val  Lys  Val  His  Ser  Phe  Pro  Thr  Leu  Lys  Phe  Phe
          435                      440                      445

Pro  Ala  Ser  Ala  Asp  Arg  Thr  Val  Ile  Asp  Tyr  Asn  Gly  Glu  Arg  Thr
     450                 455                      460

Leu  Asp  Gly  Phe  Lys  Lys  Phe  Leu  Glu  Ser  Gly  Gly  Gln  Asp  Gly  Ala
465                 470                      475                           480

Gly  Asp  Asp  Asp  Asp  Leu  Glu  Asp  Leu  Glu  Glu  Ala  Glu  Glu  Pro  Asp
                    485                 490                      495

Leu  Glu  Glu  Asp  Asp  Asp  Gln  Lys  Ala  Val  Lys  Asp  Glu  Leu
               500                 505                      510
```

( 2 ) INFORMATION FOR SEQ ID NO:37:

( i ) SEQUENCE CHARACTERISTICS:
        ( A ) LENGTH: 508 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

```
Met  Leu  Ser  Arg  Ala  Leu  Leu  Cys  Leu  Ala  Leu  Ala  Trp  Ala  Ala  Arg
1                   5                     10                      15

Val  Gly  Ala  Asp  Ala  Leu  Glu  Glu  Glu  Asp  Asn  Val  Leu  Val  Leu  Lys
               20                  25                      30

Lys  Ser  Asn  Phe  Ala  Glu  Pro  Ala  Ala  His  Asn  Tyr  Leu  Leu  Val  Glu
          35                       40                      45

Phe  Tyr  Ala  Pro  Trp  Cys  Gly  His  Cys  Lys  Ala  Leu  Ala  Pro  Glu  Tyr
     50                       55                      60

Ala  Lys  Ala  Ala  Ala  Lys  Leu  Lys  Ala  Glu  Gly  Ser  Glu  Ile  Arg  Leu
65                       70                      75                        80

Ala  Lys  Val  Asp  Ala  Thr  Glu  Glu  Ser  Asp  Leu  Ala  Gln  Gln  Tyr  Gly
               85                       90                      95

Val  Arg  Gly  Tyr  Pro  Thr  Ile  Lys  Phe  Phe  Lys  Asn  Gly  Asp  Thr  Ala
               100                      105                     110

Ser  Pro  Lys  Glu  Tyr  Thr  Ala  Gly  Arg  Glu  Ala  Asp  Asp  Ile  Val  Asn
          115                      120                     125

Trp  Leu  Lys  Lys  Arg  Thr  Gly  Pro  Ala  Ala  Thr  Thr  Leu  Ser  Asp  Thr
     130                      135                     140

Ala  Ala  Ala  Glu  Ser  Leu  Val  Asp  Ser  Ser  Glu  Val  Thr  Val  Ile  Gly
145                      150                     155                       160

Phe  Phe  Lys  Asp  Ala  Gly  Ser  Asp  Ser  Ala  Lys  Gln  Phe  Leu  Leu  Ala
               165                      170                     175

Ala  Glu  Ala  Val  Asp  Asp  Ile  Pro  Phe  Gly  Ile  Thr  Ser  Asn  Ser  Asp
               180                      185                     190

Val  Phe  Ser  Lys  Tyr  Gln  Leu  Asp  Lys  Asp  Gly  Val  Val  Leu  Phe  Lys
          195                      200                     205

Lys  Phe  Asp  Glu  Gly  Arg  Asn  Asn  Phe  Glu  Gly  Glu  Ile  Thr  Lys  Glu
     210                      215                     220

Lys  Leu  Leu  Asp  Phe  Ile  Lys  His  Asn  Gln  Leu  Pro  Leu  Val  Ile  Glu
```

|  |  |  |  | 225 |  |  |  | 230 |  |  |  | 235 |  |  |  | 240 |
|---|---|---|---|---|---|---|---|---|---|---|---|---|---|---|---|---|
| Phe | Thr | Glu | Gln | Thr<br>245 | Ala | Pro | Lys | Ile | Phe<br>250 | Gly | Gly | Glu | Ile | Lys<br>255 | Thr |  |
| His | Ile | Leu | Leu<br>260 | Phe | Leu | Pro | Lys | Ser<br>265 | Val | Ser | Asp | Tyr<br>270 | Asp | Gly | Lys |  |
| Leu | Ser | Asn<br>275 | Phe | Lys | Lys | Ala | Ala<br>280 | Glu | Gly | Phe | Lys | Gly<br>285 | Lys | Ile | Leu |  |
| Phe | Ile<br>290 | Phe | Ile | Asp | Ser | Asp<br>295 | His | Thr | Asp | Asn | Gln<br>300 | Arg | Ile | Leu | Glu |  |
| Phe<br>305 | Phe | Gly | Leu | Lys | Lys<br>310 | Glu | Glu | Cys | Pro | Ala<br>315 | Val | Arg | Leu | Ile | Thr<br>320 |  |
| Leu | Glu | Glu | Glu | Met<br>325 | Thr | Lys | Tyr | Lys | Pro<br>330 | Glu | Ser | Asp | Glu | Leu<br>335 | Thr |  |
| Ala | Glu | Lys | Ile<br>340 | Thr | Gln | Phe | Cys | His<br>345 | His | Phe | Leu | Glu<br>350 | Gly | Lys | Ile |  |
| Lys | Pro | His<br>355 | Leu | Met | Ser | Gln | Glu<br>360 | Leu | Pro | Glu | Asp | Trp<br>365 | Asp | Lys | Gln |  |
| Pro | Val<br>370 | Lys | Val | Leu | Val | Gly<br>375 | Lys | Asn | Phe | Glu | Glu<br>380 | Val | Ala | Phe | Asp |  |
| Glu<br>385 | Lys | Lys | Asn | Val | Phe<br>390 | Val | Glu | Phe | Tyr | Ala<br>395 | Pro | Trp | Cys | Gly | His<br>400 |  |
| Cys | Lys | Gln | Leu | Ala<br>405 | Pro | Ile | Trp | Asp | Lys<br>410 | Leu | Gly | Glu | Thr | Tyr<br>415 | Lys |  |
| Asp | His | Glu | Asn<br>420 | Ile | Val | Ile | Ala | Lys<br>425 | Met | Asp | Ser | Thr | Ala<br>430 | Asn | Glu |  |
| Val | Glu | Ala<br>435 | Val | Lys | Val | His | Ser<br>440 | Phe | Pro | Thr | Leu | Lys<br>445 | Phe | Phe | Pro |  |
| Ala | Ser<br>450 | Ala | Asp | Arg | Thr | Val<br>455 | Ile | Asp | Tyr | Asn | Gly<br>460 | Glu | Arg | Thr | Leu |  |
| Asp<br>465 | Gly | Phe | Lys | Lys | Phe<br>470 | Leu | Glu | Ser | Gly | Arg<br>475 | Gln | Asp | Gly | Ala | Gly<br>480 |  |
| Asp | Asn | Asp | Asp | Leu<br>485 | Asp | Leu | Glu | Glu | Ala<br>490 | Leu | Glu | Pro | Asp | Met<br>495 | Glu |  |
| Glu | Asp | Asp | Asp<br>500 | Gln | Lys | Ala | Val | Lys<br>505 | Asp | Glu | Leu |  |  |  |  |  |

( 2 ) INFORMATION FOR SEQ ID NO:38:

( i ) SEQUENCE CHARACTERISTICS:
        ( A ) LENGTH: 638 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

| Met<br>1 | Lys | Leu | Arg | Lys<br>5 | Ala | Trp | Leu | Leu | Val<br>10 | Leu | Leu | Leu | Ala | Leu<br>15 | Thr |
|---|---|---|---|---|---|---|---|---|---|---|---|---|---|---|---|
| Gln | Leu | Leu | Ala<br>20 | Ala | Ala | Ser | Ala | Gly<br>25 | Asp | Ala | Gln | Glu | Asp<br>30 | Thr | Ser |
| Asp | Thr | Glu<br>35 | Asn | Ala | Thr | Glu | Glu<br>40 | Glu | Glu | Glu | Asp | Asp<br>45 | Asp | Asp | Asp |
| Leu | Glu<br>50 | Val | Lys | Glu | Glu | Asn<br>55 | Gly | Val | Trp | Val | Leu<br>60 | Asn | Asp | Gly | Asn |
| Phe<br>65 | Asp | Asn | Phe | Val | Ala<br>70 | Asp | Lys | Asp | Thr | Val<br>75 | Leu | Leu | Glu | Phe | Tyr<br>80 |

| | | | | | | | | | | | | | | |
|---|---|---|---|---|---|---|---|---|---|---|---|---|---|---|
| Ala | Pro | Trp | Cys | Gly<br>85 | His | Cys | Lys | Gln | Phe<br>90 | Ala | Pro | Glu | Tyr | Glu<br>95 |
| Ile | Ala | Ser | Thr<br>100 | Leu | Lys | Asp | Asn | Asp<br>105 | Pro | Pro | Ile | Ala<br>110 | Val | Ala | Lys |
| Ile | Asp | Ala | Thr<br>115 | Ser | Ala | Ser | Met<br>120 | Leu | Ala | Ser | Lys<br>125 | Phe | Asp | Val | Ser |
| Gly | Tyr | Pro<br>130 | Thr | Ile | Lys | Ile<br>135 | Leu | Lys | Lys | Gly<br>140 | Gln | Ala | Val | Asp | Tyr |
| Asp<br>145 | Gly | Ser | Arg | Thr | Gln<br>150 | Glu | Glu | Ile | Val<br>155 | Ala | Lys | Val | Arg | Glu | Val<br>160 |
| Ser | Gln | Pro | Asp | Trp<br>165 | Thr | Pro | Pro | Glu | Val<br>170 | Thr | Leu | Ser | Leu<br>175 | Thr |
| Lys | Asp | Asn | Phe<br>180 | Asp | Asp | Val | Val | Asn<br>185 | Ala | Asp | Ile | Ile<br>190 | Leu | Val |
| Glu | Phe | Tyr<br>195 | Ala | Pro | Trp | Cys | Gly<br>200 | His | Cys | Lys | Lys<br>205 | Leu | Ala | Pro | Glu |
| Tyr | Glu<br>210 | Lys | Ala | Ala | Lys | Glu<br>215 | Leu | Ser | Lys | Arg | Ser<br>220 | Pro | Pro | Ile | Pro |
| Leu<br>225 | Ala | Lys | Val | Asp | Ala<br>230 | Thr | Glu | Gln | Thr | Asp<br>235 | Leu | Ala | Lys | Arg | Phe<br>240 |
| Asp | Val | Ser | Gly | Tyr<br>245 | Pro | Thr | Leu | Lys | Ile<br>250 | Phe | Arg | Lys | Gly | Arg<br>255 | Pro |
| Phe | Asp | Tyr | Asn<br>260 | Gly | Pro | Arg | Glu | Lys<br>265 | Tyr | Gly | Ile | Val | Asp<br>270 | Tyr | Met |
| Ile | Glu | Gln | Ser<br>275 | Gly | Pro | Pro | Ser<br>280 | Lys | Glu | Ile | Leu | Thr<br>285 | Leu | Lys | Gln |
| Val | Gln<br>290 | Glu | Phe | Leu | Lys | Asp<br>295 | Gly | Asp | Val | Val<br>300 | Ile | Ile | Gly | Leu |
| Phe<br>305 | Gln | Gly | Asp | Gly | Asp<br>310 | Pro | Ala | Tyr | Leu | Gln<br>315 | Tyr | Gln | Asp | Ala | Ala<br>320 |
| Asn | Asn | Leu | Arg | Glu<br>325 | Asp | Tyr | Lys | Phe | His<br>330 | His | Thr | Phe | Ser | Pro<br>335 | Glu |
| Ile | Ala | Lys | Phe<br>340 | Leu | Lys | Val | Ser | Leu<br>345 | Gly | Lys | Leu | Val | Leu<br>350 | Thr | His |
| Pro | Glu | Lys<br>355 | Phe | Gln | Ser | Lys | Tyr<br>360 | Glu | Pro | Arg | Phe | His<br>365 | Val | Met | Asp |
| Val | Gln | Gly<br>370 | Ser | Thr | Glu | Ala<br>375 | Ser | Ala | Ile | Lys | Asp<br>380 | Tyr | Val | Val | Lys |
| His<br>385 | Ala | Leu | Pro | Leu | Val<br>390 | Gly | His | Arg | Lys | Thr<br>395 | Ser | Asn | Asp | Ala | Lys<br>400 |
| Arg | Tyr | Ser | Lys | Arg<br>405 | Pro | Leu | Val | Val | Val<br>410 | Tyr | Tyr | Ser | Val | Asp<br>415 | Phe |
| Ser | Phe | Asp | Tyr<br>420 | Arg | Ala | Ala | Thr | Gln<br>425 | Phe | Trp | Arg | Asn | Lys<br>430 | Val | Leu |
| Glu | Val | Ala | Lys<br>435 | Asp | Phe | Pro | Glu | Tyr<br>440 | Thr | Phe | Ala | Ile<br>445 | Ala | Asp | Glu |
| Glu | Asp<br>450 | Tyr | Ala | Thr | Glu | Val<br>455 | Lys | Asp | Leu | Gly<br>460 | Leu | Ser | Glu | Ser | Gly |
| Glu<br>465 | Asp | Val | Asn | Ala | Ala<br>470 | Ile | Leu | Asp | Glu | Ser<br>475 | Gly | Lys | Lys | Phe | Ala<br>480 |
| Met | Glu | Pro | Glu | Glu<br>485 | Phe | Asp | Ser | Asp | Thr<br>490 | Leu | Arg | Glu | Phe | Val<br>495 | Thr |
| Ala | Phe | Lys | Lys | Gly | Lys | Leu | Lys | Pro | Val | Ile | Lys | Ser | Gln | Pro | Val |

-continued

|  |  |  |  |  | 500 |  |  |  |  | 505 |  |  |  | 510 |  |
|---|---|---|---|---|---|---|---|---|---|---|---|---|---|---|---|
| Pro | Lys | Asn<br>515 | Asn | Lys | Gly | Pro | Val<br>520 | Lys | Val | Val | Val | Gly<br>525 | Lys | Thr | Phe |
| Asp | Ala<br>530 | Ile | Val | Met | Asp | Pro<br>535 | Lys | Lys | Asp | Val | Leu<br>540 | Ile | Glu | Phe | Tyr |
| Ala<br>545 | Pro | Trp | Cys | Gly | His<br>550 | Cys | Lys | Gln | Leu | Glu<br>555 | Pro | Ile | Tyr | Thr | Ser<br>560 |
| Leu | Gly | Lys | Lys | Tyr<br>565 | Lys | Gly | Gln | Lys | Asp<br>570 | Leu | Val | Ile | Ala | Lys<br>575 | Met |
| Asp | Ala | Thr | Ala<br>580 | Asn | Asp | Ile | Thr | Asn<br>585 | Asp | Gln | Tyr | Lys | Val<br>590 | Glu | Gly |
| Phe | Pro | Thr<br>595 | Ile | Tyr | Phe | Ala | Pro<br>600 | Ser | Gly | Asp | Lys | Lys<br>605 | Asn | Pro | Ile |
| Lys | Phe<br>610 | Glu | Gly | Gly | Asn | Arg<br>615 | Asp | Leu | Glu | His | Leu<br>620 | Ser | Lys | Phe | Ile |
| Asp<br>625 | Glu | His | Ala | Thr | Lys<br>630 | Arg | Ser | Arg | Thr | Lys<br>635 | Glu | Glu | Leu |  |  |

I claim:

1. An isolated active protein disulfide isomerase enzyme, comprising an amino acid sequence selected from the group consisting of SEQ ID NO:5, SEQ ID NO:6, SEQ ID NO:7, SEQ ID NO:8, SEQ ID NO:9, SEQ ID NO:10, and SEQ ID NO: 12.

2. An enzyme composition comprising the protein disulfide isomerase enzyme of claim 1.

3. The composition of claim 2, in the form of a non-dusting granulate, stabilized liquid or protected enzyme.

4. The composition of claim 2, wherein the protein disulfide isomerase is present in an amount between about 0.01–200 mg of enzyme protein/g.

5. The composition of claim 4, wherein the protein disulfide isomerase is present in an amount between about 0.01–20 mg of enzyme protein/g.

6. The composition of claim 5, wherein the protein disulfide isomerase is present in an amount between about 0.01–2 mg of enzyme protein/g.

7. The composition of claim 6, wherein the protein disulfide isomerase is present in an amount between about 0.02–0.2 mg of enzyme protein/g.

8. The composition of claim 6, wherein the protein disulfide isomerase is present in an amount between about 0.01–0.2 mg of enzyme protein/g.

9. The composition of claim 2 further comprising another enzyme selected from the group consisting of a protease, an amylase, a lipase, a peroxidase and a cellulase.

10. A pharmaceutical composition comprising the enzyme of claim 1.

11. A process for treating scleroproteins, comprising applying the composition of claim 2 to a scleroprotein.

12. The process of claim 11, wherein said scleroprotein is human hair or skin, or animal hair or skin.

13. The process of claim 12, wherein said process involves waving, straightening, removing, degrading or softening of hair, or softening or restoration of skin.

14. The isolated enzyme of claim 1 obtained from *Aspergillus oryzae*, IFO 4177 or *Aspergillus niger* 524 (ATCC 16882).

15. An active protein disulfide isomerase enzyme comprising the amino acid sequence of SEQ ID NO:11 or SEQ ID NO: 4.

16. The isolated enzyme of claim 15 derived from *Aspergillus oryzae*, IFO 4177 or *Aspergillus niger* 524 (ATCC 16882).

17. An enzyme composition comprising the protein disulfide isomerase enzyme of claim 15.

18. The composition of claim 17, in the form of a non-dusting granulate, stabilized liquid or protected enzyme.

19. The composition of claim 17, wherein the protein disulfide isomerase is present in an amount between about 0.01–200 mg of enzyme protein/g.

20. The composition of claim 19, wherein the protein disulfide isomerase is present in an amount between about 0.01–20 mg of enzyme protein/g.

21. The composition of claim 20, wherein the protein disulfide isomerase is present in an amount between about 0.01–2 mg of enzyme protein/g.

22. The composition of claim 21, wherein the protein disulfide isomerase is present in an amount between about 0.02–0.2 mg of enzyme protein/g.

23. The composition of claim 21, wherein the protein disulfide isomerase is present in an amount between about 0.01–0.2 mg of enzyme protein/g.

24. The composition of claim 17 further comprising another enzyme selected from the group consisting of a protease, an amylase, a lipase, a peroxidase and a cellulase.

25. A pharmaceutical composition comprising the enzyme of claim 15.

26. A process for treating scleroproteins, comprising applying the composition of claim 17 to a scleroprotein.

27. The process of claim 26, wherein said scleroprotein is human hair or skin, or animal hair or skin.

28. The process of claim 27, wherein said process involves waving, straightening, removing, degrading or softening of hair, or softening or restoration of skin.

* * * * *